US010857262B2

(12) United States Patent
Brown et al.

(10) Patent No.: US 10,857,262 B2
(45) Date of Patent: *Dec. 8, 2020

(54) COMPOSITIONS COMPRISING LOW MOLECULAR WEIGHT SILK FIBROIN FRAGMENTS AND PLASTICIZERS

(71) Applicant: Sofregen Medical, Inc., Medford, MA (US)

(72) Inventors: Joseph E. Brown, Melrose, MA (US); Christopher P. Gulka, Medford, MA (US); Anh Hoang-Lindsay, Boston, MA (US)

(73) Assignee: Sofregen Medical, Inc., Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/799,408

(22) Filed: Oct. 31, 2017

(65) Prior Publication Data

US 2018/0272030 A1   Sep. 27, 2018

Related U.S. Application Data

(60) Provisional application No. 62/571,670, filed on Oct. 12, 2017, provisional application No. 62/488,402, filed on Apr. 21, 2017, provisional application No. 62/482,949, filed on Apr. 7, 2017, provisional application No. 62/415,107, filed on Oct. 31, 2016.

(51) Int. Cl.
| | |
|---|---|
| *A61L 27/00* | (2006.01) |
| *A61L 27/22* | (2006.01) |
| *A61L 27/56* | (2006.01) |
| *C08L 5/08* | (2006.01) |
| *C08K 5/00* | (2006.01) |
| *C08L 89/00* | (2006.01) |
| *A61L 27/50* | (2006.01) |
| *C08K 5/053* | (2006.01) |
| *A61L 27/26* | (2006.01) |

(52) U.S. Cl.
CPC ........... *A61L 27/227* (2013.01); *A61L 27/26* (2013.01); *A61L 27/502* (2013.01); *A61L 27/56* (2013.01); *C08K 5/0016* (2013.01); *C08K 5/053* (2013.01); *C08L 5/08* (2013.01); *C08L 89/00* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 5,034,135 A | 7/1991 | Fischel | |
| 5,234,608 A | 8/1993 | Duff | |
| 5,245,012 A | 9/1993 | Lombari et al. | |
| 5,591,828 A | 1/1997 | Bosslet et al. | |
| 6,287,340 B1 | 9/2001 | Altman et al. | |
| 6,673,285 B2 | 1/2004 | Ma | |
| 7,635,755 B2 | 12/2009 | Kaplan et al. | |
| 7,662,409 B2 | 2/2010 | Masters | |
| 7,842,780 B2 | 11/2010 | Kaplan et al. | |
| 8,128,984 B2 * | 3/2012 | Knight | A61L 27/3604 427/2.26 |
| 8,178,656 B2 | 5/2012 | Kaplan et al. | |
| 8,187,616 B2 | 5/2012 | Wang et al. | |
| 9,187,538 B2 | 11/2015 | Altman et al. | |
| 2002/0143291 A1 | 10/2002 | Slater | |
| 2003/0014010 A1 | 1/2003 | Carpenter et al. | |
| 2005/0276791 A1 | 12/2005 | Hansford et al. | |
| 2006/0063715 A1 | 3/2006 | Whitlow et al. | |
| 2006/0273279 A1 * | 12/2006 | Kaplan | A61L 27/227 252/1 |
| 2007/0187862 A1 | 8/2007 | Kaplan et al. | |
| 2007/0212730 A1 | 9/2007 | Vepari et al. | |
| 2008/0038236 A1 | 2/2008 | Gimble et al. | |
| 2008/0085272 A1 | 4/2008 | Kaplan et al. | |
| 2008/0213564 A1 | 9/2008 | Ma et al. | |
| 2008/0280360 A1 | 11/2008 | Kaplan et al. | |
| 2008/0293919 A1 | 11/2008 | Kaplan et al. | |
| 2008/0317816 A1 | 12/2008 | Ma et al. | |
| 2009/0004737 A1 | 1/2009 | Borenstein et al. | |
| 2009/0202614 A1 | 8/2009 | Kaplan et al. | |
| 2009/0214649 A1 | 8/2009 | Gazit et al. | |
| 2009/0232963 A1 | 9/2009 | Kaplan et al. | |
| 2009/0234026 A1 | 9/2009 | Kaplan et al. | |
| 2010/0028451 A1 | 2/2010 | Kaplan et al. | |
| 2010/0046902 A1 | 2/2010 | Kaplan et al. | |
| 2010/0063404 A1 | 3/2010 | Kaplan et al. | |
| 2010/0068740 A1 | 3/2010 | Kaplan et al. | |

(Continued)

FOREIGN PATENT DOCUMENTS

| | | |
|---|---|---|
| JP | 2002-369878 A2 | 12/2002 |
| WO | WO 97/08315 A1 | 3/1997 |

(Continued)

OTHER PUBLICATIONS

International Search Report and Written Opinion for PCT/US2017/059363 dated Feb. 19, 2018.
International Search Report and Written Opinion for PCT/US2017/059322 dated Feb. 20, 2018.
[No Author Listed], Saving Voices with Silk: A new FDA-approved silk-based product may offer hope for long-term voice restoration. Harvard Otolaryngology. 2019 Fall;16(2):4-7.
Acharya et al., Performance evaluation of a silk protein-based matrix for the enzymatic conversion of tyrosine to L-DOPA. Biotechnol J. Feb. 2008;3(2):8 pages.

(Continued)

*Primary Examiner* — Susan T Tran
(74) *Attorney, Agent, or Firm* — Wolf, Greenfield & Sacks, P.C.

(57) ABSTRACT

Various aspects described herein relate to compositions comprising silk fibroin fragments with particular characteristics and/or properties as well as methods of making and using the same.

19 Claims, 15 Drawing Sheets

(56) References Cited

U.S. PATENT DOCUMENTS

| | | |
|---|---|---|
| 2010/0070068 A1 | 3/2010 | Kaplan et al. |
| 2010/0120116 A1 | 5/2010 | Kaplan et al. |
| 2010/0143487 A1 | 6/2010 | Masters |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0279112 A1 | 11/2010 | Kaplan et al. |
| 2010/0317587 A1 | 12/2010 | Chung et al. |
| 2011/0008406 A1 | 1/2011 | Altman et al. |
| 2011/0020409 A1 | 1/2011 | Altman et al. |
| 2011/0046686 A1 | 2/2011 | Kaplan et al. |
| 2011/0076384 A1 | 3/2011 | Cannizzaro et al. |
| 2011/0135697 A1 | 6/2011 | Omenetto et al. |
| 2011/0189292 A1 | 8/2011 | Lebreton et al. |
| 2011/0223153 A1 | 9/2011 | Lu et al. |
| 2012/0052124 A1* | 3/2012 | Kaplan ............ A61K 9/0019 424/489 |
| 2012/0070427 A1 | 3/2012 | Kaplan et al. |
| 2012/0076771 A1 | 3/2012 | Vepari et al. |
| 2012/0121820 A1 | 5/2012 | Kaplan et al. |
| 2012/0129255 A1 | 5/2012 | Kaplan et al. |
| 2012/0171770 A1 | 7/2012 | Numata et al. |
| 2012/0172317 A1 | 7/2012 | Altman et al. |
| 2012/0187591 A1 | 7/2012 | Wang et al. |
| 2012/0223293 A1 | 9/2012 | Borenstein et al. |
| 2013/0158131 A1 | 6/2013 | Kaplan et al. |
| 2013/0177608 A1 | 7/2013 | Kaplan et al. |
| 2014/0135733 A1 | 5/2014 | Hauschild et al. |
| 2014/0287043 A1 | 9/2014 | Kaplan et al. |
| 2014/0308362 A1 | 10/2014 | Bellas et al. |
| 2014/0314817 A1 | 10/2014 | Leisk et al. |
| 2014/0370094 A1* | 12/2014 | Wray ............ A61L 27/36 424/484 |
| 2015/0010630 A1 | 1/2015 | Llamas et al. |
| 2015/0056294 A1* | 2/2015 | Kaplan ............ A61K 9/0019 424/499 |
| 2015/0057685 A1 | 2/2015 | Serban et al. |
| 2015/0086605 A1 | 3/2015 | Mauney et al. |
| 2015/0164117 A1 | 6/2015 | Kaplan et al. |
| 2015/0183841 A1 | 7/2015 | Lo et al. |
| 2015/0238617 A1* | 8/2015 | Kaplan ............ A61K 47/42 424/422 |
| 2016/0038637 A1 | 2/2016 | Lu et al. |
| 2016/0046679 A1 | 2/2016 | Kluge et al. |
| 2018/0050109 A1* | 2/2018 | Kaplan ............ C07K 14/43518 |
| 2018/0272033 A1 | 9/2018 | Hoang et al. |
| 2018/0303742 A1 | 10/2018 | Pavlovic et al. |

FOREIGN PATENT DOCUMENTS

| | | |
|---|---|---|
| WO | WO 01/87267 A1 | 11/2001 |
| WO | WO 2004/001103 A2 | 12/2003 |
| WO | WO 2013/071123 A1 | 5/2013 |
| WO | WO 2014/125505 A1 | 8/2014 |
| WO | WO 2016/145281 A1 | 9/2016 |

OTHER PUBLICATIONS

Altman et al., Silk-based biomaterials. Biomaterials. Feb. 2003;24(3):401-16.

Batzer et al., Enhanced evolutionary PCR using oligonucleotides with inosine at the 3'-terminus. Nucleic Acids Res. Sep. 25, 1991;19(18):5081.

Bayraktar et al,. Silk fibroin as a novel coating material for controlled release of theophylline. Eur J Pharm Biopharm. Aug. 2005;60(3):373-81.

Borzacchiello et al., Rheological Characterization of Vocal Folds after Injection Augmentation in a Preliminary Animal Study. Journal of Bioactive and Compatible Polymers. 2004;19(4):331-41. Epub Jul. 1, 2004.

Carroll et al., A Novel Silk Based Vocal Fold Augmentation Material. The 2017 Fall Voice Conference. The Ritz-Carlton, Washington, DC. PowerPoint Presentation. Oct. 13, 2017:18 slides.

Caton et al., Viscoelasticity of hyaluronan and nonhyaluronan based vocal fold injectables: implications for mucosal versus muscle use. Laryngoscope. Mar. 2007;117(3):516-21.

Chothia et al., Canonical structures for the hypervariable regions of immunoglobulins. J Mol Biol. Aug. 20, 1987;196(4):901-17.

Demura et al., Immobilization of glucose oxidase with Bombyx mori silk fibroin by only stretching treatment and its application to glucose sensor. Biotechnol Bioeng. Jan. 25, 1989;33(5):598-603.

Fattahi et al., 3D Near-Field Electrospinning of Biomaterial Microfibers with Potential for Blended Microfiber-Cell-Loaded Gel Composite Structures. Adv. Healthcare Mater. Oct. 2017;6(19):17 pages.

Guziewica et al., Lyophized silk fibroin hydrogels for the sustained local delivery of therapeutic monoclonal antibodies. Biomaterials. 2011;32:2642-50. Epub Jan. 8, 2011.

Hofmann et al., Silk fibroin as an organic polymer for controlled drug delivery. J Control Release. Mar. 10, 2006;111(1-2):219-27.

Holliger et al., "Diabodies": small bivalent and bispecific antibody fragments. Proc Natl Acad Sci U S A. Jul. 15, 1993;90(14):6444-8.

Jin et al., Water-Stable Silk Films with Reduced β-Sheet Content. Advanced Functional Materials. Aug. 2005;15(8):1241-7.

Kluge et al., Optimizing Molecular Weight of Lyophilized Silk As a Shelf-Stable Source Material. ACS Biomaterials Science & Engineering. Mar. 2016;2:595-605.

Kundu et al., Silk fibroin biomaterials for tissue regenerations. Advanced Drug Delivery Reviews. 2013;65:457-70. Epub Nov. 5, 2012.

Li et al., Silk-based stabilization of biomacromolecules. Journal of Controlled Release. 2015:15 pages. Epub Sep. 25, 2015.

Lu et al., Stabilization of enzymes in silk films. Biomacromolecules. May 11, 2009;10(5):103-242. doi: 10.1021/bm800956n.

Lucas et al., The silk fibroins. Adv Protein Chem. 1958;13:107-242.

Minoura et al., Attachment and growth of cultured fibroblast cells on silk protein matrices. J Biomed Mater Res. Oct. 1995;29(10):1215-21.

Miri, Mechanical characterization of vocal fold tissue: a review study. J Voice. Nov. 2014;28(6):657-67. doi: 10.1016/j.jvoice.2014.03.001. Epub Jul. 5, 2014. Review.

Miyairi et al., Properties of β-Glucosidase Immobilized in Sericin Membrane. Journal of Fermentation Technology. 1978;56(4):303-8.

Murphy et al., Modification of silk fibroin using diazonium coupling chemistry and the effects on hMSC proliferation and differentiation. Biomaterials. Jul. 2008;29(19):2829-38. doi: 10.1016/j.biomaterials.2008.03.039.

Ohtsuka et al., An alternative approach to deoxyoligonucleotides as hybridization probes by insertion of deoxyinosine at ambiguous codon positions. J Biol Chem. Mar. 10, 1985;260(5):2605-8.

Park et al., The effect of heat on skin permeability. Int J Pharm. Jul. 9, 2008;359(1-2):94-103. doi: 10.1016/j.ijpharm.2008.03.032.

Perry et al., Nano- and Micropatterning of Optically Transparent, Mechanically Robust, Biocompatible Silk Fibroin Films. Advanced Materials. 2008;20:3070-2.

Pluckthun, Antibodies from *Escherichia coli*. The Pharmacology of Monoclonal Antibodies. Eds. Rosenburg and Moore. Springer-Verlag: New York. Chapter 11. 1994;113:269-315.

Rajkhowa et al. Ultra-fine silk powder preparation through rotary and ball milling. Powder Technology. Jun. 2008;185(1):87-95.

Rnjak-Kovacina et al., Lyophilized Silk Sponges: A versatile Biomaterial Platform for Soft Tissue Engineering. ACS Biomaterials Science & Engineering. 2015;1:260-70.

Rnjak-Kovacina et al., The Effect of Sterilization on Silk Fibroin Biomaterial Properties. Macromolecular Bioscience. 2015:14 pages. Epub Mar. 11, 2015.

Rockwood et al., Materials fabrication from Bombyx mori silk fibroin. Nature Protocols. 2011;6(10):1612-31.

Rossolini et al., Use of deoxyinosine-containing primers vs degenerate primers for polymerase chain reaction based on ambiguous sequence information. Mol Cell Probes. Apr. 1994;8(2):91-8.

Santin et al., In vitro evaluation of the inflammatory potential of the silk fibroin. J Biomed Mater Res. Sep. 5, 1999;46(3):382-9.

Sofia et al., Functionalized silk-based biomaterials for bone formation. J Biomed Mater Res. Jan. 2001;54(1):139-48.

(56) References Cited

OTHER PUBLICATIONS

Wang et al., In vivo degradation of three-dimensional silk fibroin scaffolds. Biomaterials. Aug.-Sep. 2008;29(24-25):3415-28. doi:10.1016/j.biomaterials.2008.05.002.

Wang et al., Silk nanospheres and microspheres from silk/pva blend films for drug delivery. Biomaterials. Feb. 2010;31(6):1025-35. doi: 10.1016/j.biomaterials.2009.11.002.

Wenk et al., Silk fibroin spheres as a platform for controlled drug delivery. J Control Release. Nov. 24, 2008;132(1):26-34. doi: 10.1016/j.jconrel.2008.08.005.

Wray et al., Effect of processing on silk-based biomaterials: reproducibility and biocompatibility. J Biomed Mater Res B Appl Biomater. Oct. 2011;99(1):89-101. doi: 10.1002/jbm.b.31875. Epub Jun. 21, 2011.

Yucel et al., Vortex-induced injectable silk fibroin hydrogels. Biophys J. Oct. 7, 2009;97(7):2044-50. doi: 10.1016/j.bpj.2009.07.028.

Zapata et al., Engineering linear F(ab')2 fragments for efficient production in *Escherichia coli* and enhanced antiproliferative actiVity. Protein Eng. Oct. 1995;8(10):1057-62.

* cited by examiner

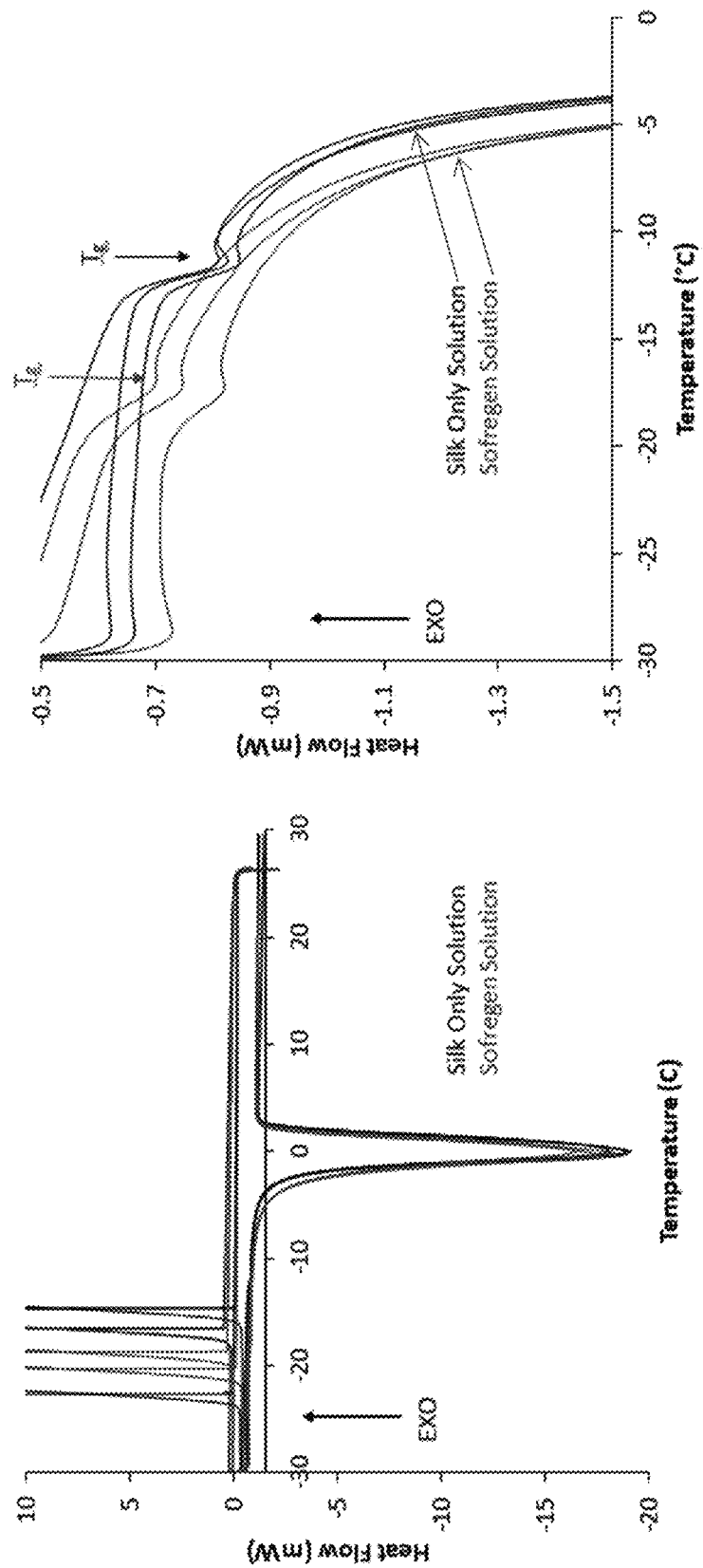

COMPOSITIONS COMPRISING LOW MOLECULAR WEIGHT SILK FIBROIN FRAGMENTS AND PLASTICIZERS

CROSS-REFERENCE TO RELATED APPLICATIONS

This application claims the benefit under 35 U.S.C. § 119(e) of U.S. provisional application No. 62/415,107 filed Oct. 31, 2016; U.S. provisional application No. 62/482,949 filed Apr. 7, 2017; U.S. provisional application No. 62/488,402 filed Apr. 21, 2017; and U.S. provisional application No. 62/571,670 filed Oct. 12, 2017, the contents of each of which are incorporated herein by reference in their entirety.

TECHNICAL FIELD

Various aspects described herein relate to compositions comprising low molecular weight silk fibroin fragments and plasticizers and methods of using the same.

BACKGROUND

Conventional biomaterials or synthetic ceramic or polymeric materials used for soft tissue augmentation include materials such as calcium hydroxylapatite (CaHA) suspended in carboxymethylcellulose, collagen-based or hyaluronic acid-based materials. While these biomaterials provide great soft tissue compatibility, they either degrade fast and thus require repeated treatment every few months or do not match the biomechanics of soft tissue and may lead to the generation of scar tissue or inflammation in the body.

Accordingly, there is a need to develop novel biocompatible compositions that are more effective for soft tissue augmentation, repair, and/or ingrowth, for example, biocompatible compositions that would lend themselves to robust mechanical processing, while also maintaining the flexibility and integrity of the material.

SUMMARY

Embodiments of some aspects described herein are based on, at least in part, the surprising discovery that addition of glycerol at certain concentrations into a silk fibroin solution comprising silk fibroin fragments (e.g., having a weight average molecular weight in a range of about 100 kDa to about 160 kDa), provides a silk/plasticizer (e.g., glycerol) mixture with unexpected structural and/or functional characteristics and/or properties. For example, the silk/plasticizer (e.g., glycerol) mixture can be processed into compositions comprising silk fibroin particles having favorable characteristics. For example, the silk/glycerol mixture may be formed into a solid scaffold (e.g., by lyophilization or freeze-drying), followed by a particle-formation process (e.g., milling), to produce a substantially homogenous population of round silk fibroin particles (see, e.g., FIG. 15A). These particles can be readily converted into injectable/implantable compositions for any suitable biomedical applications such as soft tissue augmentation, regeneration, and/or ingrowth, scaffolding, and/or wound sealing or clotting. In contrast, when using the same particle-formation process, the absence of a plasticizer (e.g., glycerol) in the silk fibroin solution produces a combination of porous silk material and irregular-shaped non-porous crystals (see, e.g., FIG. 15B), which makes them less usable in certain biomedical applications.

As described herein, it was also discovered that addition of a plasticizer (e.g., glycerol) in a silk fibroin solution comprising silk fibroin fragments (e.g., having a weight average molecular weight in a range of about 100 kDa to about 160 kDa), may limit water crystal growth during freezing or lyophilization, and this can aid in the development of silk fibroin-based articles/scaffolds with smaller and more round pores. Yet too high of plasticizer (e.g., glycerol) concentrations could prevent silk fibroin solutions from freezing or lyophilizing (e.g., during the freeze-drying or lyophilizing process) because of changes to the glass transition temperatures of the silk fibroin/plasticizer mixture solution. Thus, it is desirable to balance glycerol concentration such that ease of manufacturing and desired pore size and/or shape can be achieved for a particular application without damaging the integrity of the porous architecture during freeze-drying or lyophilization.

Accordingly, one aspect provided herein relates to a method of producing a population of silk fibroin porous particles. The method comprises: (a) providing a mixture comprising silk fibroin fragments and glycerol, the silk fibroin fragments having a weight average molecular weight ranging from about 100 kDa to about 160 kDa, wherein the glycerol and the silk fibroin fragments are present in a weight ratio of 0.5:100 (glycerol to silk fibroin) to about 20:100 (glycerol to silk fibroin); and (b) forming a population of silk fibroin particles from the mixture. Such a method provides a population of silk fibroin porous particles having an aspect ratio of about 1 to about 3. In some embodiments, at least about 80% or more (including, e.g., at least about 90%, at least about 95%, or more) of the silk fibroin particles in the population are porous and have an aspect ratio in size of about 1 to about 3.

In some embodiments of various aspects described herein, the method further comprises forming a silk fibroin porous scaffold and reducing the silk fibroin porous scaffold into particles. In some embodiments, the silk fibroin porous scaffold can be formed, e.g., by lyophilization or freeze-drying.

In some embodiments involving the methods described above and herein, the glycerol and the silk fibroin fragments are present in a weight ratio (glycerol:silk fibroin) of about 0.5:100 to about 30:100, or in a weight ratio of about 1:100 to about 30:100, or in a weight ratio of about 1:100 to about 10:100. In some embodiments, the glycerol and the silk fibroin fragments are present in a weight ratio (glycerol:silk fibroin) of about 6:100, producing 0.6% (w/v) glycerol and 10% (w/v) silk fibroin fragments of the total solution. The glycerol may be added to the silk fibroin fragments at room temperature after the silk fibroin fragments have been purified and are substantially free of sericin.

In some embodiments, the method described above and herein may further comprise contacting the lyophilized or freeze-dried silk fibroin porous scaffold with a beta-sheet inducing agent. Agents to induce beta-sheet formation in silk fibroin are known in the art. An exemplary beta-sheet inducing agent comprises an alcohol such as methanol.

In some embodiments involving the methods described above and herein, the silk fibroin fragments are prepared by a process comprising degumming silk fibers or silk cocoons at an atmospheric boiling temperature for at least a period of about 60 minutes or more, e.g., more than 60 minutes, more than 70 minutes, more than 80 minutes, more than 90 minutes or longer. In some embodiments involving the compositions described above and herein, the silk fibroin fragments can be prepared by a process comprising degumming silk fibers or silk cocoon at an atmospheric boiling temperature in an aqueous sodium carbonate solution for at least a period of about 60 minutes or more, e.g., more than 60 minutes, more than 70 minutes, more than 80 minutes, more than 90 minutes or longer.

In one set of embodiments involving the methods described herein, the method comprises: (a) lyophilizing or freeze-drying a solution comprising silk fibroin fragments and glycerol, wherein the silk fibroin fragments have a weight average molecular weight in a range of between about 100 kDa and about 160 kDa, and wherein the glycerol and silk fibroin fragments are present in a weight ratio of about 6:100; (b) contacting the lyophilized or freeze-dried silk fibroin/glycerol material with a beta-sheet inducing agent (e.g., an alcohol); and (c) forming one or more silk fibroin particles from the silk fibroin material. The particles may have an average particle size of about 200 μm to about 1000 μm.

Novel compositions comprising silk fibroin fragments and a plasticizer (including, e.g., glycerol), in which the plasticizer and silk fibroin fragments are mixed in certain weight ratios to confer desirable physical characteristics of the solution such that it can be used to produce silk fibroin porous particles, are also provided. For example, in one aspect, provided herein is a composition comprising silk fibroin fragments and glycerol, the silk fibroin fragments having a weight average molecular weight ranging from about 100 kDa to about 160 kDa, wherein the glycerol and the silk fibroin fragments are present in a weight ratio of 0.5:100 to about 30:100; and wherein the composition has a glass transition temperature of equal to or less than about −15° C. In some embodiments, the composition has a relative solubility (e.g., relative to maximum theoretical solubility described below) in a range of about 1% to about 50%.

In some embodiments, the glycerol and the silk fibroin fragments are present in a weight ratio of 1:100 to about 30:100.

In some embodiments, the glycerol and the silk fibroin fragments are present in a weight ratio of 1:100 to about 8:100.

Also provided herein are compositions comprising silk fibroin fragments and a plasticizer, the silk fibroin fragments having a weight average molecular weight ranging from about 100 kDa to about 160 kDa, wherein the plasticizer and the silk fibroin fragments are present in a weight ratio such that the composition, e.g., when sublimed, has a glass transition temperature in a range of about −15° C. and about −25° C.

In some embodiments, the composition has a relative solubility (e.g., relative to maximum theoretical solubility described below) in a range of about 1% to about 50%.

In some embodiments involving the compositions described above and herein, the plasticizer may comprise an alcohol, a sugar, and/or a polyol (e.g., glycerol).

In some embodiments involving the compositions described above and herein, the silk fibroin fragments in the composition (e.g., in any format such as a solution or scaffold) may display a molecular weight distribution characterized in that: no more than about 20% of the total number of the silk fibroin fragments has a molecular weight exceeding about 200 kDa, and at least about 70% of the total number of the silk fibroin fragments has a molecular weight of about 30 kDa to about 170 kDa.

In some embodiments involving the compositions described above and herein, the glycerol and the silk fibroin fragments are present in a weight ratio of about 6:100.

The compositions comprising low molecular weight silk fibroin fragments and glycerol as described herein can be a liquid (e.g., a mixture, a solution) or a non-liquid (e.g., a scaffold). In some embodiments, a composition may be a solution. In some embodiments, a composition may be in a non-liquid form (e.g., a form that is not liquid or that does not flow, e.g., a gel and solid state form such as a sponge), e.g., a silk fibroin scaffold or article. Examples of a silk fibroin scaffold or article can include, but are not limited to, a film, a sheet, a gel or hydrogel, a mesh, a mat, a non-woven mat, a fabric, a scaffold, a tube, a slab or block, a fiber, a particle, a powder, a 3-dimensional construct, an implant, a foam or a sponge, a needle, a lyophilized article, and any combinations thereof.

In some embodiments involving the compositions described above and herein, the non-liquid form (e.g., scaffold) can have a porous structure. For example, the porous structure may be characterized by interconnected pores having an average circle equivalent diameter of about 5 μm to about 60 μm. In one embodiment, the non-liquid form (e.g., scaffold) is a porous particle comprising interconnected pores. In some embodiments, the composition can be dehydrated to form a highly porous matrix with interconnected pores, e.g., having an average pore size of about 20 μm to about 100 μm. This matrix can be reduced (e.g., milled) to form round, porous silk fibroin particles with an average particle size of about 200 μm to about 1000 μm. In some embodiments, these silk fibroin particles form injectable compositions with low extrusion force, making them suitable for soft tissue augmentation, repair, and/or ingrowth.

Another aspect provided herein relates to a silk fibroin scaffold comprising silk fibroin fragments and glycerol, wherein the silk fibroin fragments have a weight average molecular weight ranging from about 100 kDa to about 160 kDa, and wherein the silk fibroin scaffold comprises a porous structure characterized by interconnected pores having an average circle equivalent diameter of about 5 μm to about 60 μm.

In some embodiments involving the silk fibroin scaffold described above and herein, the silk fibroin scaffold may be a lyophilized scaffold. The scaffold can be in any suitable format, e.g., as described above. In some embodiments, the silk fibroin scaffold is a particle, e.g., having an aspect ratio in size in a range of about 1 to about 3.

The silk fibroin particles comprising a plasticizer (e.g., glycerol) described above and herein may comprise any biocompatible material that is suitable for soft tissue argumentation and/or drug delivery in vivo. For example, in some embodiments, the silk fibroin particles comprising a plasticizer (e.g., glycerol) may further comprise a polymer and/or a peptide. The silk fibroin particles comprising a plasticizer (e.g., glycerol) may be porous or non-porous. In some embodiments, the silk fibroin particles comprising a plasticizer (e.g., glycerol) are porous. In these embodiments, the porous particles may have a porous structure characterized by interconnected pores having an average pore size of about 20 μm to about 100 μm. In some embodiments, the porous particles may have an average porosity of at least 90% or higher. The porosity of the particles can be carefully controlled during synthesis and preparation of the material.

The compositions of various aspects described herein can be used for any suitable biomedical applications such as soft tissue augmentation, regeneration, and/or cellular ingrowth, cellular scaffolding, and/or wound sealing or clotting. In some embodiments, the compositions described herein can be also configured for drug delivery, e.g., incorporating an active agent into the compositions or silk fibroin particles as described herein. In some embodiments, the compositions are used as a soft tissue filler (e.g., a dermal filler). In some embodiments, the compositions are used as an injectable implant for vocal fold augmentation. Other applications are also possible.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention.

FIG. 1A shows a molecular weight distribution graph. FIG. 1B shows a picture of SDS-PAGE, where the first lane shows a protein ladder and each of the remaining lanes corresponds to a sample of a composition comprising silk fibroin fragments. FIG. 2A is a chromatogram showing Mv signal (output unit of the refractive index detector) as a function of time and FIG. 2B shows calibration curve of log(Mw) as a function of retention volume.

FIG. 3A is a molecular weight distribution curve for a silk fibroin solution (about 1.25 mg/mL) in its non-reduced/non-denatured state. The mobile phase used was a mixture of about 10% water and about 90% HFIP containing 10 mM trifluoroacetic acid. FIG. 3B is a molecular weight distribution curve for a silk fibroin solution (about 1.25 mg/mL) in its reduced/denatured state. The mobile phase used was a mixture of about 10% SDS/DTT solution and about 90% HFIP containing 10 mM trifluoroacetic acid.

FIG. 4A: The "Silk Only" corresponds to 0% glycerol and the "Silk+Glycerol" corresponds to silk with about 6% (w/w) glycerol. FIG. 4B: silk with different glycerol concentrations as indicated. All glycerol concentrations are expressed in w/w %.

FIG. 5A shows the amount of silk fibroin solubilized as a function of temperature as observed in silk fibroin compositions comprising glycerol at different concentrations. FIG. 5B shows the amount of silk fibroin solubilized at temperature=0° C. as a function of glycerol concentration in silk fibroin compositions.

FIG. 7A shows a FTIR spectrum of a silk fibroin film. FIG. 7B shows a FTIR spectrum of a silk fibroin sponge.

FIGS. 8A-8B show differential scanning calorimetry data for silk fibroin solutions with or without 6% (w/w) glycerol.

FIGS. 10A-10C show the entire cross-section of the silk fibroin bulk material without glycerol (FIG. 10A), a zoomed-in cross section of the corresponding silk fibroin bulk material (FIG. 10B) and silk fibroin particles produced from the corresponding silk fibroin bulk material (FIG. 10C). FIGS. 10D-10F show the entire cross-section of the silk fibroin bulk material with about 6% (w/w) glycerol (FIG. 10D), a zoomed-in cross section of the corresponding silk fibroin bulk material (FIG. 10E), and silk fibroin particles produced from the corresponding silk fibroin bulk material (FIG. 10F). The silk fibroin bulk materials were produced from a silk fibroin solution at a concentration of about 10% (w/v), with or without glycerol at a concentration of about 6% (w/w). The silk fibroin solution (with or without glycerol) was subjected to freeze-drying to fabricate a sponge-like material, which was then immersed in an alcohol (e.g., methanol) to induce β-sheet formation. As compared to the silk fibroin material comprising glycerol (right panels), the silk fibroin material without glycerol (left panels) contained a combination of porous silk fibroin materials and larger non-porous crystals, which, without wishing to be bound by theory, could be attributed to irregularities in freezing. For example, glycerol may delay or slow freezing such that silk fibroin is not exposed to extreme temperatures in such a rapid timeframe.

FIG. 11A: 10% silk fibroin/1% glycerol; FIG. 11B: 10% silk fibroin/3% glycerol; FIG. 11C: 10% silk fibroin/6% glycerol; FIG. 11D: 10% silk fibroin/9% glycerol; FIG. 11E: 10% silk fibroin/12% glycerol; FIG. 11F: 10% silk fibroin/20% glycerol.

DETAILED DESCRIPTION OF EXEMPLARY EMBODIMENTS

Figures 1A, 1B:
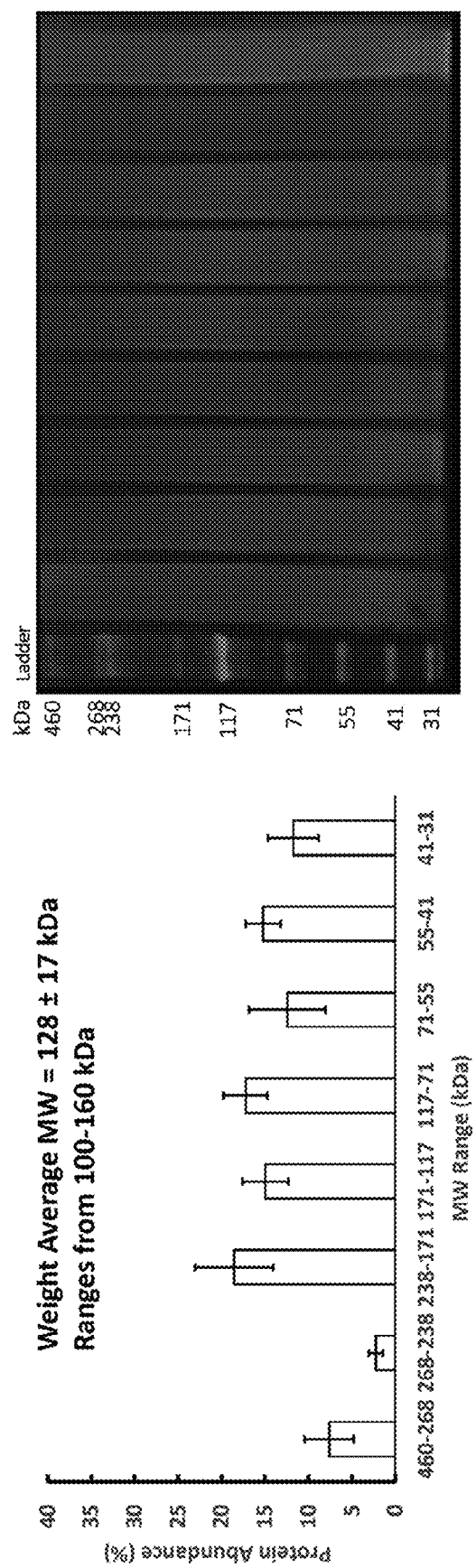
FIGS. 1A-1B show the molecular weight distribution of a solution comprising silk fibroin fragments according to one set of embodiments described herein, as determined by gel electrophoresis/SDS-PAGE.

Some aspects of the present disclosure provide compositions comprising an appropriate combination of a plasticizer and silk fibroin fragments, e.g., fragments of silk fibroin polypeptides, such as silk fibroin fragments having a weight average molecular weight in a range of about 100 kDa to about 160 kDa, as well as methods of making and using such compositions. Such compositions provide desirable structural and/or functional characteristics and/or properties (e.g., lower glass transition temperature and/or lower solubility in an aqueous environment) that facilitates production of a homogenous population of substantially round silk fibroin porous particles, which would otherwise be challenging or difficult to achieve. In addition, such novel compositions can be used for any suitable biomedical applications such as soft tissue augmentation, regeneration, and/or ingrowth, scaffolding, and/or wound sealing or clotting.

Compositions, Scaffolds, or Particles Comprising Silk Fibroin Fragments and a Plasticizer One aspect provided herein relates to a composition comprising silk fibroin fragments and a plasticizer, the silk fibroin fragments having a weight average molecular weight ranging from about 100 kDa to about 160 kDa, wherein the plasticizer and the silk fibroin fragments are present in a weight ratio such that the composition has a glass transition temperature of no more than about −15° C. or lower.

As used herein, the term "silk fibroin fragments" refer to silk fibroin peptide fragments. For example, silk fibroin peptide fragments are fragments of a larger silk fibroin protein (e.g., a full-length silk fibroin protein). In one set of the embodiments of various aspects described herein, the silk fibroin fragments can be, for example, produced by cleavage of amide bonds in the backbone of a larger silk fibroin protein, e.g., a full-length silk fibroin protein.

In some embodiments involving the compositions described herein, the silk fibroin fragments can have a weight average molecular weight of at least about 95 kDa, at least about 100 kDa, at least about 110 kDa, at least about 120 kDa, at least about 130 kDa, at least about 140 kDa, at least about 150 kDa, at least about 155 kDa, or higher. In some embodiments, the silk fibroin fragments may have a weight average molecular weight of equal to or less than about 160 kDa, equal to or less than about 150 kDa, equal to or less than about 140 kDa, equal to or less than about 130 kDa, equal to or less than about 120 kDa, equal to or less than about 110 kDa, or equal to or less than about 100 kDa, or lower. Combinations of the above-referenced ranges are also possible. For example, in some embodiments, the silk fibroin can have a weight average molecular weight in a range of about 95 kDa to about 145 kDa, about 100 kDa to about 140 kDa, about 100 kDa to about 160 kDa, about 105 kDa to about 135 kDa, or about 111 kDa to about 145 kDa. In some embodiments, the silk fibroin fragments have a weight average molecular weight in a range of about 100 kDa and about 140 kDa. In some embodiments, the silk fibroin fragments have a weight average molecular weight in a range of about 111 kDa and about 145 kDa. The weight average molecular weight is one of the ways (including, e.g., number average molecular weight or peak average molecular weight) that can be used to characterize the molecular weight distribution of silk fibroin fragments. Weight Average Molecular Weight is calculated according to equation (1) below:

$$\text{Weight Average Molecular Weight} = \Sigma W_i M_i \quad (1)$$

where $W_i$ is the weight fraction, or the fraction of the total weight represented by each type of molecule, and $M_i$ is the mass of each molecule. The average molecular weights provided herein for silk fibroin fragments can be determined by any known methods in the art, including, e.g., but not limited to, gel electrophoresis (e.g., sodium dodecyl sulfate polyacrylamide gel electrophoresis (SDS-PAGE), size exclusion gel chromatography, mass spectroscopy (e.g., MALDI or ESI), or high performance liquid chromatography (HPLC), refractive index detection (RID), light scattering, or any combinations thereof (e.g., HPLC-RID).

In one set of the embodiments described herein, the weight average molecular weight provided herein for the silk fibroin fragments is determined by gel electrophoresis. For example, Example 4 provides a gel electrophoresis-based method to determine molecular weight distribution of silk fibroin fragments in a solution, which can then be used to determine weight average molecular weight of the silk fibroin fragments in a solution by using equation (1) above.

Figures 3A, 3B:
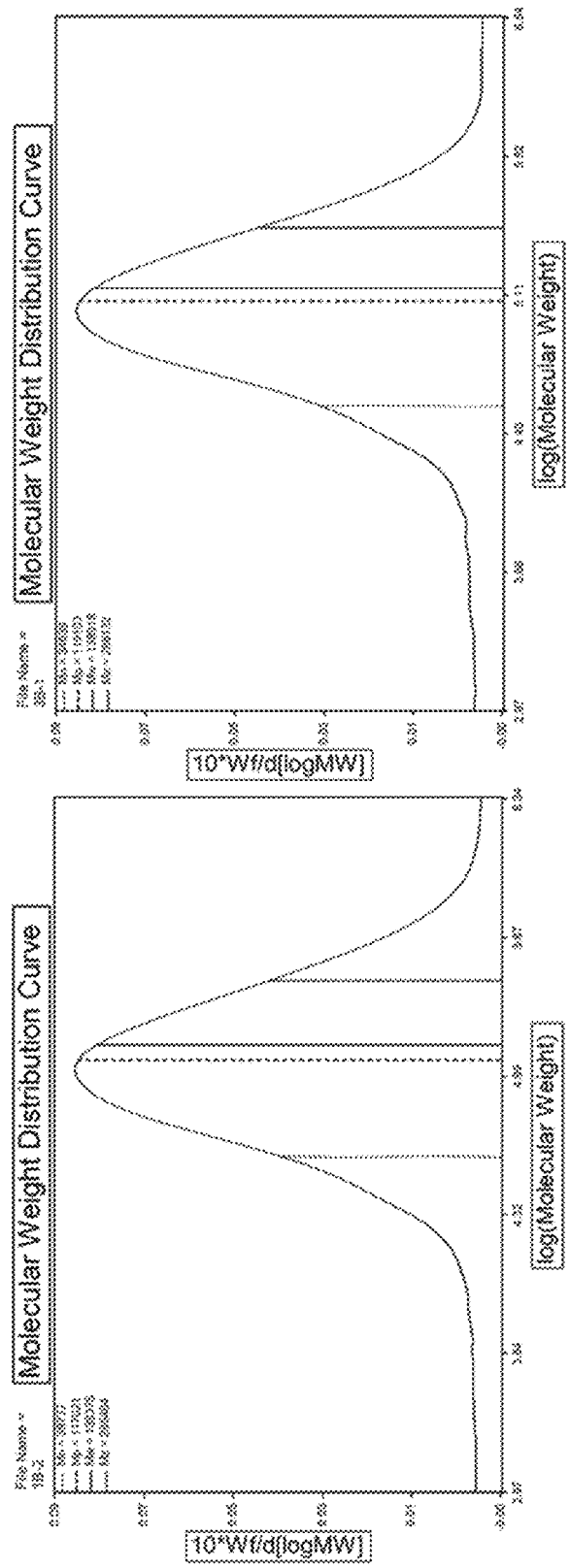
FIGS. 3A-3B show raw HPLC-RID chromatograms of a solution comprising silk fibroin fragments according to one set of embodiments described herein.

In one set of the embodiments described herein, the weight average molecular weight provided for the silk fibroin fragments is determined by high performance liquid chromatography (HPLC)-refractive index detector (RID). The mobile phase used for running a silk fibroin solution through a HPLC column to determine molecular weight distribution may comprise hexafluoroisopropanol (HFIP) containing trifluoroacetic acid. For example, Example 5 provides a HPLC-RID-based method to determine weight average molecular weight of silk fibroin fragments in a solution. In some embodiments, the silk fibroin fragments can be dissolved in water before mixed with a HPLC mobile phase for the molecular weight measurements. In some embodiments, the silk fibroin fragments can be denatured or reduced in a solution comprising a detergent, including, e.g., but limited to sodium dodecyl sulfate (SDS) and/or dithiothreitol (DTT), before it is mixed with a HPLC mobile phase for the molecular weight measurements. Typically, the HPLC-RID method fits molecular weight measurements into a normal distribution curve, e.g., as shown in FIGS. 3A and 3B, to determine weight average molecular weight.

In some embodiments involving the compositions described herein, the silk fibroin fragments in the composition (e.g., in any format such as a solution or scaffold) may display a molecular weight distribution characterized in that: no more than about 20% (including, e.g., no more than about 15%, no more than about 10%, no more than about 5%, no more than about 3%, including about 0%) of the total number of the silk fibroin fragments has a molecular weight exceeding about 200 kDa or higher (e.g., exceeding about 210 kDa, about 220 kDa, about 230 kDa, about 240 kDa, about 250 kDa, about 260 kDa, about 270 kDa, about 280 kDa, about 290 kDa, about 300 kDa or higher). In some embodiments, at least about 0.5%, at least about 1%, including, e.g., at least about 3%, at least about 5%, at least about 10%, at least about 15%, at least about 20%, of the total number of the silk fibroin fragments has a molecular weight exceeding about 200 kDa or higher (e.g., exceeding about 210 kDa, about 220 kDa, about 230 kDa, about 240 kDa, about 250 kDa, about 260 kDa, about 270 kDa, about 280 kDa, about 290 kDa, about 300 kDa or higher). Combinations of the above-referenced ranges are also possible. For example, about 1% to about 10% of the total number of the silk fibroin fragments has a molecular weight exceeding about 270 kDa or higher.

In some embodiments involving the compositions described herein where the silk fibroin fragments that have a molecular weight exceeding about 200 kDa or higher (e.g., exceeding about 210 kDa, about 220 kDa, about 230 kDa, about 240 kDa, about 250 kDa, about 260 kDa, about 270 kDa, about 280 kDa, about 290 kDa, about 300 kDa or higher) are present in any combination of the above-referenced ranges, at least about 60% (including, e.g., at least about 65%, at least about 70%, at least about 75%, at least about 80%, at least about 85%, at least about 90%, or at least about 98%, including 100%) of the total number of the silk fibroin fragments has a molecular weight of about 30 kDa to about 170 kDa. In some embodiments, no more than about 99%, including, e.g., no more than about 95%, no more than about 90%, no more than about 85%, no more than about 80%, no more than about 75%, or lower, of the total number of the silk fibroin fragments has a molecular weight of about 30 kDa to about 170 kDa. Combinations of the above-referenced ranges are also possible. For example, in some embodiments, about 60% to about 80% of the total number of the silk fibroin fragments has a molecular weight of about 30 kDa to about 170 kDa.

In some embodiments involving the compositions described above and herein (including combinations of the above-referenced molecular weight distribution of silk fibroin fragments), at least about 70% (including, e.g., at least about 75%, at least about 80%, at least about 85%, at least about 90%, or at least about 98%, including 100%) of the total number of the silk fibroin fragments has a molecular weight of about 30 kDa to about 240 kDa. In some embodiments, no more than about 99%, including, e.g., no more than about 95%, no more than about 90%, no more than about 85%, no more than about 80% or lower, of the total number of the silk fibroin fragments has a molecular weight of about 30 kDa to about 240 kDa. Combinations of the above-referenced ranges are also possible. For example, in some embodiments, about 80% to about 95% of the total number of the silk fibroin fragments has a molecular weight of about 30 kDa to about 240 kDa.

In some embodiments involving the compositions described above and herein (including combinations of the above-referenced molecular weight distribution of silk fibroin fragments), the silk fibroin fragments in the composition (e.g., in any format such as a solution or scaffold) may display a molecular weight distribution characterized in that: at least about 20%, including, e.g., at least about 30%, at least about 40%, at least about 50%, at least about 60%, at least about 70%, at least about 80%, at least about 90%, at least about 95% or above, of the total number of the silk fibroin fragments have a molecular weight of about 25 kDa to about 60 kDa. In some embodiments, no more than about 95%, including, e.g., no more than about 90%, no more than about 80%, no more than about 70%, no more than about 60%, no more than about 50%, no more than about 40%, no more than 30% or lower, of the total number of the silk fibroin fragments have a molecular weight of about 25 kDa to about 60 kDa. Combinations of the above-referenced ranges are also possible. For example, in some embodiments, about 20% to about 30% of the total number of the silk fibroin fragments have a molecular weight of about 25 kDa to about 60 kDa.

In some embodiments involving the compositions described above and herein (including combinations of the above-referenced molecular weight distribution of silk fibroin fragments), the silk fibroin fragments in the composition (e.g., in any format such as a solution or scaffold) may display a molecular weight distribution characterized in that: at least about 20%, including, e.g., at least about 25%, at least about 30%, at least about 40%, at least about 50%, at least about 60%, at least about 70%, at least about 80%, at least about 90%, at least about 95% or above, of the total number of the silk fibroin fragments have a molecular weight of about 25 kDa to about 80 kDa. In some embodiments, no more than about 95%, including, e.g., no more than about 90%, no more than about 80%, no more than about 70%, no more than about 60%, no more than about 50%, no more than about 45%, or no more than about 40% or lower, of the total number of the silk fibroin fragments have a molecular weight of about 25 kDa to about 80 kDa. Combinations of the above-referenced ranges are also possible. For example, in some embodiments, about 25% to about 45% or about 20% to about 50% of the total number of the silk fibroin fragments have a molecular weight of about 25 kDa to about 80 kDa.

In some embodiments involving the compositions described above and herein (including combinations of the above-referenced molecular weight distribution of silk fibroin fragments), the silk fibroin fragments in the composition (e.g., in any format such as a solution or scaffold) may display a molecular weight distribution characterized in that: at least about 40%, including, e.g., at least about 45%, at least about 50%, at least about 60%, at least about 70%, at least about 80%, at least about 90%, at least about 95% or above, of the total number of the silk fibroin fragments have a molecular weight of about 25 kDa to about 130 kDa. In some embodiments, no more than about 95%, including, e.g., no more than about 90%, no more than about 80%, no more than about 70%, no more than 65%, no more than about 60% or lower, of the total number of the silk fibroin fragments have a molecular weight of about 25 kDa to about 130 kDa. Combinations of the above-referenced ranges are also possible. For example, in some embodiments, about 45% to about 65% or about 40% or about 70% of the total number of the silk fibroin fragments have a molecular weight of about 25 kDa to about 130 kDa.

The total number of the silk fibroin fragments in any embodiments of various aspects described above and herein can be determined, e.g., by gel electrophoresis such as SDS-PAGE, followed by protein staining and image quantification of protein stain intensity.

In accordance with various embodiments involving the compositions described herein, the silk fibroin fragments having a weight average molecular weight in a range of about 100 kDa and about 160 kDa (or any of the above-referenced ranges) are distinct from so-called "hydrolyzed silk." Hydrolyzed silk is generally produced by hydrolyzing or breaking down silk proteins into smaller peptide chains, e.g., with a molecular weight of no more than about 2 kDa, and/or constituent amino acids such as glycine, alanine and serine. Accordingly, the term "hydrolyzed silk" as used herein refers to silk peptide chains or amino acids with a molecular weight of less than 2 kDa, less than 1 kDa, less than 500 Da or smaller.

In one set of the embodiments involving the compositions described herein, the plasticizer and the silk fibroin fragments are present in a weight ratio such that the composition, e.g., when sublimed, exhibit a glass transition temperature ($T_g$) of no more than about −15° C. or lower, including, e.g., no more than about −16° C., no more than about −17° C., no more than about −18° C., no more than about −19° C., no more than about −20° C., no more than about −25° C., no more than about −30° C., or lower. In some embodiments, the glass transition temperature ($T_g$) of the compositions described herein is at least about −40° C., including, e.g., at least about −35° C., at least about −30° C., at least about −25° C., at least about −20° C., or higher. Combinations of the above-referenced ranges are also possible. For example, in some embodiments, the glass transition temperature ($T_g$) of the compositions described herein is about −35° C. to about −15° C. In some embodiments, the glass transition temperature ($T_g$) of the compositions described herein is about −30° C. to about −18° C. In some embodiments, the glass transition temperature ($T_g$) of the compositions described herein is about −25° C. to about −18° C. In some embodiments, the glass transition temperature ($T_g$) of the compositions described herein is about −25° C. to about −15° C. In some embodiments, the glass transition temperature ($T_g$) of the compositions described herein is about −19° C. to about −17° C. In some embodiments, the glass transition temperature ($T_g$) of the compositions described herein is about −19° C. to about −17.5° C. In some embodiments, the glass transition temperature ($T_g$) of the compositions described herein is about −18.5° C. to about −18.0° C.

The glass transition temperature ($T_g$) is one of the important characteristics of the compositions described herein. The $T_g$ of a material is the point below which an amorphous solid goes from being ductile to brittle. The $T_g$ can be measured, e.g., using differential scanning calorimetry (DSC). Addition of a plasticizer at an appropriate concentration to a "low molecular weight (LMW) silk fibroin solution" (e.g., in which silk fibroin fragments have any of the above-referenced weight-average molecular weight and/or any combination of the above-referenced molecular weight distribution) can change the $T_g$ of the resulting silk fibroin solution comprising a plasticizer. The shift in $T_g$ as observed in a LMW silk fibroin solution comprising a plasticizer indicates that the material is more malleable, e.g., less brittle than those low molecular weight solutions previously described, e.g., in Kluge, J. A. et al. 2016. *ACS Biomaterials Science & Engineering*, 2, 595-605. This shift to a colder glass transition temperature means that at a colder temperature, the compositions described herein can maintain the malleable phase until the lower $T_g$ is reached. Unlike the LMW silk fibroin solutions without glycerol, the compositions described herein can be exposed to colder temperatures before they are transformed into "glassy" materials or crystalline materials. Thus, the resulting compositions described herein are more rubbery than similar materials produced from the LMW silk fibroin solutions without glycerol. Such physical properties provide the capability of reducing (e.g., milling) the freeze-dried compositions described herein to form rounder and more uniform particles than silk fibroin materials without glycerol (see Example 9).

The weight ratio of the plasticizer to the silk fibroin fragments in a mixture in any of the aspects involving the compositions and methods described herein is adjusted such that the composition has a glass transition temperature ($T_g$) of any combination of the above-referenced ranges. The weight ratio may vary with a plasticizer (e.g., glycerol vs. sorbitol) or combinations of plasticizers (e.g., but not limited to sugars, and polyols) selected to achieve a desired $T_g$ of the mixture. The $T_g$ of a silk fibroin/plasticizer mixture generally depends on individual $T_g$'s for each component. By way of example only, a Couchman-Karasz equation can model $T_g$ of basic, amorphous mixtures, and is a general depiction of how entropy of individual components may affect the combined entropy of a mixture. Using glycerol as an example of a plasticizer, glycerol has a $T_g$ of about −93.15° C. An example silk fibroin solution has a $T_g$ of about −11° C. As glycerol is added to the silk fibroin solution, the $T_g$ of the silk fibroin/glycerol mixture will shift towards that of glycerol. Typically, the larger the difference in $T_g$ between the components, the greater the rate of change in $T_g$ of the mixture as the amount of the plasticizer added increases. In some embodiments, protein dynamics and/or interactions with plasticizers and water molecules may be taken into account for modeling the $T_g$ of a mixture.

In one set of the embodiments involving the compositions described above and herein, the plasticizer and the silk fibroin fragments are present in a weight ratio such that the composition has a relative solubility (e.g., relative to maximum theoretical solubility described herein) of no more than 60% or less, including, e.g., no more than about 50%, no more than about 40%, no more than about 30%, no more than about 20%, no more than about 10%, no more than about 5%, or lower. In some embodiments, the compositions described herein have a relative solubility (e.g., relative to maximum theoretical solubility described herein) of at least about 1%, at least about 5%, at least about 10%, at least about 20%, at least about 30%, at least about 40%, at least about 50% or higher. Combinations of the above-referenced ranges are also possible. By way of example only, in some embodiments, the compositions described herein can have a relative solubility (e.g., relative to maximum theoretical solubility described herein) in a range of about 1% to about 50%. The relative solubility of the composition is measured as follows. A test sample is immersed in a specified amount of water (e.g., deionized water) such that a 100 mL (or 100 µL) of water (e.g., deionized water) is added for every 5 grams (or 5 milligrams) of total mass of silk fibroin present in the test sample. Thus, the maximum theoretical solubility of silk fibroin for the test sample is 5% w/v (i.e., 5 g silk fibroin per 100 mL water; or 5 mg silk fibroin per 100 µL water). The relative solubility of the test sample is the amount of silk fibroin dissolved in the specified amount of water (e.g., deionized water) relative to the maximum theoretical solubility as discussed above. In some embodiments, the solubility assay is performed in deionized water at a temperature in range of about 5° C. to about 45° C. and at a pH in a range of about 6.0 to about 7.0. In some embodiments, the above-referenced values or ranges provided for the relative solubility of the compositions described herein are determined using the method as described in Example 8. The more soluble the silk fibroin composition is in an aqueous solution, the lower the contact angle and the higher hydrophilicity of the composition.

In one set of the embodiments involving the compositions and the methods described herein, the plasticizer and the silk fibroin fragments are present in a weight ratio (with respect to each other) of no more than about 30:100 or lower, including, e.g., no more than about 20:100, no more than about 15:100, no more than about 12:100, no more than about 10:100, no more than about 8:100, no more than about 6:100, or lower. In some embodiments, the plasticizer and the silk fibroin fragments are present in a weight ratio of at least about 0.5:100, at least about 1:100, at least about 2:100, at least about 3:100, at least about 4:100, at least about 5:100, at least about 6:100, at least about 7:100, at least about 8:100, at least about 9:100, at least about 10:100, at least about 20:100, at least about 25:100, or higher. Combinations of the above-referenced ranges are also possible. For example, in some embodiments, the plasticizer and the silk fibroin fragments may be present in a weight ratio in a rage of about 0.5:100 to about 30:100, in a range of about 0.5:100 to about 20:100, in a range of about 0.5:100 to about 10:100, in a range of about 0.5:100 to about 8:100, in a range of about 0.5:100 to about 6:100. In some embodiments, the plasticizer and the silk fibroin fragments may be present in a weight ratio in a range of about 1:100 to about 30:100, in a range of about 1:100 to about 20:100, in a range of about 1:100 to about 10:100, in a range of about 1:100 to about 8:100, in a range of about 1:100 to about 6:100. In one set of the embodiments described herein, the plasticizer and the silk fibroin fragments may be present in a weight ratio of about 6:100.

As described above, addition of a plasticizer to silk fibroin fragments can decrease the $T_g$ of the resulting composition. The resulting silk fibroin/plasticizer silk fibroin compositions can be used to form different articles or scaffolds for various biomedical applications, including, e.g., but not limited to soft tissue augmentation and/or drug delivery. For example, to create freeze-dried silk fibroin scaffolds/sponges, it is desirable to have silk-plasticizer solutions at a temperature below $T_g$ prior to sublimation. If this condition is not met, freeze-dried scaffolds may collapse during the sublimation step, corrupting the integrity of pores and scaffold architecture. Too high of a plasticizer concentration could prevent silk fibroin solutions from freezing because the $T_g$ is too low to be reached. However, appropriate addition of a plasticizer may be beneficial in that a plasticizer (e.g., glycerol) limits water crystal growth during freezing, and this can aid in the development of scaffolds/sponges with smaller and more round pores, for example, as shown in FIGS. 12A-13C. Therefore, the weight ratio of a plasticizer and silk fibroin fragments in the compositions described herein should be balanced for a particular application, e.g., proper pore size and/or shape in silk fibroin scaffold compositions configured for soft tissue augmentation without damaging the integrity of the porous architecture during freeze-drying or lyophilization.

Any suitable plasticizer that can decrease the $T_g$ and/or solubility of a silk fibroin solution and result in the formation of the scaffold characteristics described herein can be used in the compositions and methods described herein. Examples of such a plasticizer include, but are not limited to alcohols containing at least one hydroxyl group (including, e.g., methanol; ethanol; propanol isomers, e.g., 1-propanol, isopropyl alcohol; butanol isomers, e.g., n-butanol, sec-butanol, isobutanol, tert-butanol; pentanol isomers (amyl alcohol), e.g., n-pentanol, isobutyl carbinol, active amyl alcohol, tertiary butyl carbinol, 3-pentanol, methyl (n) propyl carbinol, methyl isopropyl carbinol, dimethyl ethyl carbinol; hexanol, e.g., n-hexanol and related isomers; heptanol and related isomers; octanol and related isomers; nonanol and related isomers; and decanol and related isomers); sugars or simple sugars (including, e.g., sucrose, glucose; fructose; ribose; galactose; maltose; lactose; triose; tetrose; pentose; hexose; trehalose; and any other monosaccharides, disaccharides, oligosaccharides, and polysaccharides); polyols containing multiple hydroxyl groups (including, e.g., diols; vicinal diols (hydroxyl groups attached to adjacent atoms: examples include but are not limited to: propane-1,2-diol; ethylene glycol; propylene glycol); 1,3 diols (e.g., propane-1,3-diol; 2,2-dimethyl-1,3-propanediol; 1,3 butanediol; 1,4 diols (e.g., 1,4-butanediol, 1,4-pentanediol); 1,5 diols and longer; triols (e.g., Glycerol, Benzenetriol, Pyrogallol, 1,2,6 Hexanetriol, 1,3,5-pentanetriol; Phenols (e.g., hydroquinone, resorcinol, meta-cresol, eugenol, thymol, pyrogallol); sugar alcohols or polyhydric alcohols; arabitol; erythritol; fucitol; galactitol; iditol; inositol; isomalt; lactitol; maltitol; maltotetraitol; maltotriitol; mannitol; ribitol (adonitol); sorbitol; threitol; volemitol; xylitol; and any combinations thereof.

In one set of the embodiments involving the compositions and/or method described herein, the plasticizer is glycerol. In these embodiments, glycerol may be mixed with silk fibroin fragments in any of the above-referenced weight ratio ranges. For example, in some embodiments, glycerol may be mixed with silk fibroin fragments in a weight ratio (glycerol to silk fibroin fragments) ranging from about 0.5:100 to about 30:100, from about 0.5:100 to about 20:100, from about 0.5:100 to about 10:100, from about 0.5:100 to about 8:100, or from about 0.5:100 to about 6:100. In some embodiments, glycerol and the silk fibroin fragments may be present in a weight ratio ranging from about 1:100 to about 20:100, from about 1:100 to about 10:100, from about 1:100 to about 8:100, from about 1:100 to about 6:100. In one set of the embodiments described herein, the glycerol and the silk fibroin fragments may be present in a weight ratio of about 6:100. Table 1 in Example 6 summarizes the physical characteristics of an embodiment of the compositions described herein, in which glycerol and silk fibroin fragments were present in a weight ratio of about 6:100. While there are previous reports on addition of glycerol to silk fibroin solutions, appropriate combinations of low concentration of glycerol and low molecular weight silk fibroin fragments to achieve a material with the advantageous properties described herein were not disclosed, e.g., materials with a sufficiently low $T_g$ such that the material upon freeze-drying is rubbery enough to allow further downstream processing, such as milling to form rounder and more uniform particles.

Accordingly, in one set of embodiments described herein, a composition comprises silk fibroin fragments and glycerol, the silk fibroin fragments having a weight average molecular weight ranging from about 100 kDa to about 160 kDa (including any of the above-referenced ranges), wherein the glycerol and the silk fibroin fragments are present in a weight ratio of about 0.5:100 to about 10:100 (including any of the above-referenced ranges). The composition may have a glass transition temperature of any of the above-referenced values or ranges, for example, a glass transition temperature of less than about −15° C. Additionally or alternatively, the composition may have a relative solubility of any of the above-referenced values or ranges, for example, a relative solubility (e.g., relative to maximum theoretical solubility described below) in a range of about 1% to about 50%.

In some embodiments, the silk fibroin fragments are substantially depleted of its native sericin content (e.g., about 5% (w/w) or less residual sericin in the final extracted silk fibroin). Alternatively, higher concentrations of residual sericin can be left on the silk following extraction or the extraction step can be omitted. In some embodiments, the silk fibroin fragments have, e.g., about 0.1% (w/w) residual sericin (or more), about 1% (w/w) residual sericin (or more), about 2% (w/w) residual sericin (or more), about 3% (w/w) residual sericin (or more), about 4% (w/w) (or more), or about 5% (w/w) residual sericin (or more). In some embodiments, the silk fibroin fragments have, e.g., at most 1% (w/w) residual sericin, at most 2% (w/w) residual sericin, at most 3% (w/w) residual sericin, at most 4% (w/w), or at most 5% (w/w) residual sericin. Combinations of the above-referenced ranges are also possible. In some other embodiments, the silk fibroin fragments have, e.g., about 1% (w/w) to about 2% (w/w) residual sericin, about 1% (w/w) to about 3% (w/w) residual sericin, about 1% (w/w) to about 4% (w/w), or about 1% (w/w) to about 5% (w/w) residual sericin. In some embodiments, the silk fibroin fragments are entirely free of its native sericin content. As used herein, the term "entirely free" means that within the detection range of the instrument or process being used, the substance cannot be detected or its presence cannot be confirmed. In some embodiments, the silk fibroin is essentially free of its native sericin content. As used herein, the term "essentially free"

means that only trace amounts of the substance can be detected, is present in an amount that is below detection, or is absent.

Silk fibroin is a particularly appealing biopolymer candidate to be used for various embodiments described herein, e.g., because of its versatile processing, e.g., all-aqueous processing (Sofia et al., 54 J. Biomed. Mater. Res. 139 (2001); Perry et al., 20 Adv. Mater. 3070-72 (2008)), relatively easy functionalization (Murphy et al., 29 Biomat. 2829-38 (2008)), and biocompatibility (Santin et al., 46 J. Biomed. Mater. Res. 382-9 (1999)). For example, silk has been approved by U.S. Food and Drug Administration as a tissue engineering scaffold in human implants. See Altman et al., 24 Biomaterials: 401 (2003).

As used herein, the term "silk fibroin" includes silkworm fibroin and insect or spider silk protein. See e.g., Lucas et al., 13 Adv. Protein Chem. 107 (1958) which is incorporated herein by reference. Any type of silk fibroin can be used in different embodiments described herein. Silk fibroin produced by silkworms, such as *Bombyx mori*, is the most common and represents an earth-friendly, renewable resource. For instance, silk fibroin may be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used.

In any one of the embodiments described herein, silk fibroin can be modified for desired mechanical or chemical properties. One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interactions. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711.

In some embodiments, silk fibroin can be chemically modified to enhance hydrophilicity (or hydrophobicity), making it more or less hydrophilic in the presence of media. Hydrophilic silk fibroin particles are more likely to take up aqueous media and swell after injection into a tissue to be treated compared to silk fibroin particles that are less hydrophilic.

The compositions comprising low molecular weight silk fibroin fragments as described above and herein and a plasticizer (e.g., glycerol) can be a solution or a scaffold. In some embodiments, the compositions may be a solution. In some embodiments, the compositions may be in a non-liquid form, e.g., a silk fibroin scaffold or article or gel. Examples of a silk fibroin scaffold or article can include, but are not limited to, a film, a sheet, a gel or hydrogel, a mesh, a mat, a non-woven mat, a fabric, a scaffold, a tube, a slab or block, a fiber, a particle, a powder, a 3-dimensional construct, an implant, a foam or a sponge, a needle, a lyophilized article, and any combinations thereof.

In some embodiments involving the compositions described above and herein, the non-liquid form (e.g., scaffold) can comprise a porous structure, e.g., to mimic the structural morphology of a native tissue, to modulate the degradation rate/volume retention rate of the particles (e.g., silk fibroin particles), to provide void spaces for cells to populate and proliferate therein, and/or to module modulate release profile of an active agent embedded therein, if any. As used herein, the terms "porous" and "porosity" are generally used to describe a structure having an interconnected network of pores or void spaces (which can, for example, be openings, interstitial spaces or other channels) throughout its volume. The term "porosity" is a measure of void spaces in a material, and is a fraction of volume of voids over the total volume, as a percentage between 0 and 100% (or between 0 and 1).

The porous structure can have pores and/or cervices that are accessible to cells, media, and/or solutes. The pores can be at the surface of the non-liquid form (e.g., scaffold) compositions or scaffolds comprising low molecular weight silk fibroin fragments and a plasticizer as described herein ("silk fibroin non-liquid form (e.g., scaffold)"), and/or within the bulk structure of the silk fibroin non-liquid form (e.g., scaffold). In some embodiments, the silk fibroin non-liquid form (e.g., scaffold) may have an average porosity of at least about 1%, at least about 3%, at least about 5%, at least about 10%, at least about 15%, at least about 20%, at least about 30%, at least about 40%, at least about 50%, at least about 60%, at least about 70%, at least about 80%, at least about 90%, at least about 93%, at least about 95%, at least about 97%, or higher. In some embodiments, the silk fibroin non-liquid form (e.g., scaffold) may have an average porosity of less than or equal to about 99%, less than or equal to about 95%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, less than or equal to about 15%, less than or equal to about 10%, less than or equal to about 5%, less than or equal to about 3%, or less than or equal to about 1%. Combinations of the above-referenced ranges are also possible. In some embodiments, the average porosity may range from about 50% to about 99%, about 70% to about 99%, or from about 80% to about 98%. In some embodiments, the average porosity of a silk fibroin non-liquid form (e.g., scaffold) may have an average porosity of about 70% to about 90%, meaning that about 70% to about 90% of the total volume of the silk fibroin non-liquid form (e.g., scaffold) is void space and about 10% to about 30% of the total volume of the silk fibroin non-liquid form (e.g., scaffold) comprises silk fibroin fragments. The pore size and average porosity values can be quantified using conventional methods and models known to those of skill in the art. For example, the pore size and average porosity can be measured by standardized techniques, such as mercury porosimetry, nitrogen adsorption, and/or SEM analysis of cross-sections of a porous material. Solvent infiltration (e.g., with low surface tension fluid such as hexane) can also be used to determine material porosity.

For example, a porous matrix can be immersed in a selected solvent or fluid of a known volume until the porous matrix is saturated with the solvent or fluid. The change in the fluid volume is the void volume of the porous matrix.

The pores of the silk fibroin non-liquid form (e.g., scaffold) can be of any suitable shape, e.g., circular, elliptical, or polygonal. The porous silk fibroin non-liquid form (e.g., scaffold) can have a pore size (e.g., an average pore size) of less than or equal to about 100 µm, less than or equal to about 95 µm, less than or equal to about 90 µm, less than or equal to about 85 µm, less than or equal to about 80 µm, less than or equal to about 75 µm, less than or equal to about 70 µm, less than or equal to about 65 µm, less than or equal to about 60 µm, less than or equal to about 55 µm, less than or equal to about 50 µm, less than or equal to about 45 µm, less than or equal to about 40 µm, less than or equal to about 35 µm, less than or equal to about 30 µm, less than or equal to about 25 µm, less than or equal to about 20 µm, less than about 15 µm, less than about 10 µm, or lower. In some embodiments, the porous silk fibroin non-liquid form (e.g., scaffold) may have a pore size (e.g., an average pore size) of at least about 5 µm, at least about 10 µm, at least about 15 µm, at least about 20 µm, at least about 25 µm, at least about 30 µm, at least about 35 µm, at least about 40 µm, at least about 45 µm, at least about 50 µm, at least about 55 µm, at least about 60 µm, at least about 65 µm, at least about 70 µm, at least about 75 µm, at least about 80 µm, at least about 85 µm, at least about 90 µm, at least about 95 µm, or at least about 100 µm, or higher. Combinations of the above-referenced ranges are also possible. In some embodiments, the porous silk fibroin non-liquid form (e.g., scaffold) may have a pore size (e.g., an average pore size) of about 5 µm to about 100 µm, or about 5 µm to about 60 µm, or about 10 µm to about 60 µm, or about 30 µm to about 50 µm. The term "pore size" as used herein refers to a dimension of a pore. In some embodiments, the pore size can refer to the longest dimension of a pore, e.g., a diameter of a pore having a circular cross section, or the length of the longest cross-sectional chord that can be constructed across a pore having a non-circular cross-section. In other embodiments, the pore size can refer to the shortest dimension of a pore. In some embodiments, the pore size can refer to the circle equivalent diameter. A "circle equivalent diameter" (also known as "area equivalent diameter") is the diameter of a circular pore that gives the same cross-section area as an equivalent pore (e.g., an equivalent non-circular pore) present in a test sample. The cross-section area of a pore in a test sample can be determined, e.g., by SEM analysis of cross-sections of a porous scaffold to determine the cross-section area ($A_{pore}$) of pores and then determine the circle equivalent diameter ($D_{circular}$) using the equation: $D_{circular}=(4A_{pore}/\pi)^{1/2}$.

As used herein, the term "average pore size" refers to an average or mean value of a size distribution of a population of pores based on measurements of a selected dimension of a pore (e.g., the longest dimension of a pore such as diameter, or a characteristic length of a pore such as circle equivalent diameter).

In some embodiments, the porous structure may be characterized by interconnected pores having an average circle equivalent diameter of any of the above-referenced pore size value or ranges. For example, in some embodiments, the pores may have an average circle equivalent diameter of about 5 µm to about 60 µm.

In some embodiments involving a silk fibroin non-liquid form (e.g., scaffold) described herein, the porous structure may be characterized by no more than 10% (including, e.g., no more than about 9%, no more than about 8%, no more than about 7%, no more than about 6%, no more than about 5% or lower) of interconnected pores having an average pore size (e.g., an average circle equivalent diameter) of about 100 µm or greater.

In some embodiments involving a silk fibroin non-liquid form (e.g., scaffold) described herein, the porous structure may be characterized by no more than 15% (including, e.g., no more than about 14%, no more than about 13%, no more than 12%, no more than 11%, no more than 10%, no more than about 9%, no more than about 8%, no more than about 7%, no more than about 6%, no more than about 5% or lower) of interconnected pores having an average pore size (e.g., an average circle equivalent diameter) of about 75 µm or greater.

In some embodiments involving a silk fibroin non-liquid form (e.g., scaffold) described herein, the porous structure may be characterized by at least about 50% (including, e.g., at least about 60%, at least about 70%, at least about 80%, at least about 90%, or above) of interconnected pores having an average pore size (e.g., an average circle equivalent diameter) of about 5 µm to about 75 µm, or about 15 µm to about 60 µm, or about 15 µm to about 55 µm.

In some embodiments involving a silk fibroin non-liquid form (e.g., scaffold) described herein, at least about 40% (including, e.g., at least about 50%, at least about 60%, at least about 70%, at least about 80%, at least about 90% or more and up to 100%) of the pores have an aspect ratio of about 1.0 to about 3.

In some embodiments involving a silk fibroin non-liquid form (e.g., scaffold) described herein, no more than about 10% (including, e.g., no more than about 9%, no more than about 8%, no more than about 7%, no more than about 6%, no more than about 5%, or lower) of the pores have an aspect ratio of at least about 2.5 or higher (e.g., including, e.g., at least about 3.0, at least about 3.5, at least about 4.0, or higher).

In some embodiments involving a silk fibroin non-liquid form (e.g., scaffold) described herein, the pores of the particles (e.g., silk fibroin particles) have an average aspect ratio of at least about 1.5, at least about 1.6, at least about 1.7, at least about 1.8, at least about 1.9, at least about 2.0. In some embodiments, the pores of the particles (e.g., silk fibroin particles) have an average aspect ratio of no more than about 2.5, no more than about 2.4, no more than about 2.3, no more than about 2.2, no more than about 2.1, no more than about 2.0, no more than about 1.9, no more than about 1.8, no more than about 1.7, no more than about 1.6, or lower. Combinations of the above-referenced ranges are possible. For example, in some embodiments, the pores of the particles (e.g., silk fibroin particles) have any average aspect ratio of about 1.5 to about 2.5, or about 1.8 to about 2.0.

As used herein with respect to a pore, the term "aspect ratio" refers to a ratio of the longest dimension of a pore to the shortest dimension of the pore. Rounded pores (e.g., pores having a round cross-section) generally have an aspect ratio of about 1.0 to about 1.5. Perfectly round cross-section has an aspect ratio of about 1.0. Example 9 provides an exemplary method to determine aspect ratios of pores present in a silk fibroin scaffold. For example, in some embodiments, SEM analysis of a cross-section of the silk fibroin scaffold can be performed. The contrast of the SEM images of the cross-section composite can be manipulated using any art-recognized image analysis tool (e.g., ImageJ or Phenom Porometric software) such that pores of the silk fibroin scaffold are distinguishable from the silk fibroin bulk material. Using an image analysis tool, the pores are then outlined, for example, using ellipses fitting, and the longest and shortest dimensions of the pores are measured to determine an aspect ratio of a pore. The aspect ratios of a representative number of the pores (e.g., at least 100 or more) are measured to create a distribution graph showing percentages of pores with respect to aspect ratios.

In some embodiments involving a silk fibroin non-liquid form (e.g., scaffold) described above and herein, the pores of the particles (e.g., silk fibroin particle) have an average circularity of about 0.4 to about 1.5, or about 0.5 to about 1.3, or about 0.6 to about 1.1. The circularity of pores is defined as: $(4\pi A_{pore}/P_{pore}^2)$, where $A_{pore}$ is the average cross-section area of the pores and $P_{pore}$ is the average perimeter forming the boundary of the cross-section area of the pores.

In some embodiments, the composition can be dehydrated to form a matrix comprising a porous structure, e.g., as described herein. This matrix can be milled to form round, porous silk fibroin particles.

The silk fibroin non-liquid form (e.g., scaffold) can be of any dimensions to suit the need of an application. For example, when the scaffold is used for breast reconstructions, the volume of the scaffold can be as large as 500 cm$^3$. Smaller scaffolds are also possible, e.g., when the scaffold are used as a dermal filler. In these embodiments, the scaffolds (e.g., particles) can be in micron ranges in size. In some embodiments, larger scaffolds can be further processed (e.g., by a mechanical means such as grinding, cutting, milling, and/or any other known methods of reducing a larger construct to smaller ones) to produce smaller scaffolds, e.g., as small as particles.

Another aspect provided herein relates to a silk fibroin scaffold comprising silk fibroin fragments and a plasticizer (e.g., glycerol), wherein the silk fibroin fragments have a weight average molecular weight of any of the above-referenced values or ranges, e.g., a weight average molecular weight ranging from about 100 kDa to about 160 kDa, and wherein the silk fibroin scaffold comprises a porous structure characterized by interconnected pores having an average pore size of any of the above-referenced values or ranges, e.g., an average circle equivalent diameter of about 5 µm to about 60 µm.

The silk fibroin scaffold can possess any one or more (e.g., 1, 2, 3, 4, 5, 6 or more) of the features of the compositions comprising silk fibroin fragments and a plasticizer (e.g., glycerol) as described above and herein. For example, the silk fibroin fragments in the scaffolds may display any combinations of characteristics of the molecular weight distribution described above and herein. By way of example only, the silk fibroin fragments may display a molecular weight distribution characterized in that: no more than about 20% of the total number of the silk fibroin fragments has a molecular weight exceeding about 200 kDa, and at least about 70% or more of the total number of the silk fibroin fragments has a molecular weight of about 30 kDa to about 170 kDa. Other combinations of the above-referenced characteristics of the molecular weight distribution are also possible.

In some embodiments, the plasticizer and silk fibroin fragments in the silk fibroin scaffolds described herein may be present in a weight ratio of any one of the above-referenced values or ranges as described above and herein. For example, in some embodiments, the weight ratio of a plasticizer (e.g., glycerol) and silk fibroin fragments in the silk fibroin scaffolds may be from about 0.5:100 to about 30:100, from about 0.5:100 to about 20:100, from about 0.5:100 to about 10:100, from about 0.5:100 to about 8:100, or from about 0.5:100 to about 6:100. In some embodiments, the weight ratio of a plasticizer (e.g., glycerol) and silk fibroin fragments in the silk fibroin scaffolds may be from about 1:100 to about 20:100, from about 1:100 to about 10:100, from about 1:100 to about 8:100, from about 1:100 to about 6:100. In one set of the embodiments described herein, the weight ratio of a plasticizer (e.g., glycerol) and silk fibroin fragments in the silk fibroin scaffolds may be about 6:100.

In some embodiments involving the silk fibroin scaffold described above and herein, the silk fibroin scaffold may be a lyophilized scaffold. The scaffold can come in any format, e.g., as described above. In some embodiments, the silk fibroin scaffold is a particle. In some embodiments, the particle can be produced from a larger scaffold described herein.

While the particles (e.g., generated or derived from a silk fibroin scaffold described above and herein, referred to as "silk fibroin particles" hereinafter) can be of any shape, e.g., a spherical shape, polygonal-shaped, elliptical-shaped, in some embodiments, the particles (e.g., silk fibroin particles) are substantially spherical. A substantially spherical particle, as described herein, has an aspect ratio of (a ratio of the major axis to the minor axis) of less than or equal to about 1.5, e.g., about 0.5 to about 1.5, about 0.6 to about 1.4, about 0.7 to about 1.3, about 0.8 to about 1.2, about 0.9 to about 1.1, or about 1.0 to about 1.1, while a non-spherical particle (e.g., an elongated particle) has an aspect ratio of more than about 1.5 or higher (e.g., more than about 2, more than about 3, more than about 4, more than about 5 or higher). To determine the aspect ratio of a particle, the dimensions of the particles can be determined from high-resolution images of particles, e.g., scanning electron microscopic images. For example, a population of particles can be imaged using a scanning electron microscope (SEM), e.g., a Phenom Pure SEM, e.g., with an accelerating voltage of about 5 kV, and then an image analysis tool (e.g., ImageJ) can be used to analyze the SEM images to determine relevant particle dimensions for computation of particle aspect ratio. For example, to perform image analysis, SEM images can be first converted to grayscale and subsequently converted to binary scale. The particle edges are then identified based on the binary images, e.g., using the "Find Edges" command or a functionally equivalent algorithm of an image analysis tool (e.g., ImageJ), and particle size can then be measured.

In some embodiments involving the particles described herein, the particles (e.g., silk fibroin particles) may have an aspect ratio of at least about 1.0, including, e.g., at least about 1.2, at least about 1.5, at least about 1.7, at least about 2.0, at least about 2.2, at least about 2.5, or higher. In some embodiments, the particles (e.g., silk fibroin particles) may have an aspect ratio of no more than about 3.0, including, e.g., less than or equal to about 2.7, less than or equal to about 2.5, less than or equal to about 2.2, less than or equal to about 2.0, less than or equal to about 1.5 or lower. Combinations of the above-referenced ranges are also possible. For example, in some embodiments, the aspect ratio of the particles (e.g., silk fibroin particles) may be about 1.0 to about 3.0.

The particles (e.g., silk fibroin particles) present in any embodiment of the compositions described herein can exhibit a distribution of particle sizes. The width of the particle size distribution can vary, e.g., by mixing particles of different size ranges or selecting particles of particular size ranges (e.g., by sieving). The narrower is the width of the particle size distribution, the more homogenous in size are the particles (e.g., silk fibroin particles) within the compositions described herein. The particle size can vary with a number of factors including, but not limited to, the size of defect in a tissue (e.g., soft tissue) to be repaired or augmented and/or desired properties of the particles, e.g., volume retention or degradation profile. The particles in any one of the compositions described herein can have any particle size that suits the need of a particular application. In some embodiments, the particles (e.g., silk fibroin particles) present in any embodiment of the compositions described herein can exhibit a distribution of particle sizes In some embodiments, the particle size of the particles (e.g., silk fibroin particles) is characterized by the average or mean value of a size distribution of the particles. The terms "average" and "mean" are interchangeably used herein. The average or mean value is generally associated with the basis of the size distribution calculation (e.g., number, surface, or volume). Accordingly, the average size of the particles (e.g., silk fibroin particles) can correspond to a number average size, a surface average size, or a volume average size. In one embodiment, the average size refers to volume mean diameter. In some embodiments, the particle size of the particles (e.g., silk fibroin particles) in any one of the compositions described herein is characterized by the mode of a size distribution of particles (e.g., silk fibroin particles), i.e., the value that occurs most frequently in the size distribution.

In some embodiments involving the particles described herein, the particle size (e.g., average particle size) of the particles (e.g., silk fibroin particles) is at least about 50 µm, at least about 75 µm, at least about 100 µm, at least about 125 µm, at least about 150 µm, at least about 200 µm, at least about 250 µm, at least about 300 µm, at least about 350 µm, at least about 400 µm, at least about 450 µm, at least about 500 µm, at least about 550 µm, at least about 600 µm, at least about 650 µm, at least about 700 µm, at least about 750 µm, at least about 800 µm, at least about 850 µm, at least about 900 µm, at least about 950 µm, or at least about 1000 µm. In some embodiments, the particle size (e.g., average particle size) of the particles (e.g., silk fibroin particles) is less than or equal to about 1000 µm, less than or equal to about 950 µm, less than or equal to about 900 µm, less than or equal to about 850 µm, less than or equal to about 800 µm, less than or equal to about 750 µm, less than or equal to about 700 µm, less than or equal to about 650 µm, less than or equal to about 600 µm, less than or equal to about 550 µm, less than or equal to about 500 µm, less than or equal to about 450 µm, less than or equal to about 400 µm, less than or equal to about 350 µm, less than or equal to about 300 µm, less than or equal to about 250 µm, less than or equal to about 200 µm, less than or equal to about 175 µm, less than or equal to about 150 µm, less than or equal to about 125 µm, less than or equal to about 100 µm, less than or equal to about 75 µm, or less than or equal to about 50 µm. Combinations of the above-referenced ranges are also possible. In some embodiments, the particle size (e.g., average particle size) of the particles (e.g., silk fibroin particles) may be about 200 µm to about 1000 µm, about 250 µm to about 850 µm, about 300 µm to about 800 µm, about 400 µm to about 600 µm, about 250 µm to about 450 µm, about 200 µm to about 500 µm, or about 300 µm to about 450 µm. In some embodiments, the particle size (e.g., average particle size) of the particles (e.g., silk fibroin particles) can be about 50 µm to about 200 µm. In some embodiments, the particle size (e.g., average particle size) of the particles (e.g., silk fibroin particles) can be about 75 µm to about 150 µm. In some embodiments, the particle size (e.g., average particle size) of the particles (e.g., silk fibroin particles) can be about 75 µm to about 125 µm. In some embodiments, the particle size (e.g., average particle size) of the particles (e.g., silk fibroin particles) can be about 300 µm to about 475 µm. In some embodiments, the particle size (e.g., average particle size) of the particles (e.g., silk fibroin particles) can be about 350 µm to about 430 µm. In some embodiments, the particle size (e.g., average particle size) of the particles (e.g., silk fibroin particles) can be about 355 µm to about 425 µm. In some embodiments of any particle size (e.g., average particle size) ranges described herein, the particle size (e.g., average particle size) of silk fibroin particles may refer to volume mean diameter of silk fibroin particles.

In some embodiments, particles of any of the above-referenced ranges can be selected from a composition comprising particles of different ranges, e.g., by sieving. Additionally or alternatively, the particle size distribution can be adjusted toward larger particle size or smaller particle size by varying the amount of a plasticizer (e.g., glycerol) present in a silk fibroin solution. For example, higher glycerol concentrations (e.g., 20-30% w/w) in a silk fibroin solution (e.g., at a concentration of about 10% w/v) tend to make smaller pores in a bulk scaffold, thus allowing smaller porous particles to be generated from the bulk scaffold.

Methods for measuring particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy). In some embodiments, laser diffraction is used to measure particle size of the compositions described herein. In some embodiments, scanning electron microscopy is used to measure particle size of the compositions described herein. For example, particles can be imaged using a scanning electron microscope (SEM), e.g., a Phenom Pure SEM, e.g., with an accelerating voltage of about 5 kV, and then an image analysis tool (e.g., ImageJ) can be used to analyze the SEM images to determine particle size as discussed above.

In some embodiments involving the compositions, scaffolds, and/or particles described herein, the composition, scaffolds, and/or particles may comprise any biocompatible material, for example, that is suitable for soft tissue augmentation and/or drug delivery in vivo. For example, in some embodiments, the composition, scaffold and/or particles may comprise a biocompatible and/or biodegradable polymer, a silk fibroin, a peptide, or any combinations thereof. Examples of biocompatible and/or biodegradable polymers include, but are not limited to polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid and other biocompatible and/or biodegradable polymers. See, e.g., International Application Nos.: WO 04/062697; WO 05/012606. In some embodiments, the biocompatible material, e.g., a biocompatible and/or biodegradable polymer, may be incorporated into a composition, scaffold, and/or particle, e.g., mixed with silk fibroin fragments or conjugated to silk fibroin fragments.

In some embodiments involving the compositions, scaffolds, and/or particles described herein, the composition, scaffolds, and/or particles may comprise one or more (including, e.g., 1, 2, 3, 4, 5, or more) active agent, examples of which are described in detail below in the section "Active agents." In some embodiments, the active agent may be incorporated in a composition, scaffold, and/or particle, e.g., mixed with silk fibroin fragments or conjugated to silk fibroin fragments.

In some embodiments involving the compositions, scaffolds, and/or particles of any aspects described above and herein, the compositions, scaffolds, and/or particles may include any suitable inactive ingredient included in U.S. Food & Drug Administration (FDA)'s database for Generally Recognized as Safe (GRAS) substances, which is accessible online at accessdata.fda.gov/scripts/fdcc/?set=SCOGS.

The compositions described herein can be formulated to suit the needs of various applications, including, e.g., soft tissue argumentation and/or repair, wound healing, cosmetic applications, and/or drug delivery. In some embodiments, a solution comprising a plasticizer (e.g., glycerol) and the silk fibroin fragments having any combination of the above-referenced weight average molecular weight ranges can be used to make silk fibroin articles or compositions of any shape or form, including, e.g., wound healing devices and/or cosmetics products (e.g., topical cosmetic products). As discussed above, the shift in $T_g$ for the combination of a LMW silk fibroin solution and a plasticizer (e.g., glycerol) indicates that the material is more malleable and thus it is easier to manipulate such a material to a desired shape or form.

Compositions Comprising Silk Fibroin Particles

Compositions comprising silk fibroin particles as described above and herein are also provided. The composition may further comprise at least one or more (e.g., 1, 2, 3, or more) of the following: a carrier such as a pharmaceutically acceptable carrier, an active agent as described herein; and any suitable inactive GRAS substance as discussed above.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or stearic acid), or solvent encapsulating material, involved in maintaining the stability, solubility, or activity of, silk fibroin materials and/or an active agent, if any, dispersed therein. Each carrier must be "acceptable" in the sense of being compatible with the other ingredients of the formulation and not injurious to the patient.

In some embodiments, the compositions may comprise at least one or more (including, e.g., 1, 2, 3, 4, or more) of the following: small molecules, proteins, peptides, polypeptides, alternative sugars (e.g., but not limited to glucose or sucrose), polyols, wound healing drugs/medications such as antibiotics, growth factors (e.g., but not limited to VEGF, interleukins), anti-inflammatory drugs, analgesics, antibodies, enzymes, enzyme inhibitors, therapeutic agents, cells, tissues, hormones, optically or electrically active agents (including, e.g., but not limited to dyes, fluorescently tagged molecules/drugs, any active agent described herein containing or conjugated to a detectable label such as a fluorescent tag, cells expressing a fluorescent protein, proteins and/or antibodies conjugated to a detectable label such as a dye or fluorescent tag), and any combinations thereof.

In some embodiments, the compositions are injectable compositions. For example, the silk fibroin particles as described above and herein can form injectable compositions with low extrusion force, making them suitable for soft tissue augmentation, repair, and/or ingrowth. Accordingly, one aspect provided herein relates to an injectable composition comprising a matrix carrier (e.g., crosslinked or non-crosslinked) and silk fibroin particles as described in the Section "Compositions, scaffolds, or particles comprising silk fibroin fragments and a plasticizer" above. By way of example only, in some embodiments, the silk fibroin particles can comprise silk fibroin fragments and a plasticizer (e.g., glycerol), wherein the silk fibroin fragments have a weight average molecular weight of any of the above-referenced values or ranges, e.g., a weight average molecular weight ranging from about 100 kDa to about 160 kDa, and wherein the silk fibroin scaffold comprises a porous structure characterized by interconnected pores having an average pore size of any of the above-referenced values or ranges, e.g., an average circle equivalent diameter of about 5 μm to about 60 μm.

As used herein, the phrase "silk fibroin particles" generally refers to particles comprising silk fibroin. In some embodiments, the phrase "silk fibroin particles" refers to particles in which silk fibroin constitutes at least about 30% of the total particle composition, including at least about 40%, at least about 50%, at least about 60%, at least about 70%, at least about 80%, at least about 90%, at least about 95% or up to 100%, of the total particle composition. In certain embodiments, the silk fibroin particles can be substantially formed from silk fibroin. In one embodiment, the silk fibroin particles consist essentially of silk fibroin.

The silk fibroin particle can possess any one or more (e.g., 1, 2, 3, 4, 5, 6 or more) of the features of the compositions comprising silk fibroin fragments and a plasticizer (e.g., glycerol) as described in the Section "Compositions, scaffolds, or particles comprising silk fibroin fragments and a plasticizer" above. For example, the silk fibroin fragments in the particles may display any combinations of characteristics of the molecular weight distribution described in the aforementioned Section. By way of example only, the silk fibroin fragments may display a molecular weight distribution characterized in that: no more than about 20% of the total number of the silk fibroin fragments has a molecular weight exceeding about 200 kDa, and at least about 70% or more of the total number of the silk fibroin fragments has a molecular weight of about 30 kDa to about 170 kDa. Other combinations of the above-referenced characteristics of the molecular weight distribution are also possible.

In some embodiments, the average particle size of the silk fibroin particles may be of any one of values or ranges provided in the Section "Compositions, scaffolds, or particles comprising silk fibroin fragments and a plasticizer" above. For example, the average particle size of the silk fibroin particles may be about 50 μm to about 1000 μm, about 200 μm to about 1000 μm, about 250 μm to about 850 μm, about 300 μm to about 800 μm, about 400 μm to about 600 μm, about 250 μm to about 450 μm, about 200 μm to about 500 μm, about 300 μm to about 450 μm, about 50 μm to about 200 μm, or about 75 μm to about 125 μm. In some embodiments of any average particle size ranges described herein, the average particle size of silk fibroin particles may refer to volume mean diameter of silk fibroin particles.

The average particle size of the silk fibroin particles in some embodiments involving the injectable compositions described herein may be selected to suit the need of each application. For example, smaller average particle size may be desirable for vocal fold augmentation, while larger average particle size may be more suitable for large volume reconstruction (e.g., breast reconstruction). Accordingly, in some embodiments, the silk fibroin particles have an average particle size of about 250 µm to about 450 µm, or about 300 µm to about 400 µm. In alternative embodiments, the silk fibroin particles may have an average particle size of about 400 µm to about 600 µm or about 450 µm to about 550 µm.

In some embodiments, the plasticizer and silk fibroin fragments in the silk fibroin particles described herein may be present in a weight ratio of any one of the above-referenced values or ranges as described in the Section "Compositions, scaffolds, or particles comprising silk fibroin fragments and a plasticizer" above. For example, in some embodiments, the weight ratio of a plasticizer (e.g., glycerol) and silk fibroin fragments in the silk fibroin particles may be from about 0.5:100 to about 30:100, from about 0.5:100 to about 20:100, from about 0.5:100 to about 10:100, from about 0.5:100 to about 8:100, or from about 0.5:100 to about 6:100. In some embodiments, the weight ratio of a plasticizer (e.g., glycerol) and silk fibroin fragments in the silk fibroin particles may be from about 1:100 to about 30:100, about 1:100 to about 20:100, from about 1:100 to about 10:100, from about 1:100 to about 8:100, from about 1:100 to about 6:100. In one set of the embodiments described herein, the weight ratio of a plasticizer (e.g., glycerol) and silk fibroin fragments in the silk fibroin particles may be about 6:100. Higher concentrations of a plasticizer (e.g., glycerol) can generate smaller pores within scaffolds (e.g., particles) described herein In some embodiments, the matrix carrier is a crosslinked matrix carrier. The crosslinked matrix carrier in the injectable compositions described herein may comprise crosslinked glycosaminoglycan polymers (e.g., crosslinked hyaluronic acid), crosslinked extracellular matrix protein polymers (e.g., crosslinked collagen, crosslinked elastin, and/or crosslinked fibronectin), crosslinked polysaccharides (e.g., crosslinked cellulose), crosslinked fibrous protein polymers, or a combination of two or more thereof. In one set of embodiments of the compositions or injectable compositions described herein, the crosslinked matrix carrier is crosslinked hyaluronic acid.

In some embodiments, the crosslinked carrier comprises a hyaluronic acid polymer. In some embodiments, the crosslinked carrier essentially consists of hyaluronic acid polymer. In some embodiments, the hyaluronic acid polymer may have an average molecular weight of at least about 200 kDa, at least about 300 kDa, at least about 400 kDa, at least about 500 kDa, at least about 600 kDa, at least about 700 kDa, at least about 800 kDa, at least about 900 kDa, at least about 1 MDa, at least about 2 MDa, at least about 3 MDa, at least about 4 MDa, or at least about 5 MDa. In some embodiments, the hyaluronic acid polymer may have an average molecular weight of less than or equal to about 5 MDa, less than or equal to about 4 MDa, less than or equal to about 3 MDa, less than or equal to about 2 MDa, less than or equal to about 1 MDa, less than or equal to about 900 kDa, less than or equal to about 800 kDa, less than or equal to about 700 kDa, less than or equal to about 600 kDa, less than or equal to about 500 kDa, less than or equal to about 400 kDa, less than or equal to about 300 kDa, or less than or equal to about 200 kDa. Combinations of the above-referenced ranges are also possible. For example, in some embodiments, the hyaluronic acid polymer may have an average molecular weight of about 200 kDa to about 5 MDa, or about 300 kDa to about 4 MDa, or about 400 kDa to about 3 MDa, or about 500 kDa to about 2 MDa. In some embodiments, the hyaluronic acid polymer may have an average molecular weight of about 1 MDa or greater, e.g., 1 MDa, 1.5 MDa, 2 MDa, 2.5 MDa, 3 MDa, 3.5 MDa, 4 MDa, 4.5 MDa, 5 MDa or higher. In some embodiments, the hyaluronic acid polymer may have an average molecular weight of about 1 MDa or lower, e.g., 0.9 MDa, 0.8 MDa, 0.7 MDa, 0.6 MDa, 0.5 MDa, 0.4 MDa, 0.3 MDa, 0.2 MDa, 0.1 MDa, or lower. The average molecular weights provided herein for the hyaluronic acid polymer can correspond to weight average molecular weights, number average molecular weights, or peak average molecular weights. In one set of the embodiments described herein, the average molecular weights provided herein for the hyaluronic acid polymer correspond to weight average molecular weights.

In some embodiments involving the injectable compositions described herein, the crosslinked matrix carrier (e.g., crosslinked hyaluronic acid) may have a concentration of at least about 0.1% (w/v), at least about 0.5% (w/v), at least about 1% (w/v), at least about 2% (w/v), at least about 3% (w/v), at least about 4% (w/v), at least about 5% (w/v), at least about 6% (w/v), at least about 7% (w/v), at least about 8% (w/v), at least about 9% (w/v), at least about 10% (w/v). In some embodiments, the crosslinked matrix carrier (e.g., crosslinked hyaluronic acid) may have a concentration of no more than 10% (w/v), no more than 9% (w/v), no more than 8% (w/v), no more than 7% (w/v), no more than 6% (w/v), no more than 5% (w/v), no more than 4% (w/v), no more than 3% (w/v), no more than 2% (w/v), no more than 1% (w/v), no more than 0.5% (w/v), or no more than 0.1% (w/v). Combinations of the above-referenced ranges are also possible. For example, in some embodiments, the crosslinked matrix carrier (e.g., crosslinked HA) have a concentration of about 0.1% (w/v) to about 10% (w/v) or 0.5% (w/v) to about 10% (w/v), or 1% (w/v) to about 10% (w/v), or about 2% (w/v) to about 8% (w/v), or about 3% (w/v) to about 6% (w/v).

In one set of embodiments described herein, the crosslinked carrier (e.g., a crosslinked HA) has a crosslink density of at least about 10 mol %, at least about 11 mol %, at least about 12 mol %, at least about 13 mol %, at least about 14 mol %, at least about 15 mol %, at least about 16 mol %, at least about 17 mol %, at least about 18 mol %, at least about 19 mol %, at least about 20 mol %, at least about 25 mol %, at least about 30 mol %, at least about 35 mol %, at least about 40 mol %, or higher. In some embodiments, the crosslinked carrier (e.g., a crosslinked HA) has a crosslink density of no more than about 40 mol %, no more than about 35 mol %, no more than about 30 mol %, no more than about 25 mol %, or no more than about 20 mol %. Combinations of the above-referenced ranges are also possible. For example, in some embodiments, the crosslinked carrier (e.g., a crosslinked HA) may have a crosslink density of about 10 mol % to about 30 mol %, about 10 mol % to about 25 mol %, or about 10 mol % to about 20 mol %.

As used herein, the term "crosslink density" describes the final crosslink density of a crosslinked carrier, which is determined as a ratio of the total number of molecules (or moles) of a crosslinking agent incorporated into the crosslinked carrier to the total number of repeating entity molecules (or moles) of the carrier present in the crosslinked carrier, multiplied by 100. For example, the crosslink density of crosslinked hyaluronic acid is a ratio of the total number of molecules (or moles) of a crosslinking agent (e.g., BDDE) incorporated into the crosslinked HA to the total number of disaccharide units (repeating entity molecules) of hyaluronic acid present in the crosslinked HA, multiplied by 100. The crosslink density of a crosslinked carrier can be determined, for example, by proton nuclear magnetic resonance (1H NMR). Examples of cross-linking agents include, but are not limited to epichlorohydrin, divinyl sulfone, 1,4-bis(2,3-epoxypropoxy)butane (or 1,4-bisglycidoxybutane or 1,4-butanediol diglycidyl ether (BDDE)), 1,2-bis(2,3-epoxypropoxy)ethylene, 1-(2,3-epoxypropyl)-2,3-epoxycyclohexane, and aldehydes such as formaldehyde, glutaraldehyde and crotonaldehyde, taken by themselves or in a mixture The crosslinked matrix carrier (e.g., crosslinked HA) and the silk fibroin particles can be present in any volume ratio that yields properties of the compositions suitable for the need of a particular application. In some embodiments of any one of the injectable compositions described herein, the total amounts of crosslinked matrix carrier (e.g., crosslinked HA) and the silk fibroin particles are in a volume ratio of at least about 5:95, at least about 10:90, at least about 15:85, at least about 20:80, at least about 25:75, at least about 30:70, at least about 35:65, at least about 40:60, at least about 45:55, at least about 50:50, at least about 55:45, at least about 60:40, at least about 65:35, at least about 70:30, at least about 75:25, at least about 80:20, at least about 85:15, at least about 90:10, or at least about 95:5. In some embodiments, the total amounts of crosslinked matrix carrier (e.g., crosslinked HA) and the silk fibroin particles are in a volume ratio of less than or equal to about 100:1, less than or equal to about 95:5, less than or equal to about 90:10, less than or equal to about 85:15, less than or equal to about 80:20, less than or equal to about 75:25, less than or equal to about 70:30, less than or equal to about 65:35, less than or equal to about 60:40, less than or equal to about 55:45, less than or equal to about 50:50, less than or equal to about 45:55, less than or equal to about 40:60, less than or equal to about 35:65, less than or equal to about 30:70, less than or equal to about 25:75, less than or equal to about 20:80, less than or equal to about 15:85, less than or equal to about 10:90, or less than or equal to about 5:95. Combinations of the above-referenced ranges are also possible. For example, in some embodiments of any one of the injectable compositions described herein, the total amounts of crosslinked matrix carrier (e.g., crosslinked HA) and the silk fibroin particles are in a volume ratio of about 5:95 to about 95:5, or about 10:90 to about 90:10, or about 20:80 to about 80:20, or about 25:75 to about 75:25, or about 30:70 to about 70:30, or about 40:60 to about 60:40. In some embodiments, the total amounts of crosslinked matrix carrier (e.g., crosslinked HA) and the silk fibroin particles are in a volume ratio of about 50:50; about 40:60; about 30:70; about 25:75; about 20:80, or about 10:90, or as low as about 5:95. In some embodiments, the total amounts of crosslinked matrix carrier (e.g., crosslinked HA) and the silk fibroin particles are in a volume ratio of about 60:40, about 70:30, about 75:25; about 80:20, about 90:10 or up to about 95:5. In one embodiment, the cross-linking agent comprises 1,4-butanediol diglycidyl ether (BDDE).

In some embodiments involving the compositions of any aspects described above and herein, the injectable composition may be pre-loaded in a syringe.

Methods of Producing a Population of Silk Fibroin Porous Particles

Another aspect provided herein relates to a method of producing a population of silk fibroin porous particles. The method comprises: (a) providing a solution comprising silk fibroin fragments and a plasticizer (e.g., glycerol), the silk fibroin fragments having a weight average molecular weight of any one of the above-referenced ranges, e.g., a weight average molecular weight in a range of about 100 kDa to about 160 kDa, wherein the plasticizer (e.g., glycerol) and the silk fibroin fragments are present in a weight ratio of any one of the above-referenced values or ranges, e.g., a weight ratio of about 0.5:100 to about 20:100; (b) lyophilizing or freeze-drying the solution to produce a lyophilized or freeze-dried silk fibroin porous scaffold; and (c) reducing the lyophilized or freeze-dried silk fibroin porous scaffold into particles. Such a method provides a population of silk fibroin porous particles that are rounder and more uniform that the particles produced by methods that do not involve a plasticizer (e.g., glycerol).

In some embodiments, the particles produced by the methods described herein have an aspect ratio of an aspect ratio of at least about 1.0, including, e.g., at least about 1.2, at least about 1.5, at least about 1.7, at least about 2.0, at least about 2.2, at least about 2.5, or higher. In some embodiments, the particles (e.g., silk fibroin particles) may have an aspect ratio of less than or equal to about 3.0, including, e.g., less than or equal to about 2.7, less than or equal to about 2.5, less than or equal to about 2.2, less than or equal to about 2.0, less than or equal to about 1.5 or lower. Combinations of the above-referenced ranges are also possible. For example, in some embodiments, the aspect ratio of the particles (e.g., silk fibroin particles) may be about 1.0 to about 3.0.

In some embodiments, the particles produced by the methods described herein have an average pore size of less than or equal to about 100 µm, less than or equal to about 95 µm, less than or equal to about 90 µm, less than or equal to about 85 µm, less than or equal to about 80 µm, less than or equal to about 75 µm, less than or equal to about 70 µm, less than or equal to about 65 µm, less than or equal to about 60 µm, less than or equal to about 55 µm, less than or equal to about 50 µm, less than or equal to about 45 µm, less than or equal to about 40 µm, less than or equal to about 35 µm, less than or equal to about 30 µm, less than or equal to about 25 µm, less than or equal to about 20 µm, less than about 15 µm, less than about 10 µm, or lower. In some embodiments, the particles produced by the methods described herein have an average pore size of at least about 5 µm, at least about 10 µm, at least about 15 µm, at least about 20 µm, at least about 25 µm, at least about 30 µm, at least about 35 µm, at least about 40 µm, at least about 45 µm, at least about 50 µm, at least about 55 µm, at least about 60 µm, at least about 65 µm, at least about 70 µm, at least about 75 µm, at least about 80 µm, at least about 85 µm, at least about 90 µm, at least about 95 µm, or at least about 100 µm, or higher. Combinations of the above-referenced ranges are also possible. In some embodiments, the particles produced by the methods described herein may have an average pore size of about 5 µm to about 100 µm, or about 5 µm to about 60 µm, or about 10 µm to about 60 µm, or about 30 µm to about 50 µm. In some embodiments, the above-referenced average pore size may refer to average circle equivalent diameter.

In some embodiments, the porous structure of the particles produced by the methods described herein may be characterized by no more than 10% (including, e.g., no more than about 9%, no more than about 8%, no more than about 7%, no more than about 6%, no more than about 5% or lower) of interconnected pores having an average pore size (e.g., an average circle equivalent diameter) of about 100 µm or greater.

In some embodiments, the porous structure of the particles produced by the methods described herein may be characterized by no more than 15% (including, e.g., no more than about 14%, no more than about 13%, no more than 12%, no more than 11%, no more than 10%, no more than about 9%, no more than about 8%, no more than about 7%, no more than about 6%, no more than about 5% or lower) of interconnected pores having an average pore size (e.g., an average circle equivalent diameter) of about 75 μm or greater.

In some embodiments, the porous structure of the particles produced by the methods described herein may be characterized by at least about 50% (including, e.g., at least about 60%, at least about 70%, at least about 80%, at least about 90%, or above) of interconnected pores having an average pore size (e.g., an average circle equivalent diameter) of about 5 μm to about 75 μm, or about 15 μm to about 60 μm, or about 15 μm to about 55 μm.

In some embodiments of the particles produced by the methods described herein, at least about 40% (including, e.g., at least about 50%, at least about 60%, at least about 70%, at least about 80%, at least about 90% or more and up to 100%) of the pores have an aspect ratio of about 1.0 to about 2.5.

In some embodiments of the particles produced by the methods described herein, no more than about 10% (including, e.g., no more than about 9%, no more than about 8%, no more than about 7%, no more than about 6%, no more than about 5%, or lower) of the pores have an aspect ratio of at least about 2.5 or higher (e.g., including, e.g., at least about 3.0, at least about 3.5, at least about 4.0, or higher).

In some embodiments of the particles produced by the methods described herein, the pores have an average aspect ratio of at least about 1.5, at least about 1.6, at least about 1.7, at least about 1.8, at least about 1.9, at least about 2.0. In some embodiments, the pores have an average aspect ratio of no more than about 2.5, no more than about 2.4, no more than about 2.3, no more than about 2.2, no more than about 2.1, no more than about 2.0, no more than about 1.9, no more than about 1.8, no more than about 1.7, no more than about 1.6, or lower. Combinations of the above-referenced ranges are possible. For example, in some embodiments, the pores have any average aspect ratio of about 1.5 to about 2.5, or about 1.8 to about 2.0.

In some embodiments of the particles produced by the methods described herein, the pores have an average circularity of about 0.4 to about 1.5, or about 0.5 to about 1.3, or about 0.6 to about 1.1.

In some embodiments involving the methods and/or compositions described herein, at least about 80% or higher (including, e.g., at least about 85%, at least about 90%, at least about 95%, at least about 98%, or higher, up to 100%) of the silk fibroin particles in the population have an aspect ratio in size of about 1 to about 3, including any combinations of the above-referenced ranges and have an average pore size of any one of the above-referenced ranges, e.g., an average circle equivalent diameter of about 5 μm to about 60 μm.

In some embodiments involving the methods described above and herein, the plasticizer (e.g., glycerol) and the silk fibroin fragments in the solution are present in a weight ratio ranging from about 0.5:100 to about 30:100, from about 0.5:100 to about 20:100, from about 0.5:100 to about 10:100, from about 0.5:100 to about 8:100, or from about 0.5:100 to about 6:100. In some embodiments, the weight ratio of a plasticizer (e.g., glycerol) and silk fibroin fragments may range from about 1:100 to about 20:100, from about 1:100 to about 10:100, from about 1:100 to about 8:100, from about 1:100 to about 6:100. In one set of the embodiments described herein, the weight ratio of a plasticizer (e.g., glycerol) and silk fibroin fragments may be about 6:100. In some embodiments, the glycerol and the silk fibroin fragments are present in a weight ratio of about 6:100, producing 0.6% (w/v) glycerol of the total solution. The plasticizer (e.g., glycerol) is preferably added to the solution comprising silk fibroin fragments at room temperature, for example, after the silk fibroin fragments have been purified and are substantially free of sericin.

In some embodiments, a weight percentage of silk fibroin fragments can be present in the solution at any concentration suited to a particular volume retention or degradation requirement. For example, higher concentrations of silk fibroin in the solution can be used when longer volume retention or slower degradation rate of the silk fibroin particles is desired upon injection into a tissue to be repaired or augmented. In some embodiments, the solution can have silk fibroin fragments at a concentration of about 0.1 mg/mL to about 50 mg/mL, or about 0.5 mg/mL to about 25 mg/mL, or about 1 mg/mL to about 15 mg/mL. In some embodiments, the solution can comprise silk fibroin fragments at a concentration of less than or equal to 1 about mg/mL, less than or equal to about 1.5 mg/mL, less than or equal to about 2 mg/mL, less than or equal to about 2.5 mg/mL, less than or equal to about 3 mg/mL, less than or equal to about 3.5 mg/mL, less than or equal to about 4 mg/mL, less than or equal to about 4.5 mg/mL, less than or equal to about 5 mg/mL, less than or equal to about 5.5 mg/mL, less than or equal to about 6 mg/mL, less than or equal to about 6.5 mg/mL, less than or equal to about 7 mg/mL, less than or equal to about 7.5 mg/mL, less than or equal to about 8 mg/mL, less than or equal to about 8.5 mg/mL, less than or equal to about 9 mg/mL, less than or equal to about 9.5 mg/mL, less than or equal to about 10 mg/mL, less than or equal to about 11 mg/mL, less than or equal to about 12 mg/mL, less than or equal to about 13 mg/mL, less than or equal to about 14 mg/mL, less than or equal to about 15 mg/mL, less than or equal to about 16 mg/mL, less than or equal to about 17 mg/mL, less than or equal to about 18 mg/mL, less than or equal to about 19 mg/mL, less than or equal to about 20 mg/mL, less than or equal to about 25 mg/mL, less than or equal to about 30 mg/mL, less than or equal to about 35 mg/mL, less than or equal to about 40 mg/mL, less than or equal to about 45 mg/mL, or less than or equal to about 50 mg/mL. In some embodiments, the solution can have silk fibroin fragments at a concentration of at least about 0.1 mg/mL, at least about 0.5 mg/mL, at least about 1 mg/mL, at least about 5 mg/mL, at least about 10 mg/mL, at least about 15 mg/mL, at least about 20 mg/mL, at least about 25 mg/mL, at least about 30 mg/mL, at least about 35 mg/mL, at least about 40 mg/mL, or higher.

In some embodiments, the silk fibroin solution can vary from about 4% (w/v) to about 30% (w/v), inclusive, or about 4% (w/v) to about 20% (w/v), inclusive. In some embodiments, the silk fibroin solution can vary from about 6% (w/v) to about 20% (w/v). In some embodiments, the silk fibroin solution can vary from about 6% (w/v) to about 17% (w/v). Suitable processes for preparing silk fibroin solution are disclosed, for example, in U.S. Pat. No. 7,635,755; and International Application Numbers: WO/2005/012606; and WO/2008/127401.

In some embodiments, the solution comprising the silk fibroin fragments and plasticizer (e.g., glycerol) is subjected to lyophilization or freeze-drying to produce a lyophilized or freeze-dried silk fibroin porous scaffold. Lyophilization and freeze-drying of silk fibroin solutions to generate porous materials is known in the art, e.g., as described in Li et al. *J Control Release*. (2015) 219:416-30; Li et al. *Journal of Applied Polymer Science* (2001) 79: 2192-2199; Brown et al. *Adv. Healthcare Mater.* (2017) 6: 1600762; Guziewicz et al. *Biomaterials* (2011) 32: 2642-2650; Rnjak-Kovacina et al. *Macromol. Biosci.* (2015) 15: 861-874; Rnjak-Kovacina et al. *ACS Biomater. Sci. Eng.* (2015) 1: 260-270; and Kluge et al. *ACS Biomater. Sci. Eng.* (2016) 2: 595-605, and the PCT Patent Publication No. WO2016/145281, the contents of each of which are incorporated herein by reference.

Controlling the freezing process within a lyophilizer can control the porosity of a silk fibroin matrix. The solution comprising the silk fibroin fragments and plasticizer (e.g., glycerol) described herein may be lyophilized or freeze-dried in any laboratory-grade freeze-dryer system. For example, one such system is the Virtis Genesis Freeze Dryer, set up with the silk/plasticizer mixture (e.g., silk/glycerol mixture) in stainless steel trays. The silk/plasticizer mixture (e.g., silk/glycerol mixture) is then cooled to a temperature of about −20° C., and held at about −20° C. for a period of about 8 hours or more, e.g., more than about 8 hours, more than about 9 hours, more than about 10 hours or longer. The cooled silk/plasticizer mixture (e.g., silk/glycerol mixture) is then heated to a temperature of about 25° C., and held at about 25° C. for a period of about 20 hours or more, e.g., more than about 20 hours, more than about 21 hours, more than about 22 hours or longer.

In some embodiments, the step of lyophilizing or freeze-drying the solution can comprise lyophilizing and/or slow freezing over a period to a target temperature. In some embodiments, a target temperatures is between about −20° C. or about −50° C. In some embodiments, a target temperature is at least colder that the glass transition temperature of silk. In some embodiments, a target temperature is: at least about −50° C. or higher, including, e.g., at least about −45° C., at least about −40° C., at least about −35° C., at least about −30° C., at least about −25° C., or higher. In some embodiments, a target temperature is: less than or equal to about −20° C. or lower, including, e.g., less than or equal to about −25° C., less than or equal to about −30° C., less than or equal to about −35° C., less than or equal to about −40° C., less than or equal to about −45° C., less than or equal to about −50° C., or lower.

In some embodiments, the step of lyophilizing or freeze-drying the solution can comprise lyophilizing and/or slow freezing over a period at fixed or variable rate. In some embodiments, a shelf temperature is cooled according to a fixed or variable rate. In some embodiments, cooling at such a rate occurs until a target temperature is reached. In some embodiments, a time to reach a target temperature, for example, is between about 10 and about 20 hours.

In some embodiments, the step of lyophilizing or freeze-drying the solution can comprise lyophilizing and/or slow freezing over a period at a rate of between about −1.0° C./min and about 0.001° C./min. In some embodiments, the step of lyophilizing or freeze-drying the solution can comprise lyophilizing and/or slow freezing over a period at a rate of about: less than about −1.0° C./min, less than about −0.09° C./min, less than about −0.08° C./min, less than about −0.07° C./min, less than about −0.06° C./min, less than about −0.05° C./min, less than about −0.04° C./min, less than about −0.03° C./min, less than about −0.02° C./min, less than about −0.01° C./min, less than about −0.009° C./min, less than about −0.008° C./min, less than about −0.007° C./min, less than about −0.006° C./min, less than about −0.005° C./min, less than about −0.004° C./min, less than about −0.003° C./min, less than about −0.002° C./min, or less than about −0.001° C./min.

In some embodiments involving the methods and/or compositions described herein, the lyophilized or freeze-dried silk fibroin porous scaffold may be subjected to a post-treatment that will affect at least one silk fibroin property. For example, post-treatment of the lyophilized or freeze-dried silk fibroin porous scaffold can affect silk fibroin properties including β-sheet content, solubility, active agent loading capacity, degradation time, drug permeability, or any combinations thereof. Silk post-processing options include controlled slow drying (Lu et al., 10 Biomacromolecules 1032 (2009)), water annealing (Jin et al., Water-Stable Silk Films with Reduced β-Sheet Content, 15 Adv. Funct. Mats. 1241 (2005)), stretching (Demura & Asakura, Immobilization of glucose oxidase with *Bombyx mori* silk fibroin by only stretching treatment and its application to glucose sensor, 33 Biotech & Bioengin. 598 (1989)), compression, and solvent immersion, including methanol (Hofmann et al., 2006), ethanol (Miyairi et al., 1978), glutaraldehyde (Acharya et al., 2008) and N-ethyl-N'-(3-dimethyl aminopropyl) carbodiimide (EDC) (Bayraktar et al., 2005).

In some embodiments, the post-treatment may comprise contacting the lyophilized or freeze-dried silk fibroin porous scaffold with a beta-sheet inducing agent. Agents to induce beta-sheet formation in silk fibroin are known in the art. An exemplary beta-sheet inducing agent comprises methanol.

Figure 15A:
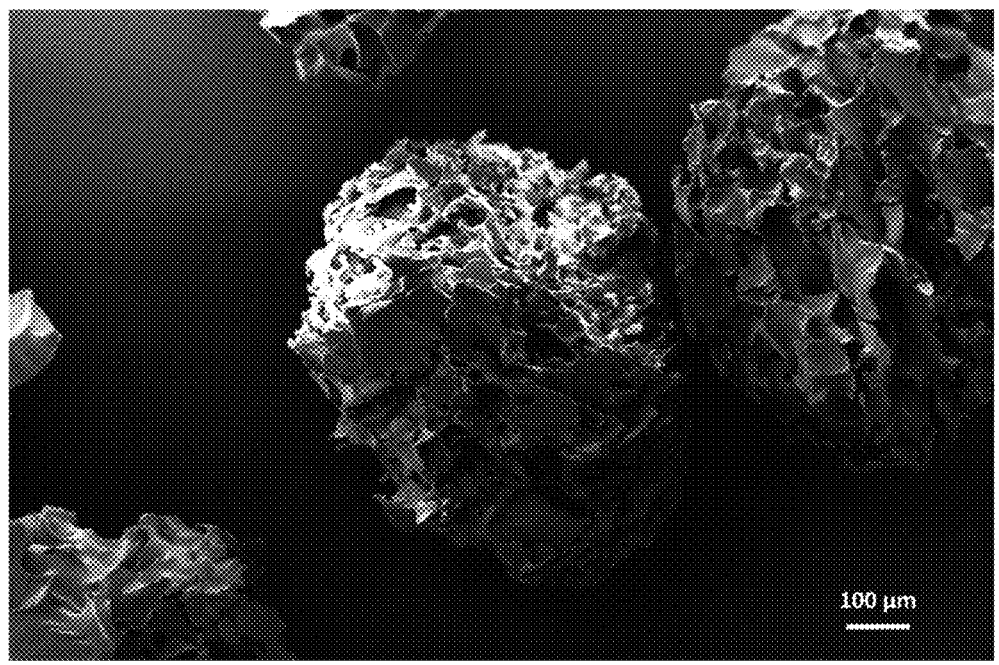
FIG. 15A is a microscopic image of individual silk fibroin particles according to one set of embodiments described herein. The porous silk fibroin particle have an average particle size of about 500 microns to about 600 microns in diameter and an average pore size of about 40 µm in diameter.
Figure 15B:
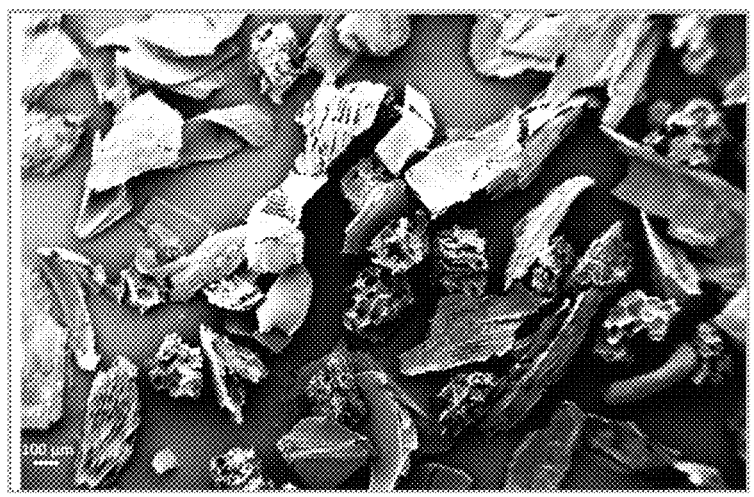
FIG. 15B depicts silk fibroin particles produced from the silk fibroin bulk material without glycerol.

The lyophilized or freeze-dried silk fibroin porous scaffold (e.g., after post-treatment with methanol) is then reduced into particles, e.g., using any methods known in the art such as grinding, cutting, and milling. In other words, in such embodiments, the particles are formed from the bulk silk fibroin porous scaffold. The addition of plasticizer (e.g., glycerol) provides additional improved mechanical properties to allow for efficient processing (e.g. milling) of the freeze-dried silk fibroin porous scaffold to form particles. These silk fibroin porous particles comprise a porous structure characterized by interconnected pores having an average pore size of about 20 μm to about 100 μm or any of the above-referenced ranges. The absence of a plasticizer changes the freezing properties of the particles and may render them too brittle for processing (e.g., milling). FIGS. 15A and 15B illustrate how the addition of a plasticizer (e.g., glycerol) to a solution comprising low molecular weight silk fibroin fragments significantly improves the shape of the particles (e.g., to form rounder particles). Rounder particles (e.g., particles having a relatively low aspect ratio) may improve injectability of a composition comprising the particles.

In some embodiments, the solution comprising silk fibroin fragments having a weight molecular weight ranging from about 100 kDa to about 160 kDa (including combinations of the above-referenced ranges) may be produced by a process comprising: (1) processing a silk fiber or silk cocoon (e.g., heated and/or boiled) in a sufficient amount to achieve fragmentation of silk fibroin polypeptides, e.g., to achieve a desired molecular weight distribution of silk fibroin fragments, as determined, for example, by SDS gel electrophoresis or HPLC-RID; (2) removing sericin; (3) resolubilizing, upon sericin removal, the silk fibroin fragments, for example, in lithium bromide; (4) filtering the solution of step (3), e.g., to remove debris; and (5) adding a plasticizer (e.g., glycerol) to achieve any one of the above-referenced weight ratio of the plasticizer to silk fibroin fragments. In some embodiments, the final concentration of silk fibroin fragments and plasticizer in the solution of step (5) may be about 10% (w/v) silk fibroin and 0.6% (w/v) glycerol.

Degummed silk can be prepared by any conventional method known to one skilled in the art. For example, *B. mori* cocoons or silk fibers are boiled for a period of predetermined time in an aqueous solution. Generally, a long degumming time generates low molecular silk fibroin fragments. See WO 2014/145002 for methods of making low molecular weight silk fibroin fragments, the content of which is incorporated herein by reference in its entirety. In some embodiments, the silk cocoons or silk fibers are boiled for at least about 60 minutes, at least about 70 minutes, at least about 80 minutes, at least about 90 minutes, at least about 100 minutes, at least about 110 minutes, at least about 120 minutes, or longer (e.g., up to about 180 minutes). In some embodiments, the silk cocoons or silk fibers may be boiled for no more than about 180 minutes, no more than about 170 minutes, no more than about 160 minutes, no more than about 150 minutes, no more than about 140 minutes, no more than about 130 minutes, no more than about 120 minutes, no more than about 110 minutes, no more than about 100 minutes, no more than about 90 minutes, no more than about 80 minutes, or no more than about 70 minutes. Combinations of the above-referenced ranges are also possible. For example, in some embodiments, the silk cocoons may be boiled for about 60 minutes to about 180 minutes, about 60 minutes to about 160 minutes, about 60 minutes to about 140 minutes, or about 60 minutes to about 120 minutes.

In some embodiments, silk cocoons or silk fibers can be heated or boiled at an elevated temperature (e.g., for an amount of time described above). For example, in some embodiments, silk cocoons may be heated or boiled at a temperature of at least about 95° C., at least about 100° C., at least about 101.0° C., at least about 101.5° C., at least about 102.0° C., at least about 102.5° C., at least about 103.0° C., at least about 103.5° C., at least about 104.0° C., at least about 104.5° C., at least about 105.0° C., at least about 105.5° C., at least about 106.0° C., at least about 106.5° C., at least about 107.0° C., at least about 107.5° C., at least about 108.0° C., at least about 108.5° C., at least about 109.0° C., at least about 109.5° C., at least about 110.0° C., at least about 110.5° C., at least about 111.0° C., at least about 111.5° C., at least about 112.0° C., at least about 112.5° C., at least about 113.0° C., at least about 113.5° C., at least about 114.0° C., at least about 114.5° C., at least about 115.0° C., at least about 115.5° C., at least about 116.0° C., at least about 116.5° C., at least about 117.0° C., at least about 117.5° C., at least about 118.0° C., at least about 118.5° C., at least about 119.0° C., at least about 119.5° C., at least about 120.0° C., or higher (e.g., up to about 130° C.). In some embodiments, silk cocoons or silk fibers may be heated or boiled a temperature of no more than about 130° C., no more than about 125° C., no more than about 120° C., no more than about 105° C., or no more than about 100° C. Combinations of the above-referenced ranges are also possible. In some embodiments, silk cocoons or silk fibers may be heated or boiled at a temperature of about 95° C. to about 110° C., or about 100° C. to about 105° C.

In some embodiments, the elevated temperature at any of the above-referenced ranges can be achieved by carrying out at least portion of the heating process (e.g., boiling process) under suitable pressure. For example, the suitable pressure under which silk fibroin fragments are produced are typically between about 10-40 psi, between about 10-35 psi, between about 10-30 psi, or between about 10-20 psi. In some embodiments, the pressure may be at least about 10 psi, at least about 11 psi, at least about 12 psi, at least about 13 psi, at least about 14 psi, at least about 15 psi, at least about 20 psi, at least about 25 psi, at least about 30 psi, at least about 35 psi, or at least about 40 psi. In some embodiments, the pressure may be no more than 40 psi, no more than 35 psi, no more than 30 psi, no more than 25 psi, no more than 20 psi, no more than 15 psi, or no more than 10 psi. Combinations of the above-referenced ranges are also possible.

In some embodiments involving the methods described herein, the heating and/or boiling silk cocoons or silk fibers to remove sericin may refer to heating silk fibers or silk cocoon at an atmospheric boiling or heating temperature (e.g., at a boiling or heating temperature as described above) in an aqueous sodium carbonate solution for at least a period of about 60 minutes or more, e.g., more than 60 minutes, more than 70 minutes, more than 80 minutes, more than 90 minutes or longer.

In one embodiment, the aqueous solution used in the process of degumming silk cocoons is about 0.001 M to about 0.5 M $Na_2CO_3$ (e.g., about 0.02 M $Na_2CO_3$ in one embodiment). The cocoons are rinsed, for example, with water to extract the sericin proteins. The degummed silk can be then dissolved, e.g., in an aqueous salt solution. Salts useful for this purpose include lithium bromide, lithium thiocyanate, calcium nitrate or other chemicals capable of solubilizing silk. In some embodiments, the degummed silk can be dissolved by maintaining the silk fibers in about 8 M-12 M LiBr solution, or in about 8.5 M-11.5 M LiBr solution, or in about 9 M-11 M LiBr solution for up to 6 hours (including, e.g., up to 5 hours, up to 4 hours, up to 3 hours, up to 2 hours, up to 1 hr) at an average temperature of about 55° C. to about 65° C. In some embodiments, the average temperature is about 60° C. The salt is consequently removed using, for example, dialysis. In most cases dialysis for about 2-12 hours can be sufficient. However, in some embodiments, dialysis can be performed for more than about 12 hours, e.g., at least about 12 hours, at least about 24 hours, at least about 2 days, at least about 3 days, at least about 4 days, at least about 5 days or longer (e.g., up to about 1 week). See, for example, International Patent Application Publication No. WO 2005/012606, the content of which is incorporated herein by reference in its entirety.

In some embodiments, the silk fibroin solution can be concentrated and/or purified, e.g., by centrifugation or filtration, e.g., using a 0.2 μm filter. In one embodiment, the silk fibroin solution is passed through a vacuum filtration system after the sericin has been removed.

Other Silk Processing Methods, e.g., for Producing Various Scaffolds as Described Herein The solution comprising low molecular weight silk fibroin fragments and a plasticizer (e.g., glycerol) as prepared by the methods as described in the section "Methods of producing a population of silk fibroin porous particles" above can be subjected to various dehydration methods other than freeze-drying, to form various forms of scaffolds, which include, e.g., but are not limited to air-drying, salt-leaching, and gas foaming methods, and spray-drying. See, e.g., U.S. Pat. No. 7,842,780; and US Patent Application Nos: US 2010/0279112; and US 2010/0279112, the contents of which are incorporated herein by reference in their entirety.

A silk fibroin scaffold (including particles produced by the methods described above) can be produced from aqueous-based or organic solvent-based silk fibroin solutions. The aqueous- or organic solvent-based silk fibroin solution used for making silk fibroin scaffold (including particles produced by the methods described above) can be prepared using any techniques known in the art.

In some embodiments involving the methods for producing a silk fibroin scaffold (including the methods for producing silk fibroin particles described above), at least one active agent described herein can be added to the silk fibroin solution before further processing into a silk fibroin scaffold described herein. In some embodiments, the active agent can be dispersed homogeneously or heterogeneously within the silk fibroin, dispersed in a gradient, e.g., using the carbodiimide-mediated modification method described in the U.S. Patent Application No. US 2007/0212730. In some embodiments, the silk fibroin scaffold can be first formed and then contacted with (e.g., dipped into) at least one active agent such that the open surface of the scaffold can be coated with at least one active agent.

In some embodiments, the silk fibroin scaffold can be subjected to any of the above-described post-treatment that will affect at least one silk fibroin property. For example, in some embodiments, post-treatment of a silk fibroin scaffold, e.g., water-annealing or solvent immersion, can modulate the degradation or solubility properties of the silk fibroin scaffold described herein. In some embodiments, post-treatment of the silk fibroin scaffold, e.g., water-annealing or solvent immersion, can modulate the volume retention properties of the silk fibroin scaffold described herein.

In some embodiments involving the methods for producing a silk fibroin scaffold (including the methods for producing silk fibroin particles described above), the silk fibroin scaffold described herein (including, e.g., particles) can be coated with at least one layer of a biocompatible and/or biodegradable polymer described herein, e.g., to modulate the degradation and/or volume retention properties of the silk fibroin scaffold (including, e.g., particles) upon implantation (e.g., injection) into a tissue to be treated and/or to modulate the rate of active agents, if any, released from the silk fibroin scaffold (including, e.g., particles). In such embodiments, the biocompatible and/or biodegradable polymer can comprise at least one active agent.

In some embodiments involving the methods for producing a silk fibroin scaffold (including the methods for producing silk fibroin particles described above), the silk fibroin scaffold (including, e.g., particles) described herein can be coated with cell adhesion molecules, e.g., but not limited to, fibronectin, vitronectin, laminin, collagen, any art-recognized extracellular matrix molecules, and any combinations thereof.

In some embodiments involving the methods for producing a silk fibroin scaffold (including the methods for producing silk fibroin particles described above), the silk fibroin scaffold (including, e.g., particles) described herein can be sterilized. In some embodiments, compositions comprising silk fibroin particles and a matrix carrier (e.g., but not limited to HA) are sterilized. In some embodiments, a delivery device (e.g., but not limited to a syringe) comprising silk fibroin particles and a matrix carrier (e.g., but not limited to HA) are sterilized. Sterilization methods for biomaterials and/or biomedical devices are well known in the art, including, but not limited to, gamma or ultraviolet radiation, autoclaving (e.g., heat/steam); alcohol sterilization (e.g., ethanol and methanol); gas sterilization (e.g., ethylene oxide sterilization) and heat sterilization. In some embodiments, compositions comprising silk fibroin particles and a matrix carrier (e.g., but not limited to HA) are subject to heat sterilization. In some embodiments, a delivery device (e.g., but not limited to a syringe) comprising silk fibroin particles and a matrix carrier (e.g., but not limited to HA) are subject to heat sterilization.

In some embodiments involving the methods for producing a silk fibroin scaffold (including the methods for producing silk fibroin particles described above), the silk fibroin solution can be sterilized, e.g., by sterile filtration, prior to forming a silk fibroin scaffold from the silk fibroin solution.

In some embodiments involving the methods for producing a silk fibroin scaffold (including the methods for producing silk fibroin particles described above), the silk fibroin scaffold (including, e.g., particles) described herein can take advantage of the many techniques developed to functionalize silk fibroin (e.g., active agents such as dyes and sensors). See, e.g., U.S. Pat. No. 6,287,340, Bioengineered anterior cruciate ligament; WO 2004/000915, Silk Biomaterials & Methods of Use Thereof; WO 2004/001103, Silk Biomaterials & Methods of Use Thereof; WO 2004/062697, Silk Fibroin Materials & Use Thereof; WO 2005/000483, Method for Forming inorganic Coatings; WO 2005/012606, Concentrated Aqueous Silk Fibroin Solution & Use Thereof; WO 2011/005381, Vortex-Induced Silk fibroin Gelation for Encapsulation & Delivery; WO 2005/123114, Silk-Based Drug Delivery System; WO 2006/076711, Fibrous Protein Fusions & Uses Thereof in the Formation of Advanced Organic/Inorganic Composite Materials; U.S. Application Pub. No. 2007/0212730, Covalently immobilized protein gradients in three-dimensional porous scaffolds; WO 2006/042287, Method for Producing Biomaterial Scaffolds; WO 2007/016524, Method for Stepwise Deposition of Silk Fibroin Coatings; WO 2008/085904, Biodegradable Electronic Devices; WO 2008/118133, Silk Microspheres for Encapsulation & Controlled Release; WO 2008/108838, Microfluidic Devices & Methods for Fabricating Same; WO 2008/127404, Nanopatterned Biopolymer Device & Method of Manufacturing Same; WO 2008/118211, Biopolymer Photonic Crystals & Method of Manufacturing Same; WO 2008/127402, Biopolymer Sensor & Method of Manufacturing Same; WO 2008/127403, Biopolymer Optofluidic Device & Method of Manufacturing the Same; WO 2008/127401, Biopolymer Optical Wave Guide & Method of Manufacturing Same; WO 2008/140562, Biopolymer Sensor & Method of Manufacturing Same; WO 2008/127405, Microfluidic Device with Cylindrical MicroChannel & Method for Fabricating Same; WO 2008/106485, Tissue-Engineered Silk Organs; WO 2008/140562, Electroactive Biopolymer Optical & Electro-Optical Devices & Method of Manufacturing Same; WO 2008/150861, Method for Silk Fibroin Gelation Using Sonication; WO 2007/103442, Biocompatible Scaffolds & Adipose-Derived Stem Cells; WO 2009/155397, Edible Holographic Silk Products; WO 2009/100280, 3-Dimensional Silk Hydroxyapatite Compositions; WO 2009/061823, Fabrication of Silk Fibroin Photonic Structures by Nanocontact Imprinting; WO 2009/126689, System & Method for Making Biomaterial Structures.

Exemplary Methods of Use

The compositions (including, e.g., injectable compositions, scaffolds and/or particles) of various aspects described herein can be used for any suitable biomedical applications such as soft tissue augmentation, regeneration, and/or ingrowth, scaffolding, and/or wound sealing or clotting. In some embodiments, the compositions described herein can be also configured for drug delivery, e.g., incorporating an active agent into the compositions or silk fibroin particles as described herein. In some embodiments, the compositions are used as a dermal filler. In some embodiments where the compositions are used a dermal filler, the compositions can further comprise an active agent for improving skin appearance and/or elasticity (e.g., onabotulinumtoxin A (Botox®). In some embodiments, the compositions are used as an injectable implant for vocal fold medialization. Other applications are also possible.

In some embodiments, provided herein are compositions (including, e.g., injectable compositions, scaffolds and/or particles) that can be used to fill, volumize, and/or regenerate a tissue in need thereof. The compositions (including, e.g., injectable compositions, scaffolds and/or particles) can generally be used for tissue filling or volumizing, soft tissue augmentation, replacement, cosmetic enhancement and/or tissue repair in a subject. Additionally, the compositions (including, e.g., injectable compositions, scaffolds and/or particles) can be used for filling of any tissue void or indentation that are either naturally formed (e.g., aging) or created by surgical procedure for removal of tissue (e.g., a dermal cyst or a solid tumor), corticosteroid treatment, immunologic reaction resulting in lipoatrophy, tissue damage resulting from impact injuries or therapeutic treatment (e.g., radiotherapy or chemotherapy). The injectable compositions can also be used to raise scar depressions.

In certain embodiments, the compositions (including, e.g., injectable compositions, scaffolds and/or particles) can be used for soft tissue augmentation. As used herein, by the term "augmenting" or "augmentation" is meant increasing, filling in, restoring, enhancing or replacing a tissue. In some embodiments, the tissue can lose its elasticity, firmness, shape and/or volume. In some embodiments, the tissue can be partially or completely lost (e.g., removal of a tissue) or damaged. In those embodiments, the term "augmenting" or "augmentation" can also refer to decreasing, reducing or alleviating at least one symptom or defect in a tissue (for example, but not limited to, loss of elasticity, firmness, shape and/or volume in a tissue; presence of a void or an indentation in a tissue; loss of function in a tissue) by injecting into the tissue with at least one injectable composition described herein. In such embodiments, at least one symptom or defect in a tissue can be decreased, reduced or alleviated by at least about 30%, at least about 40%, at least about 50%, at least about 60%, at least about 70%, at least about 80% or higher, as compared to no treatment. In some embodiments, at least one symptom or defect in a tissue can be decreased, reduced or alleviated by at least about 90%, at least about 95%, at least about 97%, or higher, as compared to no treatment. In some embodiments, at least one symptom or defect in a tissue can be decreased, reduced or alleviated by 100% (defect-free or the defect is undetectable by one of skill in the art), as compared to no treatment. In other embodiments, the tissue can be augmented to prevent or delay the onset of defect manifestation in a tissue, e.g., loss of elasticity, firmness, shape and/or volume in a tissue, or signs of wrinkles. As used herein, the phrase "soft tissue augmentation" is generally used in reference to altering a soft tissue structure, including but not limited to, increasing, filling in, restoring, enhancing or replacing a tissue, e.g., to improve the cosmetic or aesthetic appearance of the soft tissue. Examples of soft tissue augmentation include, but are not limited to, dermal tissue augmentation; filling of lines, folds, wrinkles, minor facial depressions, and cleft lips, especially in the face and neck; correction of minor deformities due to aging or disease, including in the hands and feet, fingers and toes; augmentation of the vocal cords or glottis to rehabilitate speech; dermal filling of sleep lines and expression lines; replacement of dermal and subcutaneous tissue lost due to aging; lip augmentation; filling of crow's feet and the orbital groove around the eye; chin augmentation; augmentation of the cheek and/or nose; bulking agent for periurethral support, filling of indentations in the soft tissue, dermal or subcutaneous, due to, e.g., overzealous liposuction or other trauma; filling of acne or traumatic scars; filling of nasolabial lines, nasoglabellar lines and intraoral lines. In some embodiments, the compositions (including, e.g., injectable compositions, scaffolds and/or particles) described herein can be used to treat facial lipodystrophies.

In some embodiments, the compositions (including, e.g., injectable compositions, scaffolds and/or particles) can be used for soft tissue repair. The term "repair" or "repairing" as used herein, with respect to a tissue, refers to any correction, reinforcement, reconditioning, remedy, regenerating, filling of a tissue that restores volume, shape and/or function of the tissue. In some embodiments "repair" includes full repair and partial repair. For example, the volume, shape and/or function of a tissue to be repaired can be restored by at least about 30%, at least about 40%, at least about 50%, at least about 60%, at least about 70%, at least about 80% or higher within a certain period of time (e.g., within about 12 months, within about 9 months, within about 6 months, within about 3 months or shorter), as compared to no treatment. In some embodiments, the volume, shape and/or function of a tissue to be repaired can be restored by at least about 90%, at least about 95%, at least about 97%, or higher, within a certain period of time (e.g., within about 12 months, within about 9 months, within about 6 months, within about 3 months or shorter), as compared to no treatment. In some embodiments, the volume, shape and/or function of a tissue to be repaired can be restored by 100% (defect-free or the defect is undetectable by one of skill in the art) within a certain period of time (e.g., within about 12 months, within about 9 months, within about 6 months, within about 3 months or shorter), as compared to no treatment. In various embodiments, the compositions (including, e.g., injectable compositions, scaffolds and/or particles) can be used to repair any soft tissues discussed earlier, e.g., skin, and any soft tissues amenable for soft tissue augmentation. Without wishing to be bound by theory, the compositions (including, e.g., injectable compositions, scaffolds and/or particles) described herein can promote tissue ingrowth, which may ultimately shorten repair time. For example, tissue or cellular ingrowth into the pores of the silk fibroin particles described herein can improve the healing response.

The compositions (including, e.g., injectable compositions, scaffolds and/or particles) described herein can also be used for filling a tissue located at or near a prosthetic implant, for example, but not limited to, a conventional breast implant or knee replacement implant. In some embodiments, the compositions (including, e.g., injectable compositions, scaffolds and/or particles) can be used to interface between a prosthetic implant and a tissue, e.g., to fill a void between the prosthetic implant and the tissue, and/or to prevent the tissue in direct contact with the prosthetic implant. By way of example only, after placing a prosthetic implant (e.g., a breast implant) in a subject, a composition (including, e.g., an injectable composition, scaffold and/or particles) described herein can be introduced at or adjacent to the implant to fill any void between the implant and the tissue (e.g., breast tissue) and/or "sculpt" the tissue for a more natural look.

In any of the uses described herein, the compositions (including, e.g., injectable compositions, scaffolds and/or particles) described herein can be combined with cells for purposes of a biologically enhanced augmentation and/or tissue ingrowth. Cells can be dispersed in the carrier and/or silk fibroin particles. Cells can be collected from a multitude of hosts including but not limited to human autograft tissues, or transgenic mammals. More specifically, human cells used can comprise cells selected from stem cells (e.g., adipocytederived stem cells), fibroblasts, lipocytes, assorted immunocytes, cells from lipoaspirate or any combinations thereof.

In some embodiments, administering the cells (e.g., stem cells) with any embodiment of the compositions (including, e.g., injectable compositions, scaffolds and/or particles) described herein can enhance or accelerate host integration and/or tissue formation over time. The cells can be dispersed in any embodiment of the compositions (including, e.g., injectable compositions, scaffolds and/or particles) described herein, or they can be administered prior to, concurrently with, or after the composition is introduced into a target site. Without wishing to be bound by theory, the cells can secrete pro-angiogenic factors and/or growth factors at the target site. As the tissue regenerates or remodels to fill up a void or repair a defect, the silk fibroin particles and/or carrier matrix can degrade accordingly. In some embodiments, the silk fibroin particles and/or carrier matrix can integrate with the regenerated host tissue.

In some aspects, the compositions (including, e.g., injectable compositions, scaffolds and/or particles) described herein can be used as tissue space fillers or bulking agents for treating a defect in a soft tissue of a subject, e.g., for soft tissue augmentation and/or ingrowth. Accordingly, methods for augmenting or regenerating different soft tissues are provided herein. In some embodiments, such a method comprises injecting to a site of defect in a soft tissue a composition comprising silk fibroin particles of any embodiments or aspects described herein and a carrier, or a composition of any embodiments or as aspects described herein.

The compositions can be applied to treat different soft tissues for small volume bulking or large volume bulking applications, including but not limited to, a skin tissue, e.g., a facial skin tissue, a bladder tissue (e.g., a urethra), a cervical tissue, a vocal fold tissue, a breast tissue, or a buttock tissue. Other applications are also possible, for example, stationary phases for liquid chromatography and/or embolization therapy (occlusion of vessels to prevent hemorrhaging).

In some embodiments, any of the compositions (including, e.g., injectable compositions, scaffolds and/or particles) described herein are used to treat a facial skin tissue. For example, any embodiment of the compositions (including, e.g., injectable compositions, scaffolds and/or particles) described herein can be injected to a facial line or wrinkle, or a scar. Thus, in some embodiments, the compositions (including, e.g., injectable compositions, scaffolds and/or particles) described herein can be used as a dermal filler. The dermal filler comprising any embodiment of the compositions (including, e.g., injectable compositions, scaffolds and/or particles) can be modulated for particle compressibility, elasticity, softness, and/or opacity through alteration of silk fibroin concentration and/or carrier matrix. The dermal filler can be used to improve skin appearance or condition, including, but not limited to, rehydrating the skin, providing increased elasticity to the skin, reducing skin roughness, making the skin tauter, reducing or eliminating stretch lines or marks, giving the skin better tone, shine, brightness, and/or radiance, reducing or eliminating wrinkles in the skin, providing wrinkle resistance to the skin and replacing loss of soft tissue.

Accordingly, another aspect described herein provides a method of improving a condition and/or appearance of skin in a subject in need thereof. Non-limiting examples of a skin condition or and/or appearance include dehydration, lack of skin elasticity, roughness, lack of skin tautness, skin stretch line and/or marks, skin paleness, and skin wrinkles. The method comprises injecting any embodiment of the compositions (including, e.g., injectable compositions, scaffolds and/or particles) described herein into a dermal region of the subject, wherein the injection improves the skin condition and/or appearance. For example, improving a skin appearance may include, but is not limited to, rehydrating the skin, providing increased elasticity to the skin, reducing skin roughness, making the skin tauter, reducing or eliminating stretch lines or marks, giving the skin better tone, shine, brightness and/or radiance to reduce paleness, reducing or eliminating wrinkles in the skin, and providing wrinkle resistance to the skin.

As used herein, the term "dermal region" refers to the region of skin comprising the epidermal-dermal junction and the dermis, including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis include, but are not limited to, keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Stretch marks from pregnancy are also located in the dermis.

The hypodermis is not part of the skin, and lies below the dermis. Its purpose is to attach the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In one set of embodiments, methods of treatment are provided. In one embodiment, a method of treating a lack of skin elasticity comprises injecting to a dermal region suffering from a lack of skin elasticity any embodiment of the compositions (including, e.g., injectable compositions, scaffolds and/or particles) described herein, wherein the injection of the composition increases the elasticity of the skin, thereby treating a lack of skin elasticity.

In another embodiment, a method of treating skin roughness comprises injecting to a dermal region suffering from skin roughness any embodiment of the compositions (including, e.g., injectable compositions, scaffolds and/or particles) described herein, wherein the injection of the composition decreases skin roughness, thereby treating skin roughness.

In still another embodiment, a method of treating a lack of skin tautness comprises injecting to a dermal region suffering from a lack of skin tautness any embodiment of the compositions (including, e.g., injectable compositions, scaffolds and/or particles) described herein, wherein the injection of the composition makes the skin tauter, thereby treating a lack of skin tautness.

In a further embodiment, a method of treating a skin stretch line or mark comprises injecting to a dermal region suffering from a skin stretch line or mark any embodiment of the compositions (including, e.g., injectable compositions, scaffolds and/or particles) described herein, wherein the injection of the composition reduces or eliminates the skin stretch line or mark, thereby treating a skin stretch line or mark.

In another embodiment, a method of treating skin wrinkles comprises injecting to a dermal region suffering from skin wrinkles any embodiment of the compositions (including, e.g., injectable compositions, scaffolds and/or particles) described herein, wherein the injection of the composition reduces or eliminates skin wrinkles, thereby treating skin wrinkles.

In yet another embodiment, a method of treating, preventing or delaying the formation of skin wrinkles comprises injecting to a dermal region susceptible to, or showing signs of wrinkles any embodiment of the compositions (including, e.g., injectable compositions, scaffolds and/or particles) described herein, wherein the injection of the composition makes the skin resistant to skin wrinkles, thereby treating, preventing or delaying the formation of skin wrinkles.

In some embodiments of the compositions (including, e.g., injectable compositions, scaffolds and/or particles) described herein, the compositions (including, e.g., injectable compositions, scaffolds and/or particles) can be used to treat a target site (e.g., a target site of no more than 3 cm$^3$, no more than 2 cm$^3$, or no more than 1 cm$^3$) for urogenital applications (e.g., a target site, e.g., a defect, in a bladder tissue). For example, urethral bulking—where bulking material is injected into the bladder neck and urethra—is used to treat incontinence due to sphincter deficiency. In some embodiments, the compositions (including, e.g., injectable compositions, scaffolds and/or particles) described herein can bulk urethra walls, restoring the sealing mechanism, and be programmed for long term volume retention for lasting effect. For example, the silk fibroin particles can maintain up to about 90%, or up to about 85%, or up to about 80%, or up to about 75% of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 24 months after injection). In some embodiments, the silk fibroin particles can maintain at least about 20%, at least about 30%, at least about 40%, at least about 50%, at least about 60%, at least about 70%, at least about 80%, or at least about 90%, of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 36 months after injection). Combinations of the above-referenced ranges are also possible. For example, in some embodiments, the silk fibroin particles can maintain about 20% to about 90% or about 30% to about 80%, or about 40% to about 70% of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after the injection (e.g., up to about 36 months after injection).

In some embodiments of the compositions (including, e.g., injectable compositions, scaffolds and/or particles) described herein, the compositions (including, e.g., injectable compositions, scaffolds and/or particles) can be used to treat cervical insufficiency, a disease which is known to increase the risk of preterm labor. An injectable bulking agent into the walls of cervix can enhance the mechanical properties of the cervical canal to reduce the risk of early pregnancy. Current treatments for cervical insufficiency include cervical cerclage, which is often associated with hemorrhage, tearing, and difficult implantation procedures. A minimally invasive injectable alternative using the compositions (including, e.g., injectable compositions, scaffolds and/or particles) described herein may improve tissue mechanics without the drawbacks associated with sutures. In some embodiments, the compositions (including, e.g., injectable compositions, scaffolds and/or particles) described herein can bulk the walls of cervix to reduce the risk of early pregnancy.

In some embodiments of the compositions (including, e.g., injectable compositions, scaffolds and/or particles) described herein, the compositions (including, e.g., injectable compositions, scaffolds and/or particles) can be used to augment vocal fold in subjects in need thereof, e.g., a subject having vocal cord paresis or glottal insufficiency. In these embodiments, the method comprises injecting to a target site (e.g., a glottal gap) in the vocal fold a subject in need thereof any embodiment of the compositions (including, e.g., injectable compositions, scaffolds and/or particles) described herein, with a needle of an appropriate gauge size. In some embodiments, the injection can comprise trans-oral injection, percutaneous injection, or thyroid injection. In some embodiments, the injection is trans-oral injection, for example, which can be performed with a catheter for delivering the composition to the site of defect in the vocal fold.

In some embodiments of the compositions (including, e.g., injectable compositions, scaffolds and/or particles) described herein for augmenting vocal fold, the silk fibroin particles provide a bulking effect such that it closes the glottal gap by maintaining up to about 90%, or up to about 85%, or up to about 80%, or up to about 75% of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 24 months after injection). In some embodiments, the silk fibroin particles can maintain at least about 20%, at least about 30%, at least about 40%, at least about 50%, at least about 60%, at least about 70%, at least about 80%, or at least about 90%, of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after injection (e.g., up to about 36 months after injection). Combinations of the above-referenced ranges are also possible. For example, in some embodiments, the silk fibroin particles can maintain about 20% to about 90% or about 30% to about 80%, or about 40% to about 70% of the particles' original volume (e.g., injected volume) for at least about 3 months or longer (including, e.g., at least about 4 months, at least about 5 months, at least about 6 months, at least about 7 months, at least about 8 months, at least about 9 months, at least about 10 months, at least about 11 months, at least about 12 months or longer) after the injection (e.g., up to about 36 months after injection).

In another aspect, any embodiment of the compositions (including, e.g., injectable compositions, scaffolds and/or particles) described herein can be used for applications, including, e.g., fistula occlusion or similar wounds caused by injury or surgery. For example, any embodiment of the compositions (including, e.g., injectable compositions, scaffolds and/or particles) described herein can be used to seal the abnormal connection between two or more tissues, allowing epithelium to develop around the silk implant, reforming a natural epithelial barrier and preventing the exchange of substances that may cause further infection or inflammation.

In some embodiments, any embodiment of the compositions (including, e.g., injectable compositions, scaffolds and/or particles) described herein can be used as scaffolds to support cell growth for tissue engineering. For example, any embodiment of the compositions (including, e.g., injectable compositions, scaffolds and/or particles) described herein can be administered into an incision or wound site to promote wound healing or wound disclosure. The methods generally comprise administering any embodiment of the compositions (including, e.g., injectable compositions, scaffolds and/or particles) described herein, at the wound or incision site and allowing the wound or incision to heal while the silk fibroin particles is eroded or absorbed in the body and is replaced with the individual's own viable tissue. The methods can further comprise seeding the silk fibroin particles or mixing the composition with viable cellular material, either from the individual or from a donor, prior to or during administration.

For any methods of use described herein, the effective amount and administration schedule of any embodiment of the compositions (including, e.g., injectable compositions, scaffolds and/or particles) described herein injected into a soft tissue (e.g., a dermal tissue, a bladder tissue, a cervical tissue, or a vocal fold tissue) can be determined by a person of ordinary skill in the art taking into account various factors, including, without limitation, the size, condition, and/or location of a defect to be treated, and the duration of treatment desired, the properties (e.g., degradation rate, and/or pharmacodynamics) of selected compositions (including, e.g., injectable compositions, scaffolds and/or particles) for treatment, history and risk factors of the individual, such as, e.g., age, weight, general health, and any combinations thereof. In some embodiments, any embodiment of the compositions (including, e.g., injectable compositions, scaffolds and/or particles) described herein can be injected into a defect to be treated every about 3 months, every about 6 months, every about 9 months, every about one year, every about two years or longer.

In some embodiments of any of the compositions (including, e.g., injectable compositions, scaffolds and/or particles) described herein, the compositions (including, e.g., injectable compositions, scaffolds and/or particles) comprising at least one active agent can be used as a platform for drug delivery. For example, the silk fibroin particles can be formed with a pharmaceutical agent either entrained in or bound to the particles and then administered into the body (e.g., injection, implantation or even oral administration). In some embodiments, an active agent can be mixed with a composition (including, e.g., an injectable composition, a scaffold and/or particles) and then administered into the body (e.g., injection, implantation or even oral administration). For extended or sustained release, silk fibroin particles can manipulated, e.g., to modulate its beta-sheet content, for its volume retention and/or degradation rate. The therapeutic-bound silk fibroin particles can also be further cross-linked to enhance the stability to extend the release period. In an alternative approach, silk fibroin particles can be mixed with other polymers, for examples, hyaluronic acid, to prolong the release of certain growth factors or cytokines and to stabilize the functionality.

As used herein, the term "sustained release" refers to the release of a pharmaceutically-active drug over a period of about seven days or more. In aspects of this embodiment, a drug delivery platform comprising any embodiment of the compositions (including, e.g., injectable compositions, scaffolds and/or particles) described herein releases a pharmaceutically-active drug over a period of, e.g., at least about 7 days after administration, at least about 15 days after administration, at least about 30 days after administration, at least about 45 days after administration, at least about 60 days after administration, at least about 75 days after administration, or at least about 90 days after administration (and/or up to 360 days or up to 120 days after administration).

As used herein, the term "extended release" refers to the release of a pharmaceutically-active drug over a period of time of less than about seven days. In such embodiments, a drug delivery platform comprising any embodiment of the compositions (including, e.g., injectable compositions, scaffolds and/or particles) described herein can release a pharmaceutically-active drug over a period of, e.g., about 1 day after administration, about 2 days after administration, about 3 days after administration, about 4 days after administration, about 5 days after administration, or about 6 days after administration.

Depending on the formulation and processing methods of the compositions and the associated applications, any embodiment of the compositions (including, e.g., injectable compositions, scaffolds and/or particles) described herein can be administered (e.g., by injection) periodically, for example, every about 3 months, every about 4 months, every about 5 months, every about 6 months, every about 7 months, every about 8 months, every about 9 months, every about 10 months, every about 11 months, every about 1 year, every about 2 years or longer.

In some embodiments of any of the applications described herein, any embodiment of the compositions (including, e.g., injectable compositions, scaffolds and/or particles) described herein can be injected subcutaneously, submuscularly, or intramuscularly. In some embodiments, the methods and/or compositions described herein can be used in the dermal region. In some embodiments, the methods and/or compositions described herein can be used in the epidermal layer, dermal layer, hypodermis layer, or any combinations thereof.

Active Agents

In some embodiments, the compositions or injectable compositions and/or the particles (e.g., silk fibroin particles) as described herein can further comprise at least one active agent. The active agent can be mixed, dispersed, or suspended in any embodiment of the compositions or injectable compositions described herein, including the particles (e.g., silk fibroin particles) and/or the carrier, and/or the active agent can be distributed or embedded in any embodiment of the particles (e.g., silk fibroin particles). In some embodiments, the active agent can be distributed, embedded or encapsulated in the particles (e.g., silk fibroin particles). In some embodiments, the active agent can be coated on surfaces of the particles (e.g., silk fibroin particles). In some embodiments, the active agent can be mixed with the particles (e.g., silk fibroin particles) to form an injectable composition. The term "active agent" can also encompass combinations or mixtures of two or more active agents, as described below. Examples of active agents include, but are not limited to, a biologically active agent (e.g., an therapeutic agent, an anesthetic, a cell growth factor, a peptide, a peptidomimetic, an antibody or a portion thereof, an antibody-like molecule, nucleic acid, a polysaccharide, and any combinations, cells, stem cells, biological fluids, immune suppressors, antibacterial agents, anti-inflammatory agents, analgesics, etc.), a cosmetically active agent (e.g., an anti-aging agent, an anti-free radical agent, an anti-oxidant, a hydrating agent, a whitening agent, a colorant, a depigmenting agent, a sun-blocking agent, a muscle relaxant, etc.), a cell attachment agent (e.g., collagen, crosslinked hyaluronic acid/collagen, integrin-binding molecules, chitosan, elastin, fibronectin, vitronectin, laminin, proteoglycans, any derivatives thereof, any peptide or oligosaccharide variants), and any combinations thereof.

The term "biologically active agent" as used herein refers to any molecule which exerts at least one biological effect in vivo. For example, the biologically active agent can be a therapeutic agent to treat or prevent a disease state or condition in a subject. Examples of biologically active agents include, without limitation, peptides, peptidomimetics, aptamers, antibodies or a portion thereof, antibody-like molecules, nucleic acids (DNA, RNA, siRNA, shRNA), polysaccharides, enzymes, receptor antagonists or agonists, hormones, growth hormones, growth factors, cell signaling factors, autogenous bone marrow, antibiotics, antimicrobial agents, small molecules and therapeutic agents. The biologically active agents can also include, without limitations, anti-inflammatory agents, anesthetics, and active agents that stimulate tissue healing, formation, and/or ingrowth, cell recruitment, integration into surrounding tissue matrix, and/or regrowth of natural tissues, and any combinations thereof. Cells, living tissues or tissue components such as lipoaspirate, extracellular matrix components can be included in any embodiment of the compositions, injectable compositions and/or particles (e.g., silk fibroin particles) described herein.

Anti-inflammatory agents can include, but are not limited to, naproxen, sulindac, tolmetin, ketorolac, celecoxib, ibuprofen, diclofenac, acetylsalicylic acid, nabumetone, etodolac, indomethacin, piroxicam, cox-2 inhibitors, ketoprofen, antiplatelet medications, salsalate, valdecoxib, oxaprozin, diflunisal, flurbiprofen, corticosteroids, MMP inhibitors and leukotriene modifiers or combinations thereof.

Agents that increase formation of new tissues and/or stimulates healing or regrowth of native tissue at the site of injection can include, but are not limited to, fibroblast growth factor (FGF), transforming growth factor-beta (TGF-β, platelet-derived growth factor (PDGF), epidermal growth factors (EGFs), connective tissue activated peptides (CTAPs), osteogenic factors including bone morphogenic proteins, heparin, angiotensin II (A-II) and fragments thereof, insulin-like growth factors, tumor necrosis factors, interleukins, colony stimulating factors, erythropoietin, nerve growth factors, interferons, biologically active analogs, fragments, and derivatives of such growth factors, and any combinations thereof.

Anesthetics can include, but are not limited to, those used in caudal, epidural, inhalation, injectable, retrobulbar, and spinal applications, such as bupivacaine, lidocaine, benzocaine, cetacaine, ropivacaine, and tetracaine, or combinations thereof.

In some embodiments, the one or more active agents included in the compositions and/or particles (e.g., silk fibroin particles) described herein may be cosmetically active agents. By the term "cosmetically active agent" is meant a compound that has a cosmetic or therapeutic effect on the skin, hair, or nails, e.g., anti-aging agents, anti-free radical agents, lightening agents, whitening agents, depigmenting agents, darkening agents such as self-tanning agents, colorants, anti-acne agents, shine control agents, anti-microbial agents, anti-inflammatory agents, anti-mycotic agents, anti-parasite agents, external analgesics, sun-blocking agents, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, muscle relaxants, agents for hair, nail, and/or skin conditioning, and any combination thereof.

In one embodiment, the cosmetically active agent can be selected from, but not limited to, the group consisting of hydroxy acids, benzoyl peroxide, sulfur resorcinol, ascorbic acid, D-panthenol, hydroquinone, octyl methoxycinnamate, titanium dioxide, octyl salicylate, homosalate, avobenzone, polyphenolics, carotenoids, free radical scavengers, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, feverfew, and soy, and derivatives and mixtures thereof. Examples of vitamins include, but are not limited to, vitamin A, vitamin Bs (such as vitamin B3, vitamin B5, and vitamin B12), vitamin C, vitamin K, and vitamin E, and derivatives thereof.

In one embodiment, the one or more cosmetically active agents included in the compositions and/or particles (e.g., silk fibroin particles) may be antioxidants. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid, and ascorbic acid derivatives (e.g., ascorbyl palmitate and ascorbyl polypeptide). Oil-soluble antioxidants suitable for use in the compositions described herein include, but are not limited to, butylated hydroxytoluene, tocopherols (e.g., tocopheryl acetate), tocotrienols, and ubiquinone. Natural extracts containing antioxidants suitable for use in the injectable compositions described herein, include, but not limited to, extracts containing flavonoids and isoflavonoids and their derivatives (e.g., genistein and diadzein), and extracts containing resveratrol. Examples of such natural extracts include grape seed, green tea, pine bark, and propolis.

In some embodiments, the active agents can be cell attachment agents. Examples of cell attachment agents include, but are not limited to, hyaluronic acid, collagen, crosslinked hyaluronic acid/collagen, an integrin-binding molecule, chitosan, elastin, fibronectin, vitronectin, laminin, proteoglycans, any derivatives thereof, and any combinations thereof.

In some embodiments, the compositions or injectable compositions and/or particles (e.g., silk fibroin particles) can further comprise at least one additional material for soft tissue augmentation, e.g., additional filler materials, including, but not limited to, poly(methyl methacrylate) microspheres, hydroxyapatite, poly(L-lactic acid), collagen, elastin, and glycosaminoglycans, and/or hyaluronic acid.

In some embodiments where the compositions or injectable compositions are formulated, e.g., for use as dermal fillers, the compositions or injectable compositions may further comprise a commercial dermal filler product such as BOTOX® (from Allergan), DYSPORT®, COSMODERM®, EVOLENCE®, RADIESSE®, RESTYLANE®, JUVEDERM® (from Allergan), SCULPTRA®, PERLANE®, and CAPTIQUE®, and any combinations thereof.

In some embodiments, the compositions or injectable composition and/or silk fibroin particles can comprise metallic nanoparticles (e.g., but not limited to, gold nanoparticles), optical molecules (e.g., but not limited to, fluorescent molecules, and/or quantum dots), and any other art-recognized contrast agent, e.g., for biomedical imaging.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: Preparation of a Solution Comprising Silk Fibroin Fragments According to One Embodiment Described Herein Silk fibers are boiled in dilute sodium carbonate at about 0.02 M for about 60 minutes or longer. Following boiling for the desired amount of time, the silk fibers are rinsed at least 3 times in deionized water. Degummed silk fibers are then dissolved in about 9.3 M LiBr solution and placed in a dry oven at about 60° C. for about 4 hours. The LiBr is then removed from the silk fibroin solution by dialysis over several days. Once the LiBr is completely or substantially removed, the silk fibroin solution is passed through vacuum filtration, e.g., using a 0.22 μm vacuum filtration system. The silk fibroin solution can then be further concentrated, as needed. Following the silk fibroin solution processing, the concentration of the solution is determined according to equation (2) below, and the solution is adjusted to be about 10% (w/v).

The concentration of a silk fibroin solution is determined using the following equation (2):

$$\frac{(W3 - W1)}{(W2 - W1)} \times 100 = \%$$

where W1 is the weight of an empty weighing boat, W2 is the weight of about 500 μL of the silk fibroin solution and W3 is weight of about 500 μL of the silk fibroin solution once the water has been removed (the "dried weight" of silk fibroin).

Example 2: Addition of a Plasticizer, e.g., Glycerol

An about 0.7 g/mL solution of a plasticizer, e.g., glycerol, is added slowly to a silk fibroin solution, e.g., one as prepared following the method as described in Example 1, under continuous stirring at room temperate to achieve a desirable concentration of the plasticizer, e.g., a final concentration of about 6% (w/w) glycerol. The solution is then diluted to achieve a final concentration of about 10% (w/v) silk fibroin (i.e., about 10% (w/w) silk fibroin) and about 0.6% (w/v) glycerol (i.e., about 6% (w/w) glycerol).

For clarification, the concentration unit, % (w/v), as used herein, when used in reference to silk fibroin, means the amount of silk fibroin in grams per 100 mL solution (e.g., water). For example, 10% (w/v) silk fibroin means 10 g silk fibroin in 100 mL solution (e.g., water), which corresponds to 9.1 g of silk fibroin relative to 100 g of water.

The concentration unit, % (w/w), as used herein, when used in reference to a plasticizer (e.g., glycerol), means the mass of a plasticizer (e.g., glycerol) relative to the mass of silk fibroin. For example, 6% (w/w) glycerol means 6 g of glycerol relative to 100 g of silk fibroin.

Example 3: Density Calculation

Density of a silk fibroin solution can be determined by measuring about 1 mL of solution in a specific-gravity container, and taking the dried weight of silk fibroin.

Example 4: Measurement of Weight Average Molecular Weight of a Silk Fibroin Solution Using Gel Electrophoresis A solution comprising about 0.075% (w/v) silk fibroin was reduced, for example, using dithiothreitol, in the presence of lithium dodecyl sulfate containing a coomassie stain. An aliquot of the reduced silk fibroin solution (e.g., about 10 microliters) was pipetted into a lane of the 3-8% NuPage Tris Acetate gel. The gel was run in the running buffer containing Tris acetate. The voltage for running the gel was set to about 200 mV with the starting current at about 125 mV and the end current at about 80 mV. The time for protein band migration lasted approximately one hour.

After completion of the gel electrophoresis, the gel was stained with colloidal blue, for example, for about 3 hours, and then destained, for example, with deionized water for about 12 hours.

Images of the stained gel were captured and uploaded into gel analysis tool, e.g., ImageJ. The images were converted to grayscale and then subsequently inverted. The "Analyze Gel" function of the ImageJ or other functionally equivalent gel analysis tool was used to provide a densitometric pixel intensity distribution against a protein standard ladder, e.g., HiMark Prestained Protein Standard (Life Technologies). To account for the inherent noise in the gel image, the pixel intensity area of the background area between lanes was subtracted from the pixel intensity area generated from the sample lane. Average molecular weight distributions were determined for each range by determining bracketing positions from the protein standard ladder:

(1) 460-268 kDa
(2) 268-238 kDa
(3) 238-171 kDa
(4) 171-117 kDa
(5) 117-71 kDa
(6) 71-55 kDa
(7) 55-41 kDa
(8) 41-31 kDa

The pixel intensity (PI) distribution for each bracket can be calculated as follows. For example, the pixel intensity distribution for the bracket 460-268 kDa is:

Pixel intensity (PI) distribution for MW 460-268 kDa= ($PI_{460\text{-}268\ kDa}$) divided by the sum of ($PI_{460\text{-}268\ kDa}$, $PI_{268\text{-}238\ kDa}$, $PI_{238\text{-}171\ kDa}$, $PI_{171\text{-}117\ kDa}$, $PI_{117\text{-}71\ kDa}$, $PI_{71\text{-}55\ kDa}$, $PI_{55\text{-}41\ kDa}$, and $PI_{41\text{-}31\ kDa}$)

After determining the pixel intensity distribution for all 8 ranges, the weight average molecular weight can be calculated as:

SUM(pixel intensity distribution for each MW range multiplied by the median of the range)

For example, if the pixel intensity distribution of silk fibroin having a MW range of 460-268 kDa is 5% ($W_1$), then the weight average molecular weight can be calculated as follows: $=0.05*(460-268)/2+W_2*(268-238)/2+W_3*(238-171)/2+W_4*(171-117)/2+W_5*(117-71)/2+W_6*(71-55)/2+W_7*(55-41)/2+W_8*(41-31)/2$ FIGS. 1A-1B show the molecular weight distribution of a solution comprising silk fibroin fragments as prepared in Example 1. The molecular weight of the silk fibroin solution was determined by gel electrophoresis/SDS-PAGE. FIG. 1A shows a molecular weight distribution graph. FIG. 1B shows a picture of SDS-PAGE, where the first lane shows a protein ladder and each of the remaining lanes corresponds to a sample of a composition comprising silk fibroin fragments. The solution comprises low molecular silk fibroin fragments. In some embodiments, at least about 25% of the silk fibroin fragments in the solution have a molecular weight of between about 31 kDa and about 55 kDa. In some embodiments, at least about 35% of the silk fibroin fragments in the solution have a molecular weight of between about 31 kDa and about 71 kDa. In some embodiments, at least about 55% of the silk fibroin fragments in the solution have a molecular weight of between about 31 kDa and about 117 kDa. In some embodiments, at least about 70% of the silk fibroin fragments in the solution have a molecular weight of between about 31 kDa and about 171 kDa. In some embodiments, at least about 90% of the silk fibroin fragments in the solution have a molecular weight of under about 238 kDa. In some embodiments, no more than 10% of the silk fibroin fragments in the solution have a molecular weight of over 238 kDa.

Example 5: Measurement of Molecular Weight and Polydispersity of a Silk Fibroin Solution Using High Performance Liquid Chromatography (HPLC)-Refractive Index Detector (RID)

A silk fibroin solution (e.g., as described in Example 1) was subjected to HPLC-RID analysis to determine molecular weight and polydispersity.

Analysis conditions for gel permeation chromatography (GPC) were as follows: samples were monitored using an RI 2012 refractive index detector. Data acquisition and handling was made with Jordi GPC software. Data was obtained under the following conditions: the solvent was Hexafluoroisopropanol (HFIP) with 0.01 M NaTFA; the flow rate was about 1.0 mL/min; the injection volume was about 50 µL for the sample and about 50 µL for the standards; the column used was the Jordi Resolve xStream Mixed Bed 5µ, 7.8×300 mm and the run time was about 20 minutes and the column temperature was about 40° C.

The sample preparation conditions were described as follows: about 24 hours at ambient temperature with orbital shaking, followed by about 15 minutes in the oven at about 50° C. The sample was then filtered with 0.45 µm PTFE.

The standards used in the analysis included polymethyl methacrylate (molecular weight: 1,568K; 617.5K; 320K; 137.8K; 66.65K; 26.08K; 10.28K; 4.77K; 1.95K; and 960 Da).

Figures 2A, 2B:
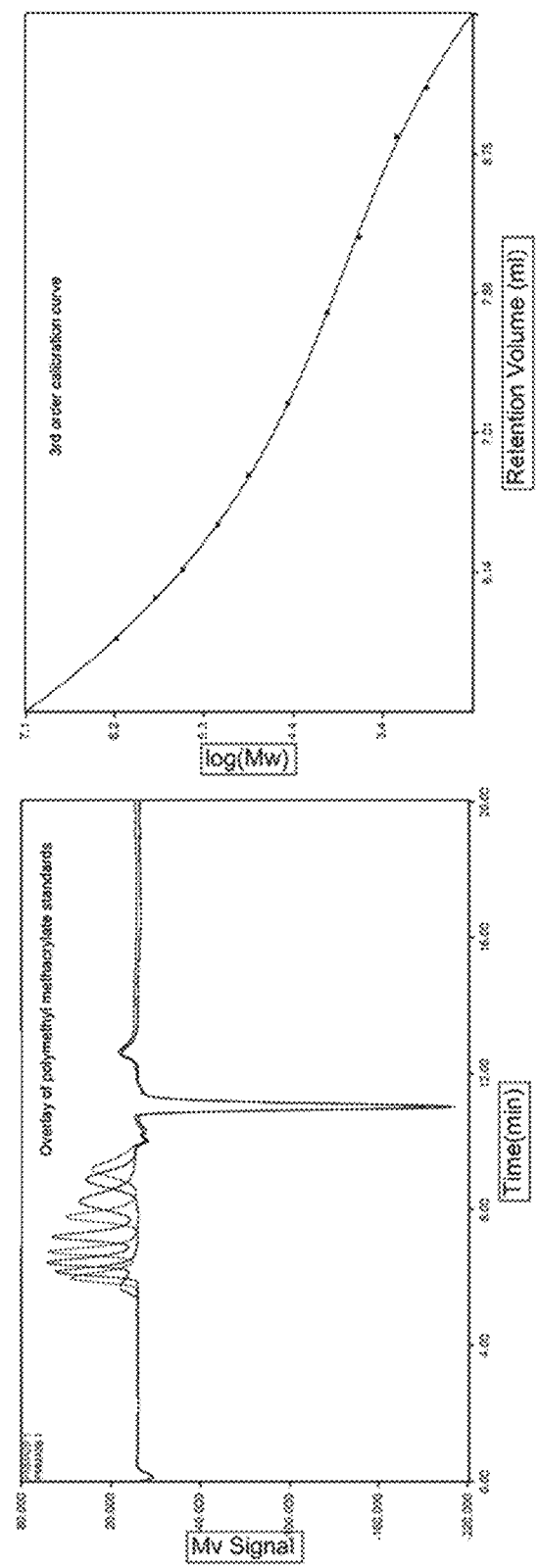
FIGS. 2A-2B show HPLC-RID calibration data using polymethyl methacrylate standards.

FIGS. 2A-2B show the HPLC-RID calibration data using the standards as described above.

FIGS. 3A-3B show the HPLC-RID chromatograms of a silk fibroin solution (having a concentration of about 1.25 mg/mL). The silk fibroin protein was solubilized in either water (where silk fibroin proteins remain in native form) or SDS/DTT solution (where silk fibroin proteins are denatured or reduced). An aliquot of the silk fibroin solution was then mixed with HPLC solvent (e.g., HFIP containing 10 mM trifluoroacetic acid) for the run. FIG. 3A shows a chromatogram of the silk fibroin solution using a mobile phase of about 10% water and about 90% HFIP containing about 10 mM trifluoroacetic acid, while FIG. 3B shows a chromatogram of the silk fibroin solution using a mobile phase of about 10% SDS/DTT and about 90% HFIP containing about 10 mM trifluoroacetic acid.

Example 6: Measurement of Glass Transition Temperature of a Silk Fibroin Solution Differential scanning calorimetry (DSC) (Q100, TA Instruments, New Castle, Del.) was used to measure thermal transition properties of silk fibroin solutions (e.g., about 10% w/v) with or without a plasticizer, e.g., glycerol (e.g., about 0.6% w/v). 10 µL of liquid sample was pipetted into a pre-weighed aluminum pan. Pans were covered with aluminum lids, hermetically sealed, and massed to determine sample weight. Filled pans were added onto the sample holder. Empty aluminum pans were used for reference measurements. A protocol was created to cool the samples from room temperature (approximately about 26° C.) down to about −30° C. at a rate of about 1° C./min, followed by a ramp back up to room temperature at the same rate.

Thermal transitions were detected during the temperature cycle. Notably, as shown in FIG. 8A, a large exothermic peak was observed during the cooling ramp, likely attributed to freezing of the solution. During the heating ramp, clear endothermic glass transition ($T_g$) peaks were observed for the polymer, as well as a melting endotherm for water. As shown in FIG. 8B, for silk fibroin solutions without a plasticizer such as glycerol, the $T_g$ was about −12.15° C.±0.10° C., while the $T_g$ for silk fibroin solutions with a plasticizer (e.g., 6% (w/w) glycerol) were about −18.32° C.±0.11° C.

Figures 9A, 9B:
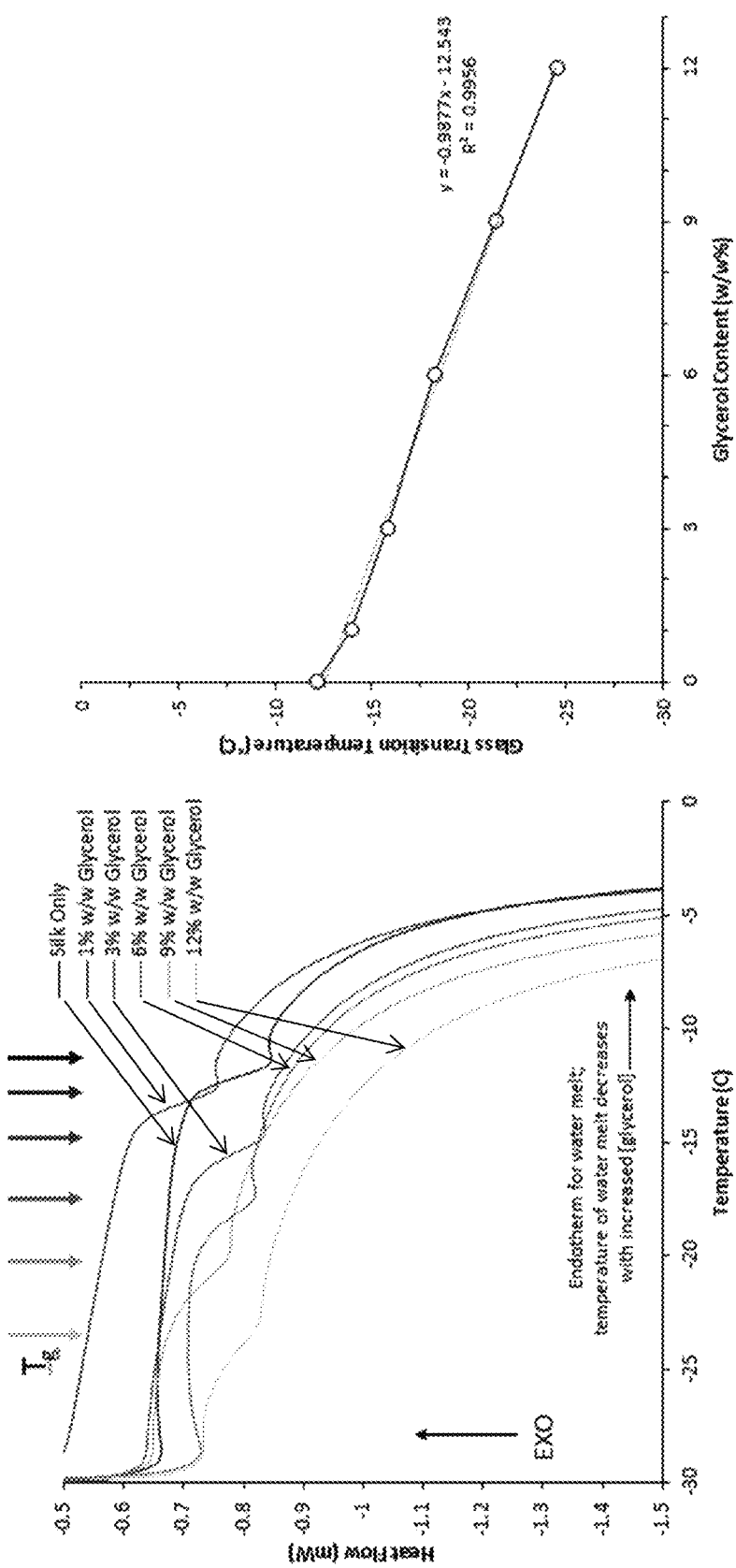
FIGS. 9A-9B show differential scanning calorimetry data for silk fibroin solutions with or without glycerol at varying concentrations.

FIGS. 9A-9B show the glass transition temperature of a silk fibroin solution (e.g., one as prepared in Example 1) with a plasticizer, e.g., glycerol at a concentration in a range of about 1% (w/w) to about 12% (w/w). Addition of a plasticizer, e.g., glycerol, decreases the glass transition temperature ($T_g$) of a silk fibroin solution.

Glass transition temperature ($T_g$) represents the temperature at which a semi-solid phase changes into a rubbery/viscous state. To create freeze-dried silk fibroin scaffolds or sponges, it is desirable to have silk-glycerol solutions at a temperature below $T_g$ prior to sublimation. If this condition is not met, freeze-dried scaffolds may collapse during the sublimation step, corrupting the integrity of pores and scaffold architecture. Glycerol addition reduces the glass transition temperature, making it more difficult for the solution to freeze. Thus, too high glycerol concentration could prevent silk fibroin solutions from freezing because of too low Tg. However, addition of glycerol may be beneficial in that glycerol also limits water crystal growth during freezing, and this can aid in the development of scaffolds or sponges with smaller and more round pores, as shown in FIGS. 12A-13C. Therefore, glycerol concentration should be balanced such that correct pore size and/or shape can be achieved for a particular application without damaging the integrity of the porous architecture during freeze-drying.

The $T_g$ reported herein was calculated using differential scanning calorimetry (DSC). Addition of a plasticizer (e.g., glycerol) at an appropriate concentration to a low molecular weight silk fibroin solution changed the $T_g$ of the final low molecular weight (LMW) silk fibroin solution. Table 1 summarizes how physical parameters of a silk fibroin solution change upon changing the weight average molecular weight of the solution, boil time (e.g., in about 0.02 M $Na_2CO_3$) and glycerol content.

those low molecular weight solutions previously described, e.g., in Kluge, J. A. et al. 2016. *ACS Biomaterials Science & Engineering*, 2, 595-605. This shift to a colder glass transition temperature means that at a colder temperature, the compositions described herein can maintain the malleable phase until the lower Tg is reached. Unlike the LMW silk fibroin solutions without glycerol, the compositions described herein can be exposed to colder temperatures before they are transformed into "glassy" materials or crystalline materials. Thus, the resulting compositions described herein are more rubbery than similar materials produced from the previously described silk fibroin solutions. Such physical properties provide the capability of reducing (e.g., milling) the freeze-dried compositions described herein to form rounder and more uniform particles than silk fibroin materials without glycerol. See Example 9.

Example 7: Porous Dried Particles

Figure 14:
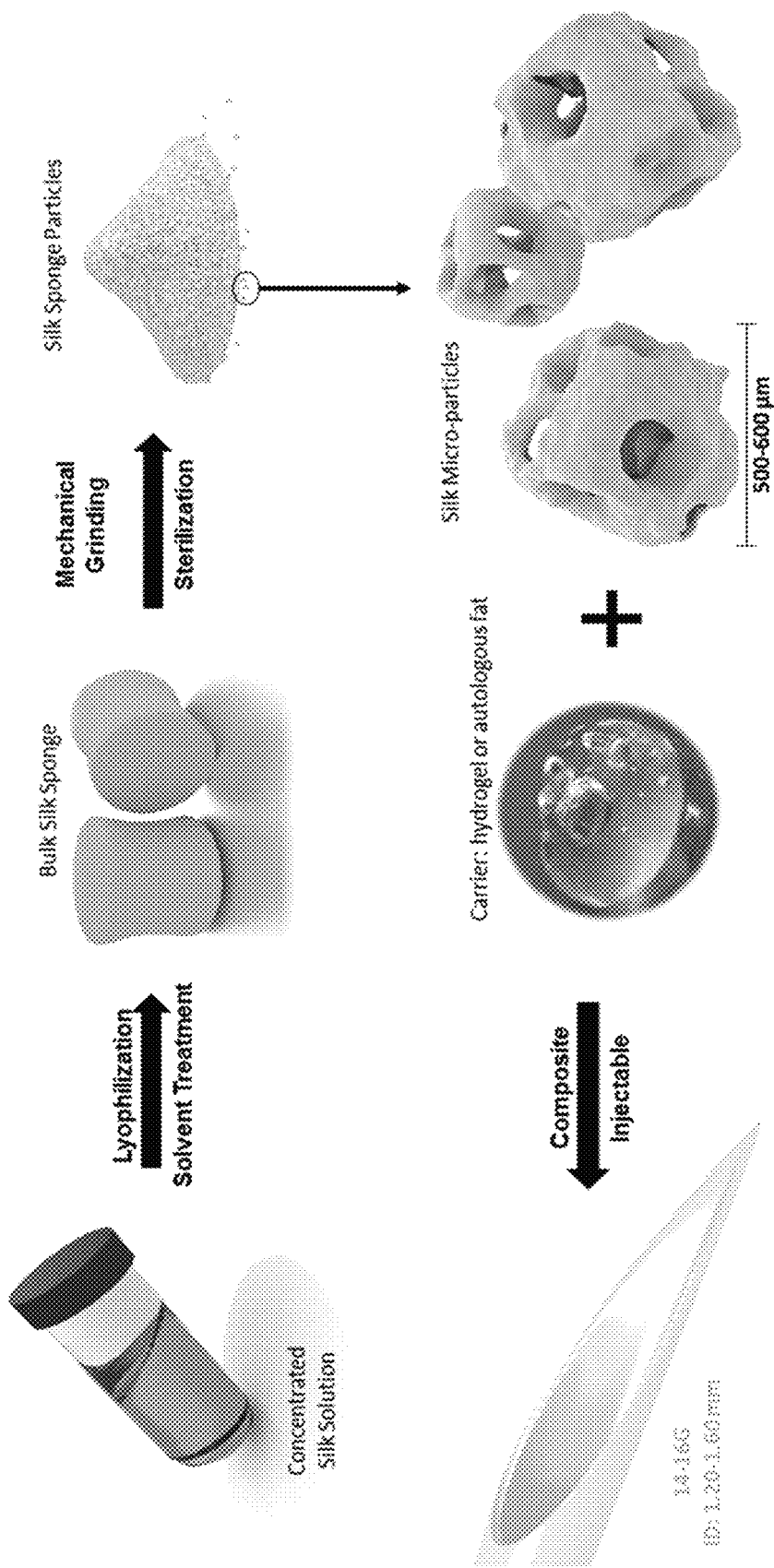
FIG. 14 is a schematic representation of an exemplary method for making silk fibroin particles according to one set of embodiments described herein.

FIG. 14 is a schematic representation of an exemplary method of making silk particles and compositions according to some embodiments described herein. The low molecular weight silk fibroin particles are derived from a bulk low molecular weight silk fibroin sponge produced according to one embodiment of the method described in the International Patent Publication No. WO 2016/145281, the content of which is incorporated herein by reference in its entirety. A low molecular weight silk fibroin solution (e.g., about 10% w/v) mixed with a plasticizer (e.g., glycerol) at a concentration of about 6% w/w (e.g., about 0.6% w/v) is

TABLE 1

| Physical Property | Existing Silk Solution** (30 min boil of silk in 0.02M $Na_2CO_3$) | Prior LMW Silk Solution* (60 min boil of silk in 0.02M $Na_2CO_3$) | One embodiment of the compositions described herein (60 min boil of silk in 0.02M $Na_2CO_3$) |
|---|---|---|---|
| Density | N/A | N/A | 1.0146 ± .0012 g/mL |
| Weight-Average Molecular Weight | 151 kDa (SDS-PAGE)** | 131 kDa (SDS-PAGE)** or 111 kDa (HPLC-RID)* | 128 ± 17 kDa (SDS-PAGE; Example 4) or ~139 kDa (HPLC-RID; Example 5) |
| % glycerol (w/v) | 0% (w/v) | 0% (w/v) | 0.6% (w/v) |
| Solubility (5-45° C.) (% relative to maximum theoretical solubility of 50 mg/mL of $H_2O$) | N/A | Solubility from 60%-90% | Solubility from 15%-45% (Example 8) |
| $T_g$ | N/A | −12.15° C. ± 0.10° C. | −18.32° C. ± 0.11° C. |

*Kluge, J. A. et al. 2016. *ACS Biomaterials Science & Engineering*, 2, 595-605. The HPLC-RID condition for the weight-average molecular weight is provided in the Kluge reference. Briefly, the mobile phase used in the Kluge reference comprised 100 mM phosphate buffer (pH 6.8),
**Wray, L. S. et al. 2011. *Journal of Biomedical Materials Research B: Applied Biomaterials*, 99B, 1, 89-101.

Unlike the previously disclosed silk solutions in which silk was boiled in 0.02 M $Na_2CO_3$ for about 30 minutes, the silk fibroin fragments in Table 1. had a lower weight average molecular weight. Without wishing to be bound by theory, longer boiling time in 0.02 M $Na_2CO_3$ can induce cleavage of amide bonds of silk protein backbone, thus resulting in smaller silk fibroin protein fragments. While there are previous reports of lower weight average molecular weight silks, as seen in Table 1 above, there is no previous report of a LMW silk fibroin solution with a $T_g$ at or below −15° C. or −18° C. The shift in $T_g$ described for this combination of a LMW silk fibroin solution and glycerol indicates that the material accommodates different freezing characteristics and result in solid porous formats that are less brittle than prepared and then frozen in a lyophilizer under slow freezing rate to produce a sponge-like material with inter-connected pores.

After lyophilization, the silk fibroin/plasticizer material is subjected to solvent treatment, e.g., immersion in about 90% methanol, and drying to remove methanol, for example, for about 3-72 hours, to form a bulk silk fibroin sponge. Formation of β-sheet structure in silk fibroin can be evaluated via Fourier Transform Infrared Spectroscopy (FTIR), which is well established in the art. Measurement of β-sheet content is typically performed by FTIR spectral deconvolution and peak fitting. This method is a manipulation of the data, and meant to represent comparative data, rather than empirical values. In some embodiments, an increase in β-sheet content as detected by FTIR analysis from 20-30% β-sheet before methanol treatment, to approx. 45-55% β-sheet after methanol treatment is contemplated. This change would be enough to greatly reduce the solubility of dried silk materials in aqueous media (e.g., buffer solutions such as phosphate buffered saline, water), and extend in vivo volume retention.

The silk fibroin sponge is then subjected to mechanical grinding and sterilization to form silk fibroin particles according to one set of embodiments described herein. FIG. 15A shows a microscopic image of individual silk fibroin particles according to one set of embodiments described herein. FIG. 15B shows the particle morphology in the absence of a plasticizer.

Without wishing to be bound by theory, the plasticizer can act to protect the porous structure from breaking during a milling process, resulting in particles which are more round and even in size. In some embodiments, the porous silk fibroin particle have an average particle size of about 50 microns to about 1000 microns in diameter and an average pore size of about 40 µm in diameter. In some embodiments, the porous silk fibroin particle have an average particle size of about 500 microns to about 600 microns in diameter and an average pore size of about 40 µm in diameter. Such particle sizes can provide mechanical support to a carrier for tissue bulking, e.g., to retain tissue volume over a specified duration, e.g., of one year or longer. In addition, the porous, three-dimensional structure of the silk fibroin particles promotes cell attachment and migration, which in turns promotes interactions with the surrounding matrix for cell proliferation. Additionally, the slow degradation rate of the particles in vivo offers long-term scaffolding and support.

Figure 10E:
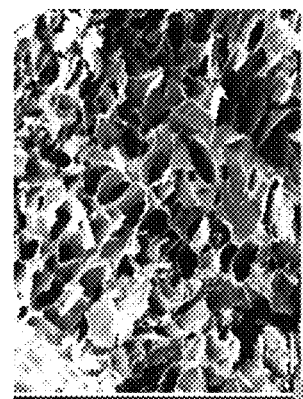
FIGS. 10A-10F shows scanning electron microscopic (SEM) images of freeze-dried silk fibroin materials with or without glycerol.
Figure 10D:
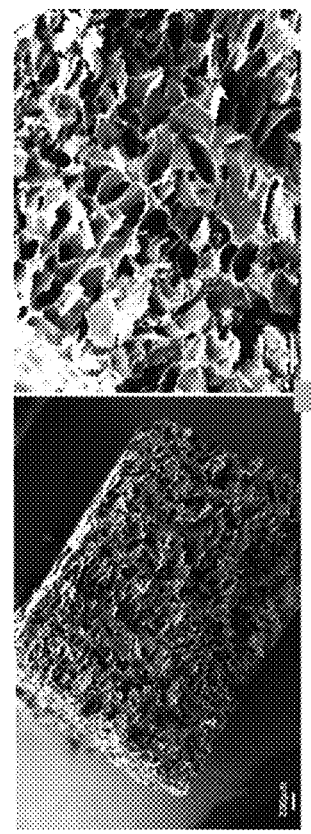
Figure 10F:
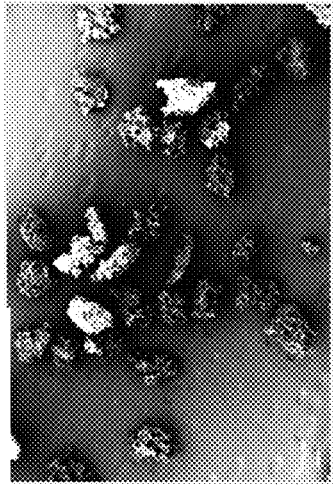
Figure 10B:
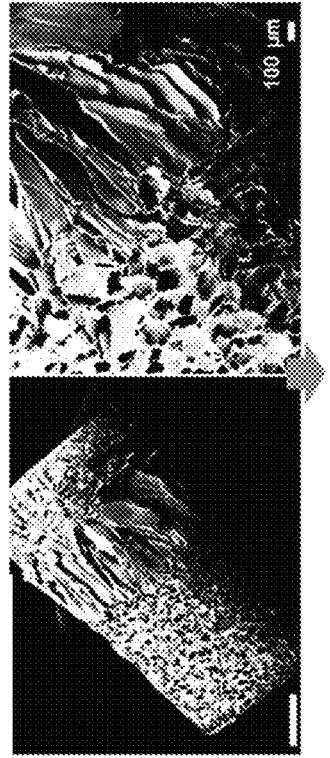
Figure 10A:
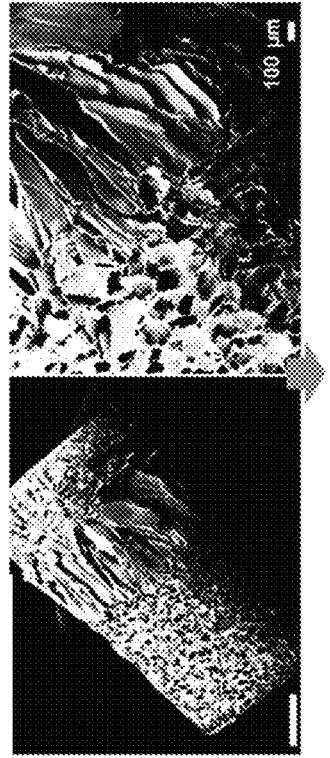
Figure 10C:
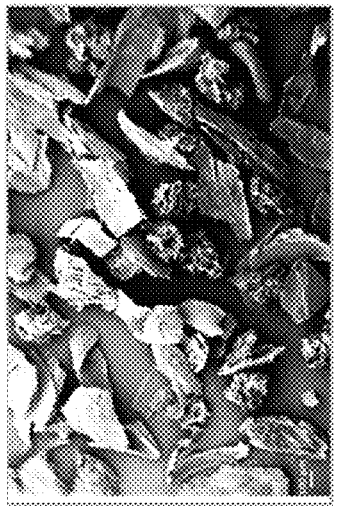
Figure 11A:
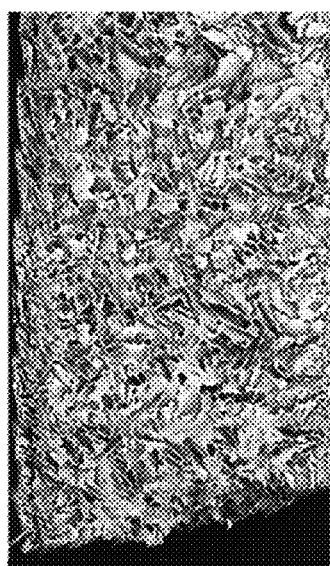
FIGS. 11A-11F show scanning electron microscopic (SEM) images of freeze-dried silk fibroin materials with glycerol at varying concentrations.
Figure 11B:
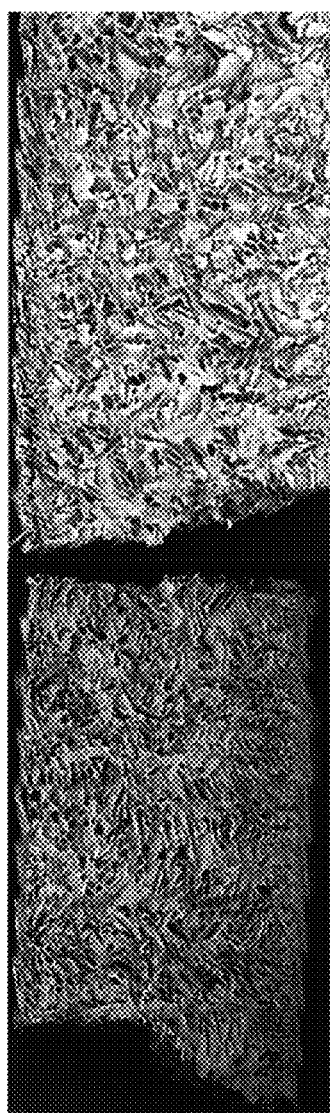
Figure 11C:
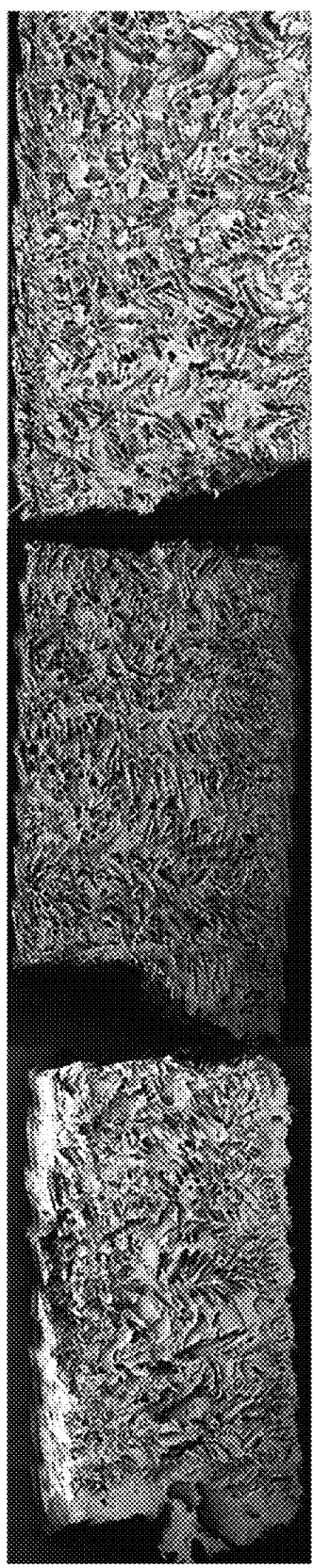
Figure 11D:
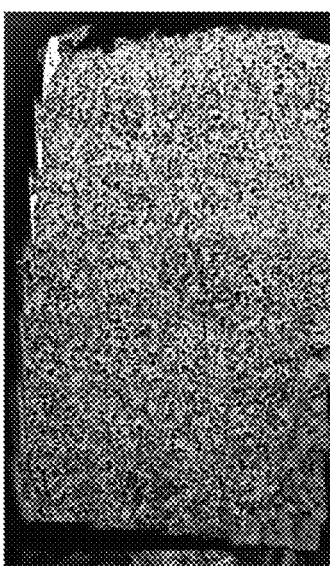
Figure 11E:
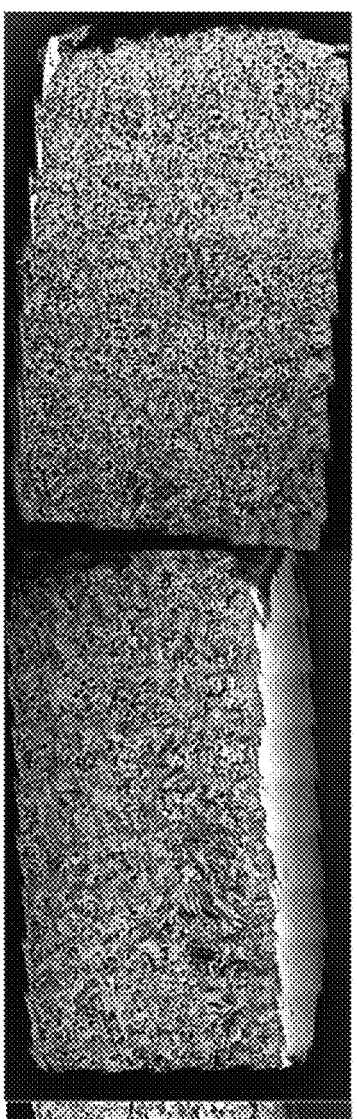
Figure 11F:

FIGS. 10D-10F show scanning electron microscopic (SEM) images of freeze-dried silk fibroin materials with glycerol (e.g., at about 6% (w/w)). FIGS. 10A-10C show scanning electron microscopic (SEM) images of freeze-dried silk fibroin materials without glycerol, which yielded larger non-porous crystals. Without wishing to be bound by theory, formation of such larger non-porous crystals from a silk fibroin material without glycerol could be attributed to irregularities in freezing. In contrast, the silk fibroin particles described herein comprising a plasticizer, e.g., glycerol, had a more uniform size and contained more evenly distributed, rounded pores. These results show that addition of a plasticizer, e.g., glycerol, can reduce or prevent inconsistent, non-homogenous freezing patterns.

Example 8: Silk Fibroin Solubility Assay Protocols

The addition of glycerol can affect the solubility of a silk fibroin material. A comparison was done to examine the difference in solubility observed for silk (without glycerol) vs. silk/glycerol thin films. The film casting/dissolution protocol is as follows: about 50 µL of about 10% w/v silk fibroin solution containing varying concentrations of glycerol (about 0, about 1, about 3, about 6, about 9, and about 12 w/w %, respectively) were cast onto 8 mm discs of polydimethylsiloxane (PDMS) and allowed to dry overnight under laminar flow. Upon drying, the dried silk films were placed in a 2.0 mL Eppendorf tube. To the films (containing ~0.005 g silk fibroin and varying amounts of glycerol) in the tube, about 100 µL deionized water (e.g., at a pH in a range of about 6.0 to about 7.0) was added and the films were allowed to solubilize. Films were stored at about 5° C., about 25° C., and about 45° C., respectively, in triplicate for about one hour. The maximum theoretical solubility of silk fibroin in this Example is 5% w/v (i.e., 5 g silk fibroin in 100 mL water, or 50 mg silk fibroin in 1 mL water, or 5 mg silk fibroin in 100 µL water).

The fluorescence solubility assay protocol is as follows: After solubilizing for about one hour, 50 µL of supernatant from each condition was added to a well of a clear 96-well plate. Fluorescence values were measured from the top of the plate using a Biotek Synergy Plate Reader at a read height of 1 mm ($Ex_{360\ nm}/Em_{460\ nm}$, Gain=90). Solubilized silk fibroin concentration was quantified using fluorescence and determined against a silk solution standard curve containing glycerol with a linear range between 0-8 w/v % silk fibroin.

Figures 4A, 4B:
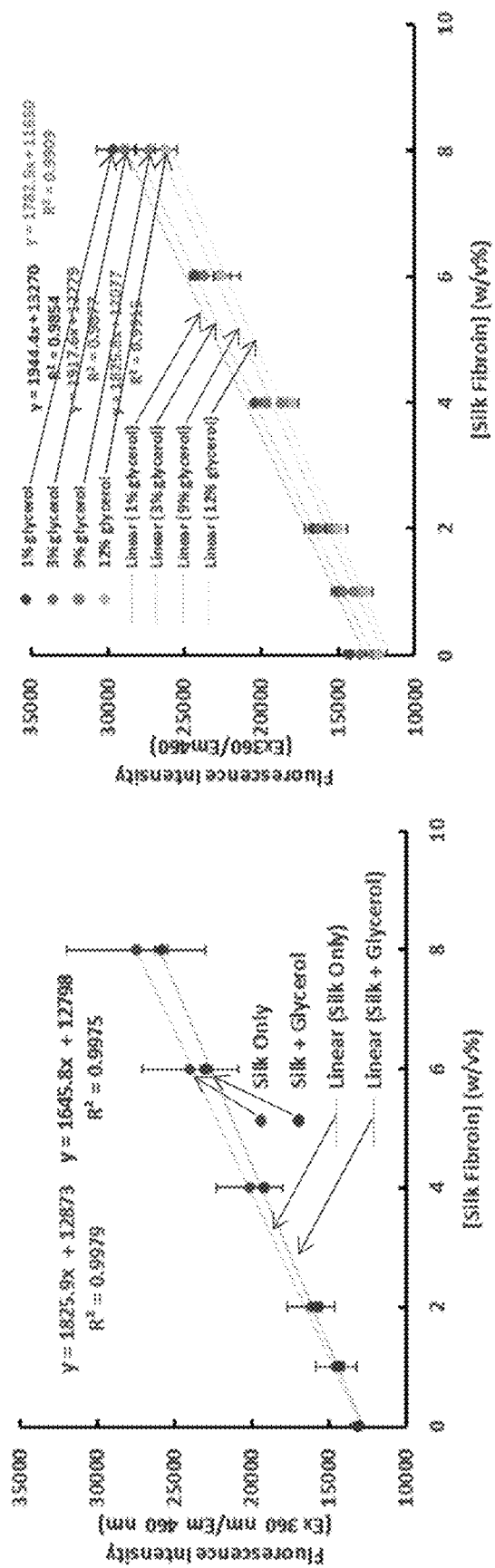
FIGS. 4A-4B show calibration curves of fluorescence intensity (Ex360 nm/Em460 nm) as a function of silk fibroin concentration (w/v).
Figures 5A, 5B:
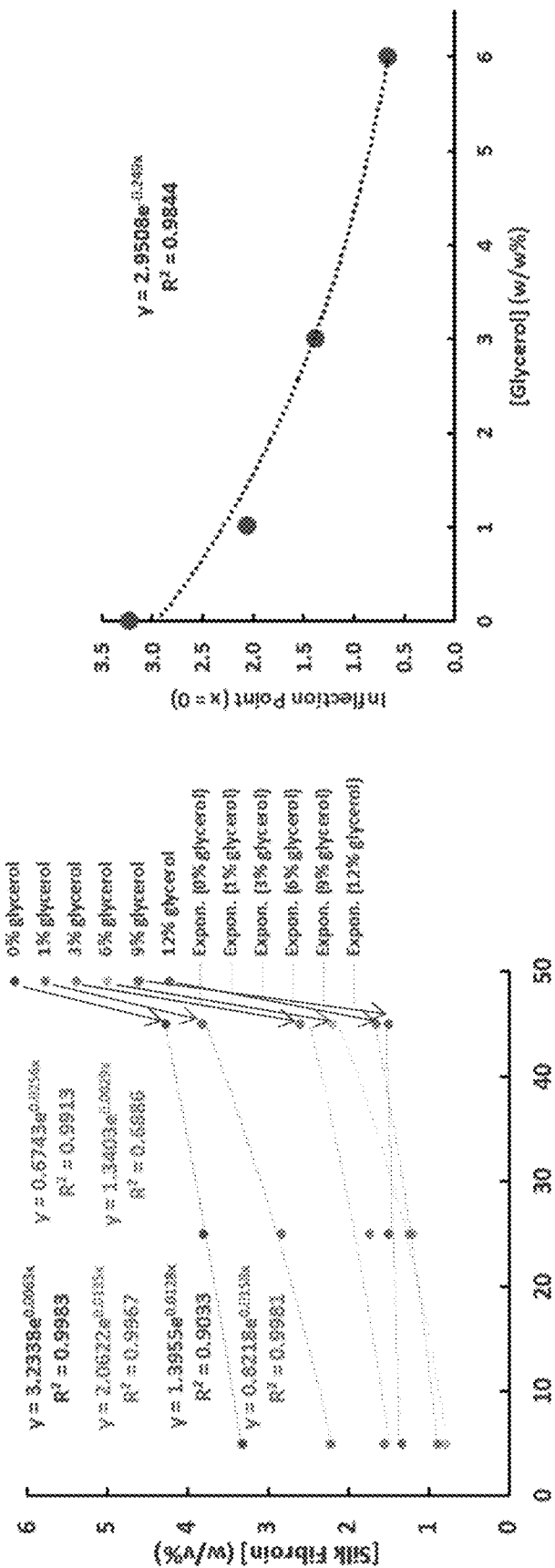
FIGS. 5A-5B show solubility curves of silk fibroin films comprising glycerol according to some embodiments described herein.

FIGS. 4A-4B show calibration curves of silk fibroin solution (with or without glycerol at a concentration in a range of about 1% (w/w) to about 12% (w/w). FIG. 5A shows the amount of silk fibroin solubilized (in milligrams per 100 µL water; % (w/v)) as a function of temperature as observed in silk fibroin compositions comprising glycerol at different concentrations. When glycerol was added at a concentration of above 6% (w/w), the relative solubility of the silk fibroin film in water is negligible. FIG. 5B shows the amount of silk fibroin solubilized (in milligrams per 100 µL water; % (w/v)) at temperature=0° C. as a function of glycerol concentration in silk fibroin compositions. Such values corresponding to the amount of silk fibroin solubilized at temperature=0° C. as observed in silk compositions comprising glycerol at different concentrations were determined by extrapolating the data in FIG. 5A until it crosses the temperature crossed 0° C. ("Inflection point"). As glycerol concentration in the silk fibroin solution increases, the inflection point decreases exponentially.

To determine the solubility of silk fibroin films relative to the total amount of silk fibroin present in the silk fibroin films, the solubility values (% w/v) shown in FIG. 5A is divided by the maximum theoretical solubility of silk fibroin (which is 5% w/v in this Example). For example, if the solubility shown in FIG. 5A is 1% (w/v), the relative solubility would be 20%.

Figure 6:
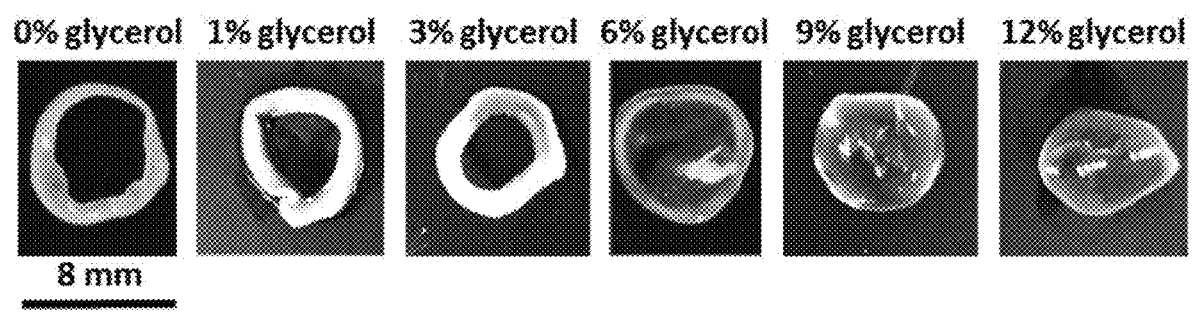
FIG. 6 shows images of silk fibroin films (with varying glycerol concentrations) upon dissolving in about 100 µL deionized water for about 1 hour.

FIG. 6 shows images of silk fibroin films (with varying glycerol concentrations) upon dissolving in about 100 µL deionized water at room temperature for about 1 hour. Images were captured with a camera. At lower glycerol concentrations, the center of the films were hollow, showing solubility of silk fibroin films in water. At higher glycerol concentrations, the integrity of the entire silk fibroin film remained intact. As glycerol concentration increases, the solubility of silk fibroin films decreases. Without wishing to be bound by theory, this can be attributed to the higher instances of beta-sheeting observed at higher glycerol concentrations, adding strength to the film (see FIG. 7A).

Example 9: Freeze Drying and Pore Analysis

As discussed in detail herein, the addition of a plasticizer also impacts the pore architecture formed by this unique silk solution. To explore this further, a series of silk solutions with varying concentrations of glycerol were subjected to freeze drying. The freeze drying and sample preparation protocol is as follows: about 10% w/v silk fibroin containing no glycerol or varying concentrations of glycerol were freeze-dried in stainless steel pans. After freeze-drying, silk fibroin scaffolds were treated with a beta-sheet inducing agent such as an alcohol (e.g., methanol) overnight to promote beta-sheet formation. After discarding the methanol, the silk fibroin scaffolds were allowed to air-dry for about 24 hours in a fume hood. Cross sections were excised from the scaffolds in random locations (n=6) using a fresh razor with depth dimensions between about 3-4 mm, length dimensions between about 4-6 mm, and width dimensions between about 2-3 mm. Cross sections were mounted on a ~24.4 mm stub containing black double-sided carbon tape. The cross sections were subsequently stained with colloidal graphite for imaging.

FIGS. 10A-10F shows scanning electron microscopic (SEM) images of freeze-dried silk fibroin materials with (FIGS. 10D-10F) or without (FIGS. 10A-10C) glycerol. As compared to the silk fibroin material comprising glycerol (FIGS. 10D-10F), the silk fibroin material without glycerol (FIGS. 10A-10C) contained a combination of porous silk fibroin materials and larger non-porous crystals, which, without wishing to be bound by theory, could be attributed to irregularities in freezing. For example, glycerol may delay or slow freezing such that silk fibroin is not exposed to extreme temperatures in such a rapid timeframe.

FIGS. 11A-11F show cross-sections of silk fibroin scaffolds prepared as described above with glycerol at indicated concentrations. The imaging and pore analysis protocol is as follows. Cross sections were imaged using a PhenomPure Scanning Electron Microscope appended with the Phenom Pro Suite Automated Image Mapping software at an accelerating voltage of 5 kV. Pores within the cross sections were analyzed using the Phenom Porometric software with the following settings: Contrast: ~0.5, Merge Edges: ~0.3, Conductance: ~0.3, and Minimum Pore Size: ~1.50% of image quality. A minimum of about 10,000 pores were analyzed for each sample.

Figure 12B:
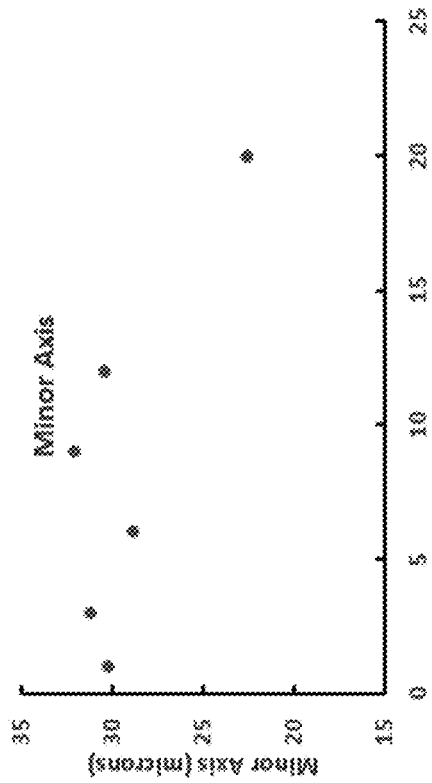
FIGS. 12A-12C show how glycerol concentration affects the size parameters of the freeze-dried silk fibroin scaffold as shown in FIGS. 11A-11F.
Figure 12C:
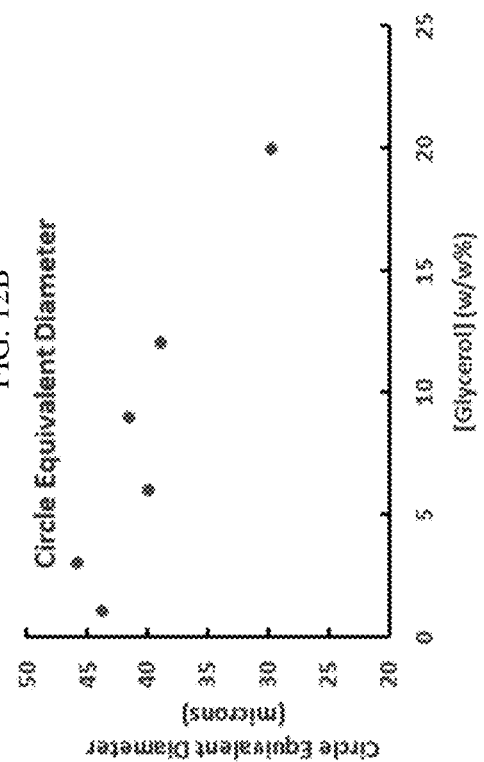
Figure 12A:
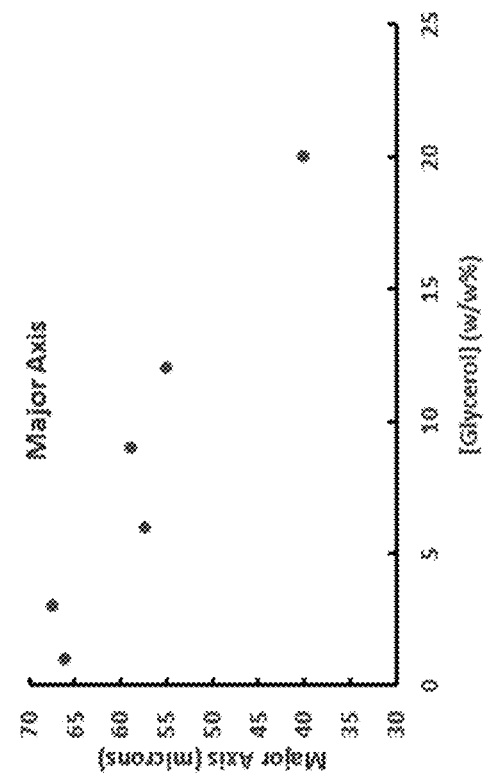

FIGS. 12A-12C show the pore size parameters of freeze-dried silk fibroin scaffold as a function of glycerol concentration. As glycerol concentration increases, the pore size (as characterized by average dimension of the major axis and minor axis of the pores, and average circle equivalent diameter) of the freeze-dried silk fibroin scaffold decreases. Average circle equivalent diameter ($D_{circular}$) is equal to $(4A_{pore}/\pi)^{1/2}$, where $A_{pore}$ is the average cross-section area of the pores. The major axis of a pore is the longest dimension of a pore (e.g., an elliptical pore) that pass through a foci or center of the pore. The minor axis of a pore is the shortest dimension of a pore (e.g., an elliptical pore) that pass through a foci or center of the pore.

Figures 13A, 13B, 13C:
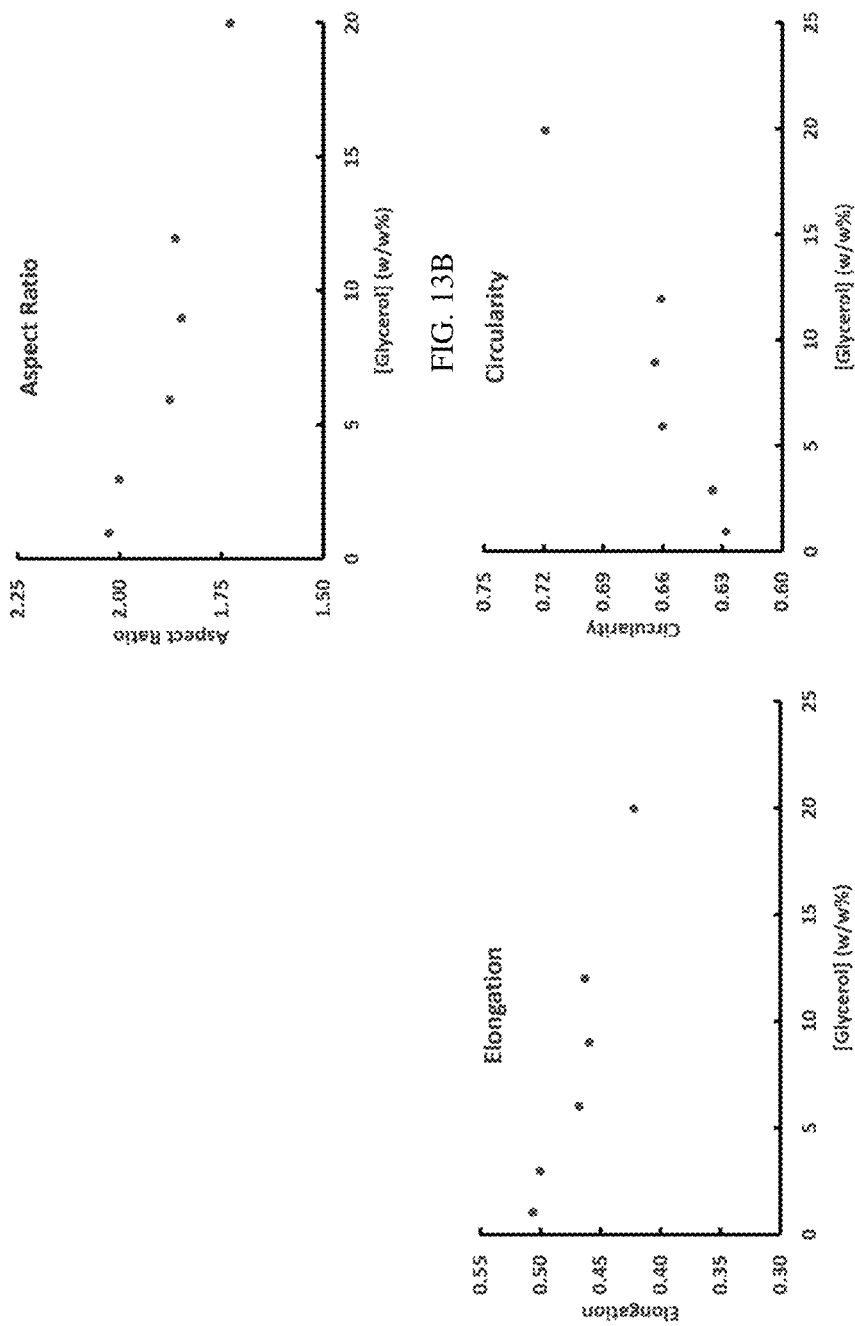
FIGS. 13A-13C show how glycerol concentration affects shape parameters of the freeze dried silk fibroin scaffold as shown in FIGS. 11A-11F.

FIGS. 13A-13C shows pore shape parameters of freeze-dried silk fibroin scaffold as a function of glycerol concentration. As glycerol concentration increases, the pore shape of the freeze-dried silk fibroin scaffold becomes less elongated and more circular. An aspect ratio of 1 signifies perfectly circular, Circularity of 1 signifies perfectly circular, and lower elongation values signifies better circularity. Aspect ratio is determined as a ratio of the major axis dimension to the minor axis dimension. Elongation is determined as: 1–(minor axis dimension/major axis dimension). Circularity is determined as: $(4\pi A_{pore}/P_{pore}^2)^{1/2}$, where $A_{pore}$ is the average cross-section area of the pores and $P_{pore}$ is the average perimeter forming the boundary of the cross-section area of the pores.

Example 10: Beta-Sheet Content Measurement

Figures 7A, 7B:
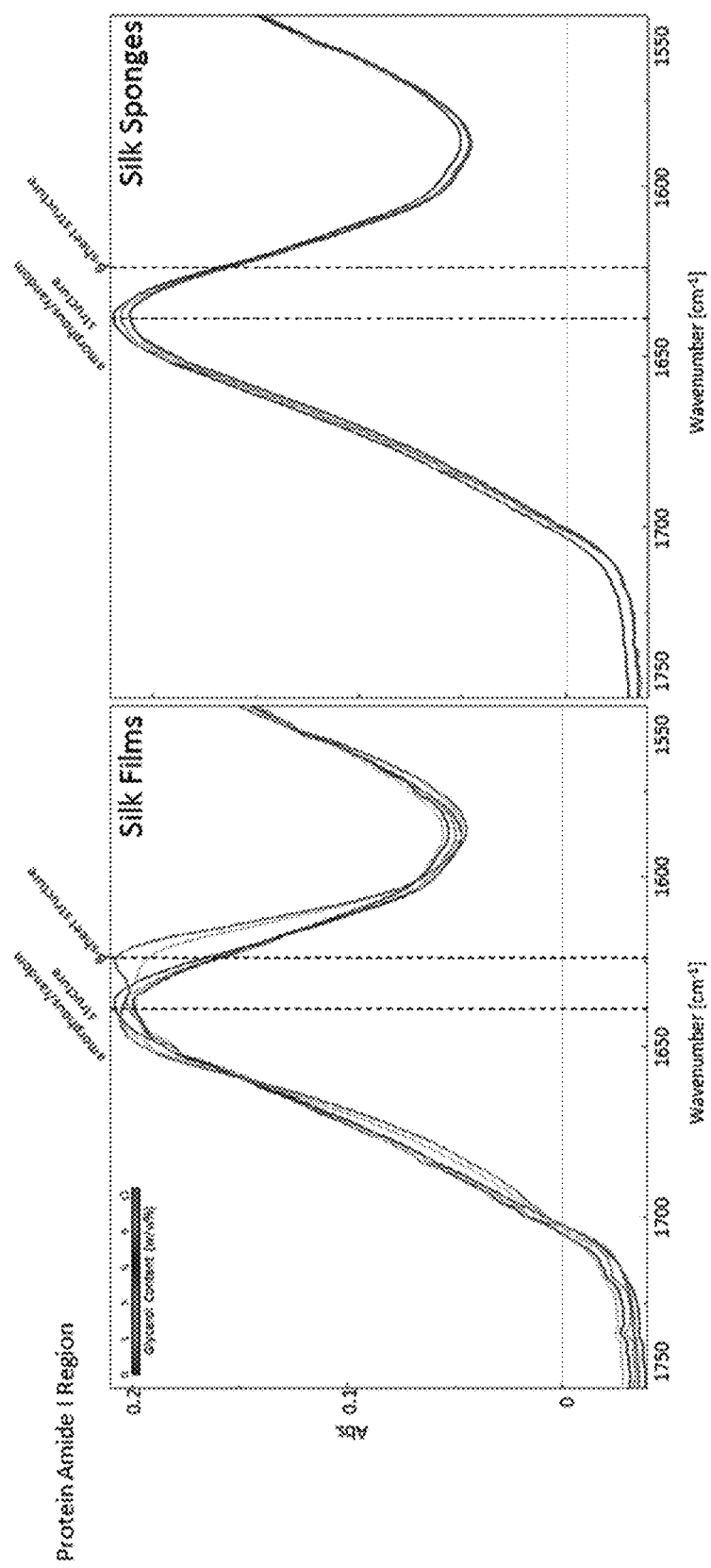
FIGS. 7A-7B show Fourier Transform Infrared Spectroscopy (FTIR) spectrums of silk fibroin compositions comprising glycerol according to some embodiments described herein.

A silk fibroin solution was prepared as described in Example 1 and then optionally added with glycerol at a concentration in a range of about 0-12% w/w. The mixture was then subjected to air-drying to form a silk fibroin film or freeze-drying to form a silk fibroin sponge. FIG. 7A shows a FTIR spectrum of a silk fibroin film. FIG. 7B shows a FTIR spectrum of a silk fibroin sponge. Dried constructs containing a range of glycerol concentrations from about 0-12% w/w have different secondary structure composition when dried into either sponges or films.

Silk fibroin films were fabricated via a slow, uncontrolled evaporation process in ambient environment. As shown in FIG. 7A, silk fibroin films with about 0-3% w/w glycerol show predominantly random/amorphous protein structure, while silk fibroin films with about 6-12% w/w glycerol show increasing β-sheet formation with increasing glycerol.

Silk fibroin sponges were fabricated via a controlled freeze-drying process. As shown in FIG. 7B, the resulting materials show predominantly random/amorphous protein structure, and the glycerol concentration range tested does not induce β-sheet formation. β-sheet formation is a result of molecular mobility and the protein reorganizing into a more energetically favorable structure. Both glycerol and water increase mobility. Without wishing to be bound by theory, film fabrication, as a result of slow evaporative drying, permits greater mobility when compared to freezing, which freezes and sublimates silk fibroin solutions at low temperatures.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A solution for forming a scaffold, the solution comprising silk fibroin fragments and glycerol, the silk fibroin fragments having a weight average molecular weight ranging from about 100 kDa to about 160 kDa, wherein the glycerol and the silk fibroin fragments are present in a weight ratio (glycerol to silk fibroin fragments) of about 1:100 to about 25:100; wherein the solution for forming the scaffold exhibits a glass transition temperature of equal to or less than about −15° C., and wherein the solution for forming the scaffold is sterile;

wherein the silk fibroin fragments display a molecular weight distribution characterized in that: no more than about 20% of the total number of the silk fibroin fragments has a molecular weight exceeding about 200 kDa, and at least about 70% of the total number of the silk fibroin fragments has a molecular weight of about 30 kDa to about 170 kDa, and wherein the solution for forming the scaffold, after sublimation, has a relative solubility in a range of about 1% to about 50%.

2. The solution of claim 1, wherein the glycerol and the silk fibroin fragments are present in a weight ratio of about 1:100 to about 8:100.

3. The solution of claim 1, wherein the solution further comprises an alcohol and/or a polyol.

4. A silk fibroin particle comprising silk fibroin fragments and glycerol, wherein the silk fibroin fragments have a weight average molecular weight ranging from about 100 kDa to about 160 kDa, and wherein the silk fibroin particle comprises a porous structure characterized by interconnected pores having an average circle equivalent diameter of about 5 µm to about 60 µm and having an aspect ratio of about 1.0 to about 3.0, wherein the silk fibroin particle has an aspect ratio of about 1 to about 3, wherein the silk fibroin fragments display a molecular weight distribution characterized in that: no more than about 20% of the total number of the silk fibroin fragments has a molecular weight exceeding about 200 kDa, and at least about 70% of the total number of the silk fibroin fragments has a molecular weight of about 30 kDa to about 170 kDa, and wherein the glycerol and the silk fibroin fragments are present in a weight ratio (glycerol to silk fibroin fragments) of 1:100 to about 25:100.

5. The silk fibroin particle of claim 4, wherein the silk fibroin particle is formed from a lyophilized scaffold.

6. The solution of claim 1, wherein the solution has been sterilized by vacuum filtration.

7. The solution of claim 1, wherein the silk fibroin fragments have a weight average molecular weight ranging from about 130 kDa to about 160 kDa.

8. The solution of claim 1, wherein no more than about 5% of the total number of the silk fibroin fragments have a molecular weight of about 200 kDa or higher.

9. The solution of claim 1, wherein at least about 60% of the total number of silk fibroin fragments have a molecular weight of about 30 kDa to about 170 kDa.

10. A silk fibroin scaffold formed from the solution of claim 1.

11. A silk fibroin particle formed from the scaffold of claim 10.

12. The silk fibroin particle of claim 4, wherein the silk fibroin particle is formed from a sterile solution.

13. The silk fibroin particle of claim 12, wherein the sterile solution, after sublimation, has a relative solubility in a range of about 1% to about 50%.

14. The silk fibroin particle of claim 12, wherein the sterile solution has a glass transition temperature of equal to or less than about −15° C.

15. The silk fibroin particle of claim 4, wherein the glycerol and the silk fibroin fragments are present in the sterile solution at a weight ratio of 1:100 to about 8:100.

16. The silk fibroin particle of claim 12, wherein the sterile solution has been sterilized by vacuum filtration.

17. The silk fibroin particle of claim 4, wherein the silk fibroin fragments have a weight average molecular weight ranging from about 130 kDa to about 160 kDa.

18. The silk fibroin particle of claim 4, wherein the silk fibroin particle is formed from a sterile solution, wherein the sterile solution, after sublimation, has a relative solubility in a range of about 1% to about 50%, and wherein the sterile solution has a glass transition temperature of equal to or less than about −15° C.

19. The silk fibroin particle of claim 18, wherein the sterile solution has been sterilized by vacuum filtration.

\* \* \* \* \*